(12) United States Patent
Bynoe

(10) Patent No.: US 10,953,015 B2
(45) Date of Patent: Mar. 23, 2021

(54) USE OF ADENOSINE RECEPTOR SIGNALING TO REGULATE P-GP FUNCTION

(71) Applicant: CORNELL UNIVERSITY, Ithaca, NY (US)

(72) Inventor: Margaret Bynoe, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/075,195

(22) PCT Filed: Feb. 3, 2017

(86) PCT No.: PCT/US2017/016555
§ 371 (c)(1),
(2) Date: Aug. 3, 2018

(87) PCT Pub. No.: WO2017/136757
PCT Pub. Date: Aug. 10, 2017

(65) Prior Publication Data
US 2019/0038630 A1  Feb. 7, 2019

Related U.S. Application Data

(60) Provisional application No. 62/290,763, filed on Feb. 3, 2016.

(51) Int. Cl.
| | | |
|---|---|---|
| *A61K 31/522* | (2006.01) | |
| *A61P 25/28* | (2006.01) | |
| *A61P 31/04* | (2006.01) | |
| *A61P 35/00* | (2006.01) | |
| *A61K 31/63* | (2006.01) | |
| *A61K 31/7076* | (2006.01) | |
| *A61K 45/06* | (2006.01) | |
| *A61K 31/166* | (2006.01) | |
| *A61K 31/282* | (2006.01) | |
| *A61K 31/285* | (2006.01) | |
| *A61K 31/337* | (2006.01) | |
| *A61K 31/496* | (2006.01) | |
| *A61K 31/704* | (2006.01) | |

(52) U.S. Cl.
CPC ............ *A61K 31/522* (2013.01); *A61K 31/63* (2013.01); *A61K 45/06* (2013.01); *A61P 25/28* (2018.01); *A61P 31/04* (2018.01); *A61P 35/00* (2018.01); *A61K 31/166* (2013.01); *A61K 31/282* (2013.01); *A61K 31/285* (2013.01); *A61K 31/337* (2013.01); *A61K 31/496* (2013.01); *A61K 31/704* (2013.01); *A61K 31/7076* (2013.01)

(58) Field of Classification Search
CPC ................ A61K 31/522; A61K 31/704; A61K 31/7076; A61P 25/28; A61P 35/00
See application file for complete search history.

(56) References Cited

U.S. PATENT DOCUMENTS

| | | | |
|---|---|---|---|
| 8,883,500 B2 * | 11/2014 | Sitkovsky | .......... A61K 39/0011 435/375 |
| 2011/0064671 A1 | 3/2011 | Bynoe | |
| 2011/0262442 A1 | 10/2011 | Hamilton et al. | |
| 2013/0224110 A1 | 8/2013 | Bynoe | |

OTHER PUBLICATIONS

Kim et al., "A2A Adenosine Receptor Regulates the Human Blood-Brain Barrier Permeability," Mol Neurobiol 52:664-678 (2015).
Mlejnek et al., "P-Glycoprotein Mediates Resistance to A3 Adenosine Receptor Agonist 2-Chloro-N6-(3-Iodobenzyl)-Adenosine-5'-N-Methyluronamide in Human Leukemia Cells," Journal of Cellular Physiology 227:676-685 (2011).
Nakanishi et al, "Breast Cancer Resistance Protein (BCRP/ABCG2): Its Role in Multidrug Resistance and Regulation of Its Gene Expression," Chinese Journal of Cancer 31(2):73-99 (2012).
Eramo et al., "Chemotherapy Resistance of Glioblastoma Stem Cells," Cell Death and Differentiation 13:1238-1241 (2006).
Davis et al., "P-Glycoprotein Trafficking as a Therapeutic Target to Optimize CNS Drug Delivery," Advances in Pharmacology 71:25-44 (2014).
Rao et al., "A Study of the Pharmacokinetic Interaction of Istradefylline, A Novel Therapeutic for Parkinson's Disease, and Atorvastatin," J Clin Pharmacol 48:1092-1098 (2008).
Perez-Lloret et al., "Two New Adenosine Receptor Antagonists for the Treatment of Parkinson's Disease: Istradefylline Versus Tozadenant," Expert Opinion on Pharmacotherapy 15(8):1097-1107 (2014).
PCT International Search Report and Written Opinion for corresponding PCT/US2017/016555, dated Apr. 20, 2017.
Kim et al., "A2A Adenosine Receptor Modulates Drug Efflux Transporter P-Glycoprotein at the Blood-Brain Barrier," J. Clin. Invest. 126(5):1717-1733 (2016).

* cited by examiner

*Primary Examiner* — Sahar Javanmard
(74) *Attorney, Agent, or Firm* — Troutman Pepper Hamilton Sanders LLP (Rochester)

(57) ABSTRACT

The present invention relates to a method of inhibiting p-glycoprotein (P-gp) expression in a cell. The method involves contacting a cell expressing P-gp with a composition comprising an effective amount of an A2A adenosine receptor (A2A AR) agonist to inhibit P-gp expression in the cell. Methods of enhancing the bioavailability of a chemotherapeutic in a subject having multi-drug resistant (MDR) cancer and methods of increasing P-gp-mediated efflux in a cell are also disclosed.

19 Claims, 24 Drawing Sheets

A

B

C

D

A

B

USE OF ADENOSINE RECEPTOR SIGNALING TO REGULATE P-GP FUNCTION

This application is a national stage application under 35 U.S.C. § 371 of PCT International Application Serial No. PCT/US2017/016555, filed Feb. 3, 2017, which claims the benefit of U.S. Provisional Patent Application Ser. No. 62/290,763, filed Feb. 3, 2016, which is hereby incorporated by reference in its entirety.

This invention was made with government support under R01 NS063011 awarded by National Institutes of Health. The government has certain rights in the invention.

FIELD OF THE INVENTION

The present invention relates to the regulation of drug efflux transporter proteins.

BACKGROUND OF THE INVENTION

The brain is one of the most vascularized organs in the body. This high vascularity enables the efficient and constant supply of oxygen and nutrients from the peripheral circulation to the brain to maintain its proper function (Abbott N. J., "Astrocyte-Endothelial Interactions and Blood-Brain Barrier Permeability," *J. Anat.* 200(6):629-638 (2002) and Abbott et al., "Astrocyte-Endothelial Interactions at the Blood-Brain Barrier," *Nat. Rev. Neurosci.* 7(1):41-53 (2006)). The brain vasculature is lined by a single layer of specialized endothelial cells that provide a physical barrier against entry of unwanted substances from the circulation (Abbott N. J., "Blood-Brain Barrier Structure and Function and the Challenges for CNS Drug Delivery," *J. Inherit. Metab. Dis.* 36(3):437-449 (2013)). In addition, tight and adherens junction molecules seal the spaces between adjacent endothelial cells, generating even greater resistance (Ballabh et al., "The Blood-Brain Barrier: An Overview: Structure, Regulation, and Clinical Implications," *Neurobiol. Dis.* 16(1):1-13 (2004). This physical separation by endothelial cells and junction molecules forms the blood-brain barrier ("BBB"). Also, the BBB is insulated with extracellular matrix proteins, pericytes, and astrocytic endfeet processes, creating stability, insulation, and extremely high resistance. Together, these are referred to as the neurovascular unit ("NVU") (Abbott et al., "Astrocyte-Endothelial Interactions at the Blood-Brain Barrier," *Nat. Rev. Neurosci.* 7(1):41-53 (2006) and Deeken et al., "The Blood-Brain Barrier and Cancer: Transporters, Treatment, and Trojan Horses," *Clin. Cancer Res.* 13(6):1663-1674 (2007). In addition to providing a physical barrier, brain endothelial cells are equipped with efflux and influx transporters and receptors. These influx and efflux proteins are also expressed on astrocytic end-feet processes and thus selectively regulate the entry of substances into the brain (Deeken et al., "The Blood-Brain Barrier and Cancer: Transporters, Treatment, and Trojan Horses," *Clin. Cancer Res.* 13(6):1663-1674 (2007)). The high resistance of the BBB does not allow molecules larger than 450 Da to cross the BBB. This is critical to limiting entry of harmful substances, including infectious agents and toxins, into the brain and to maintaining the complex brain physiology and strict ionic environment (Abbott et al., "Astrocyte-Endothelial Interactions at the Blood-Brain Barrier," *Nat. Rev. Neurosci.* 7(1):41-53 (2006) and Abathuler R., "Approaches to Transport Therapeutic Drugs Across the Blood-Brain Barrier to Treat Brain Diseases," *Neurobiol. Dis.* 37(1):48-57 (2010)).

However, while the protection provided by the BBB is essential to the health of the host, it hampers the delivery of drugs into the brain to treat neurological disorders such as Alzheimer's disease ("AD") or primary brain cancers (Abbott N. J., "Blood-Brain Barrier Structure and Function and the Challenges for CNS Drug Delivery," *J. Inherit. Metab. Dis.* 36(3):437-449 (2013) and Ballabh et al., "The Blood-Brain Barrier: An Overview: Structure, Regulation, and Clinical Implications," *Neurobiol. Dis.* 16(1):1-13 (2004)). Many available drugs with the potential to treat these diseases are not effectively delivered to the brain due to the physical hindrance and efflux transporters imposed by the BBB. There have been numerous attempts to overcome the hindrance of drug delivery by the BBB that include physical disruption of the BBB, drug modification for easier passage across the BBB, and intrathecal injection of drugs into the brain (Neuwelt et al., "Osmotic Blood-Brain Barrier Disruption. Computerized Tomographic Monitoring of Chemotherapeutic Agent Delivery," *J. Clin. Invest.* 64(2):684-688 (1979); Elliott et al., "Intravenous RMP-7 Selectively Increases Uptake of Carboplatin into Rat Brain Tumors," *Cancer Res.* 56(17):3998-4005 (1996); Pardridge W. M., "Drug Transport Across the Blood-Brain Barrier," *J. Cereb. Blood Flow Metab.* 32(11):1959-1972 (2012); and Cook et al., "Intracerebroventricular Administration of Drugs," *Pharmacotherapy* 29(7):832-845 (2009)). However, these approaches have suffered from shortcomings, including toxicity, decreased drug efficacy, and invasiveness, that can result in permanent brain damage.

Cells and soluble factors cross the BBB through the paracellular or transcellular pathways (Daneman et al., "The Blood-Brain Barrier," *Cold Spring Harb. Perspect. Biol.* 7(1): a020412 (2015) and Abbott N. J., "Astrocyte-Endothelial Interactions and Blood-Brain Barrier Permeability," *J. Anat.* 200(6):629-638 (2002)). Passage across the paracellular pathway disrupts cell-to-cell junction to permit access to the brain. On the other hand, the transcellular pathway is mediated through transporters highly expressed on the luminal side of brain endothelial cells that allow for selective entry of molecules into the brain while maintaining normal brain physiology (Abbott N. J., "Astrocyte-Endothelial Interactions and Blood-Brain Barrier Permeability," *J. Anat.* 200(6):629-638 (2002) and Pascual et al., "GLUT1 Deficiency and Other Glucose Transporter Diseases," *Eur. J. Endocrinol.* 150(5):627-633 (2004)). However, multidrug-resistant ("MDR") transporters, especially drug efflux transporters, are highly expressed on brain endothelial cells and hinder the effective delivery of drugs into the Central Nervous System ("CNS"), including P-glycoprotein ("P-gp") and breast cancer-resistant protein 1 (BCRP1/ABCG2) (Abbott N. J., "Blood-Brain Barrier Structure and Function and the Challenges for CNS Drug Delivery," *J. Inherit. Metab. Dis.* 36(3):437-449 (2013); Pardridge W. M., "Drug Transport Across the Blood-Brain Barrier," *J. Cereb. Blood Flow Metab.* 32(11):1959-1972 (2012); Pardridge W. M., "The Blood-Brain Barrier: Bottleneck in Brain Drug Development," *NeuroRx* 2(1):3-14 (2005)). The most widely known and studied drug transporter expressed on brain endothelial cells is P-gp. (Begley D. J., "ABC Transporters and the Blood-Brain Barrier," *Curr. Pharm. Des.* 10(12): 1295-1312 (2004) and Beaulieu et al., "P-Glycoprotein Is Strongly Expressed in the Luminal Membranes of the Endothelium of Blood Vessels in the Brain," *Biochem. J.* 326(pt 2):539-544 (1997)). P-gp was the first MDR human transporter to be identified. It was first observed and described in drug-resistant cancer cells that highly expressed it. In breast cancer cells, P-gp prevents effective chemotherapeutic treatment by blocking chemo-therapeutic drug uptake (Chung et al., "P-Glycoprotein: The Intermediate End Point of Drug Response to Induction Chemotherapy in Locally Advanced Breast Cancer," *Breast Cancer Res. Treat.* 42(1):65-72 (1997); Filipits et al., "Immunocytochemical Detection of the Multidrug Resistance-Associated Protein and P-Glycoprotein in Acute Myeloid Leukemia: Impact of Antibodies, Sample Source and Disease Status," *Leukemia* 11(7):1073-1077 (1997); and Oda et al., "Expression of MDR1/P-Glycoprotein and Multidrug Resistance-Associated Protein in Childhood Solid Tumours," *Virchows Arch.* 430(2):99-105 (1997)). Later studies showed that P-gp is also highly expressed on capillaries of the liver, sex organs, and the brain and is involved in expulsion of xenobiotics from the CNS (Hebert M. F., "Contributions of Hepatic and Intestinal Metabolism and P-Glycoprotein to Cyclosporine and Tacrolimus Oral Drug Delivery," *Adv. Drug Deliv. Rev.* 27(2-3):201-214 (1997); Kusuhara et al., "P-Glycoprotein Mediates the Efflux of Quinidine Across the Blood-Brain Barrier," *J. Pharmacol. Exp. Ther.* 283(2): 574-580 (1997); Schinkel A. H., "P-Glycoprotein, A Gatekeeper in the Blood-Brain Barrier," *Adv. Drug Deliv. Rev.* 36(2-3):179-194 (1999); and Yang et al., "Progesterone Interacts With P-Glycoprotein in Multidrug-Resistant Cells and in the Endometrium of Gravid Uterus," *J. Biol. Chem.* 264(2):782-788 (1989)). P-gp is composed of 2 ATP-binding cassettes ("ABC") and 2 transmembrane domains. The drug-binding pocket of P-gp is nonspecific, and this allows for a broad spectrum of drugs as substrates (Gottesman et al., "The Molecular Basis of Multidrug Resistance in Cancer: The Early Years of P-Glycoprotein Research," *FEBS Lett.* 580(4):998-1009 (2006); Gottesman et al., "Structure of a Multidrug Transporter," *Nat. Biotechnol.* 27(6):546-547 (2009); and Aller et al., "Structure of P-Glycoprotein Reveals a Molecular Basis for Poly-Specific Drug Binding," *Science* 323(5922):1718-1722 (2009)). Recent studies suggest that substrates that are bound to the binding pocket of P-gp and are expelled into the extracellular space undergo conformational changes upon consumption of ATP as an energy source (Aller et al., "Structure of P-Glycoprotein Reveals a Molecular Basis for Poly-Specific Drug Binding," *Science* 323(5922):1718-1722 (2009)). Inhibitors of P-gp are widely used in preclinical and clinical studies for overcoming MDR. Valspodar (i.e., PSC833) is a functional inhibitor that binds directly to the drug-binding pocket of P-gp, thereby allowing entry of P-gp substrates into the cell (Horton et al., "Characterization of a Novel Bisacridone and Comparison With PSC833 as a Potent and Poorly Reversible Modulator of P-Glycoprotein," *Mol. Pharmacol.* 52(6):948-957 (1997) and Mayer et al., "Full Blockade of Intestinal P-Glycoprotein and Extensive Inhibition of Blood-Brain Barrier P-Glycoprotein by Oral Treatment of Mice With PSC833," *J. Clin. Invest.* 100(10):2430-2436 (1997)). Previous studies also proposed a possible role for P-gp in processing of intracellular cholesterol and transport of cytokines, steroid metabolites, and lipids to the extracellular space (Gottesman et al., "The Molecular Basis of Multidrug Resistance in Cancer: The Early Years of P-Glycoprotein Research," *FEBS Lett.* 580(4):998-1009 (2006); Rao et al., "Antiestrogens and Steroid Hormones: Substrates of the Human P-Glycoprotein," *Biochem. Pharmacol.* 48(2):287-292 (1994); and Pawlik et al., "Involvement of P-Glycoprotein in the Release of Cytokines From Peripheral Blood Mononuclear Cells Treated With Methotrexate and Dexamethasone," *J. Pharm. Pharmacol.* 57(11):1421-1425 (2005)). P-gp is mostly localized on cell membranes in drug-resistant cancer cells, whereas it is mostly localized in the cytoplasm, including Golgi apparatus, lysosome, mitochondria, and endosomes, in non-drug-resistant cancer cells (Paterson et al., "P-Glycoprotein Is Not Present in Mitochondrial Membranes," *Exp. Cell Res.* 313(14):3100-3105 (2007); Shen et al., "Mitochondrial Localization of P-Glycoprotein in the Human Breast Cancer Cell Line MCF-7/ADM and Its Functional Characterization," *Oncol. Rep.* 27(5):1535-1540 (2012); Yamagishi et al., "P-Glycoprotein Mediates Drug Resistance Via a Novel Mechanism Involving Lysosomal Sequestration," *J. Biol. Chem.* 288(44):31761-31771 (2013); and Fu et al., "Actin Disruption Inhibits Endosomal Traffic of P-Glycoprotein-EGFP and Resistance to Daunorubicin Accumulation," *Am. J. Physiol. Cell Physiol.* 292(4):C1543-C1552 (2007)). It is also suggested that P-gp actively circulates between organelles in the cell via the endocytic pathway (Fu et al., "Actin Disruption Inhibits Endosomal Traffic of P-Glycoprotein-EGFP and Resistance to Daunorubicin Accumulation," *Am. J. Physiol. Cell Physiol.* 292(4):C1543-C1552 (2007)). BCRP1 is another MDR transporter with an ABC that is expressed in the gut, BBB, placenta, and testis. Its expression in cancer cells indicates poor prognosis, which is believed to be caused by its regulation by multiple mechanisms of drug resistance (Staud et al., "Breast Cancer Resistance Protein (BCRP/ABCG2)," *Int. J. Biochem. Cell Bio.* 37(4):720-725 (2005)).

In brain endothelial cells, P-gp is localized in lipid raft, more specifically, in caveolae. Caveolae are specialized membrane (lipid) rafts that contain the caveolin protein and are characterized as flask-like invaginations of the plasma membrane. Caveolae-mediated endocytosis has been shown to facilitate the transport of molecules to other parts of the cell (Insel et al., "Membrane Rafts and Caveolae in Cardiovascular Signaling," *Curr. Opin. Nephrol. Hypertens.* 18(1):50-56 (2009)). An important characteristic of caveolae is detergent insolubility, which can be exploited for fractionation and enrichment (Bastiani et al., "Caveolae at a Glance," *J. Cell. Sci.* 123(22):3831-3836 (2010); Lajoie et al., "Lipid Rafts, Caveolae, and Their Endocytosis," in INTERNATIONAL REVIEW OF CELL AND MOLECULAR BIOLOGY, Vol. 282: 135-163 (Jeon & Galluzzi eds., 2010); Zhu et al., "Caveolin-1 and Doxorubicin-Induced P-Glycoprotein Modulate Plasma Cholesterol Membrane Accessibility in Erythrolymphoblastic Cell Line," *Anticancer Res.* 30(9):3451-3458 (2010); and Tome et al., "Identification of P-Glycoprotein Co-Fractionating Proteins and Specific Binding Partners in Rat Brain Microvessels," *J. Neurochem.* 134(2):200-210 (2015)). However, whether P-gp constantly circulates in cells and is recruited to the cell membrane upon its encounter with its substrate in the cytoplasm or persists on the cell membrane and pumps out its substrates into the extracellular space is not clearly proven. In a recent report, mitomycin C treatment induced the translocation of the cytoplasmic portion of P-gp to the cell surface, suggesting that relocalization of P-gp can be induced by chemical triggers (Noack et al., "Drug-Induced Trafficking of P-Glycoprotein in Human Brain Capillary Endothelial Cells as Demonstrated by Exposure to Mitomycin C," *PLoS One* 9(2):e88154 (2014)). Many drugs developed for treatment of brain disorders are largely classified as P-gp substrates; thus, significant efforts are placed on developing methods to bypass the hindrance posed by P-gp (Horton et al., "Characterization of a Novel Bisacridone and Comparison With PSC833 as a Potent and Poorly Reversible Modulator of P-Glycoprotein," *Mol. Pharmacol.* 52(6):948-957 (1997); Jette et al., "P-Glycoprotein Is a Dimer in the Kidney and Brain Capillary Membranes: Effect of Cyclosporin A and SDZ-PSC833," *Biochemistry* 36(45):13929-13937 (1997); and van Asperen et al., "Enhanced Oral Bioavailability of Paclitaxel in Mice Treated With the P-Glycoprotein Blocker SDZ PSC833," *Br. J. Cancer* 76(9):1181-1183 (1997)). However, control of drug efflux continues to be a significant hurdle in the development of therapeutics and treatment of disease.

The present invention is directed to overcoming these and other deficiencies in the art.

SUMMARY OF THE INVENTION

A first aspect of the present invention relates to a method of inhibiting P-glycoprotein ("P-gp") expression in a cell. The method involves contacting a cell expressing P-gp with a composition comprising an effective amount of an A2A adenosine receptor ("A2A AR") agonist to inhibit P-gp expression in the cell.

A second aspect of the invention relates to a method of enhancing bioavailability of a chemotherapeutic in a subject having multi-drug resistant ("MDR") cancer. The method involves selecting a subject having MDR cancer and administering to the selected subject an effective amount of an A2A adenosine receptor ("A2A AR") agonist to enhance intracellular delivery of a cancer therapeutic in the subject.

A third aspect of the invention relates to a method of increasing P-gp-mediated efflux in a cell. The method involves contacting a cell with an A2A AR antagonist in an amount sufficient to increase P-gp-mediated efflux.

The Examples of the present application demonstrate, inter alia, that activation of A2A AR signaling exerts its effects on the transcellular pathway by way of P-glycoprotein ("P-gp") modulation. In particular, the FDA-approved A2A AR agonist Lexiscan® and the broad-spectrum AR agonist NECA were used to determine the impact of A2A AR activation on P-gp expression and function. Activation of the A2A AR by Lexiscan® or NECA down-modulated the expression level of P-gp in primary mouse and human brain endothelial cells, which coincided with an increased accumulation of the classical P-gp substrate Rhodamine 123 ("Rho123"). Further, A2A AR activation by Lexiscan® rapidly increased accumulation of the chemotherapeutic drug and P-gp substrate epirubicin in the mouse brain. NECA also increased the accumulation of epirubicin at later time points compared with Lexiscan®. Similar to P-gp, it was found that Lexiscan® potently down-modulated the expression of Breast Cancer Resistance Protein 1 ("BCRP1"), whereas NECA's effect was less potent. These data indicate that A2A AR signaling potently increases the transcellular permeability of BBB endothelial cells.

These are significant findings and mark a major step forward in the control of, among other things, drug delivery and bioavailability. These findings also have significant implications for use of adenosine receptors to increase P-gp-mediated efflux in the treatment of disease, e.g., drug intoxication or Alzheimer's disease, where subjects benefit from cellular efflux of disease mediators.

BRIEF DESCRIPTION OF THE DRAWINGS

FIG. 1A is a fluorescence microscopy image showing that P-gp (green) is expressed in the cytoplasm of a human brain endothelial cell line, HCMEC-D3 (top panels), and in human primary brain endothelial cell, HBMVEC (middle and bottom panels). HCMEC-D3 (top panels) were counterstained with WGA (red) to depict cell membrane. HBMVEC were stained with an antibody to caveolin-1 (middle panels) (red) or antibody to CD31 (bottom panels) (red) as markers for caveolae and cell membrane, respectively. Nucleus was counterstained with DAPI (blue). The scale bars indicate 25 μm. FIG. 1B shows representative enlarged images from the inset in A of HBMVEC cells. The scale bar indicates 10 μm. FIG. 1C is a western blot image showing that P-gp was pulled down (immunoprecipitated) using anti-P-gp antibody and immunoblotted ("IB") with an anti-caveolin-1 antibody. FIG. 1D is a fluorescence microscopy image of HBMVEC cells treated with Rho123 (green, top panel) for 1 hour, then fixed and stained with anti-P-gp (red in top panel or green in bottom panel). Caveolae were counterstained with anti-caveolin-1 (green, bottom panel). The scale bar indicates 25 μm. FIG. 1E shows enlarged images from inset in FIG. 1D depicting P-gp or caveolae colocalization. The scale bar indicates 10 μm. FIGS. 1F-1G are graphs showing experimental results that demonstrate the inhibition of P-gp with PSC833, a functional inhibitor of P-gp in Rho123 uptake in human brain endothelial cell line HCMEC-D3 (FIG. 1F) and primary human brain endothelial cells (FIG. 1G). **$P<0.01$ ($n=3$, 2-tailed Student's t test, 1 representative result from 3 different experiments).

FIG. 2A shows primary mouse brain endothelial cells isolated and cultured on coverslips until they reached confluency. Cells were fixed with 4% PFA and permeabilized and stained with anti-Caveolin (red, top panel), anti-P-gP (green), or anti-CD31 (red, bottom panel). The scale bar indicates 50 μm. FIG. 2B shows magnified images of the boxed region from FIG. 2A. The scale bar indicates 10 μm.

FIG. 3A shows the results of a western blot of P-gp expression in primary brain endothelial cells treated with Lexiscan® (1 μM) up to 72 hours. GAPDH was used as a loading control. FIG. 3B shows the signal intensity of P-gp from the western blot shown in FIG. 3A divided by the signal intensity of GAPDH in the same western blot, for each time point. FIG. 3C shows the results of a western blot of P-gp expression on primary brain endothelial cells treated with NECA (1 μM) for up to 72 hours. GAPDH was used as a loading control. FIG. 3D shows the signal intensity of P-gp from the western blot shown in FIG. 3C divided by the signal intensity of GAPDH in the same western blot, for each time point. Short time points (up to 4 hours) are plotted separately and depicted as an inset.

FIG. 4A is a western blot of P-gp expression in HCMEC-D3 cells treated with Lexiscan® ("LEX") (1 μM) for up to 72 hours. GAPDH was used as loading control. FIG. 4B shows densitometric analysis of the western blot in FIG. 4A. The intensity of P-gp upon Lexiscan® treatment was divided by that of DMSO control. Densitometric analysis of short-time points (dotted box) is depicted as an inset. FIG. 4C shows the results of a Rho123 uptake assay of HCMEC-D3 cells treated with Lexiscan® (1 μM). Concentrations of Rho123 accumulation in brain endothelial cells were analyzed by fluorometry (Synergy, Biotek), with excitation at 488 nm and emission at 523 nm. *$P<0.05$; **$P<0.01$ ($n=4$, 2-tailed Student's t test, 1 representative result of 3 different experiments). FIG. 4D is a western blot depicting P-gp expression in human primary brain endothelial cells treated with Lexiscan® (1 µM) for up to 72 hours. GAPDH was used as loading control. FIG. 4E shows densitometric analysis of the signal intensity of P-gp expression with Lexiscan® or NECA treatment divided by the signal intensity of the DMSO control in FIG. 4D. Densitometric analysis of short-time point (dotted box) is depicted as an inset. FIG. 4F summarizes the experimental results of a Rho123 uptake assay of human primary brain endothelial cells treated with Lexiscan® (1 µM). The concentration of Rho123 accumulation in endothelial cells was quantified by fluorometry (Synergy, Biotek), with excitation at 488 nm and emission at 523 nm. *P<0.05; **P<0.01 (n=4, 2-tailed Student's t test, 1 representative result of 3 different experiments). FIG. 4G is a schematic diagram of the Rho123 accumulation assay from FIGS. 4C and 4F.

FIG. 5A is a western blot of P-gp expression in HCMEC-D3 cells treated with NECA (1 µM) for up to 72 hours. GAPDH was used as a loading control. FIG. 5B is a densitometric analysis of the western blot in FIG. 5A. The intensity of P-gp with NECA treatment was divided by that of DMSO control. Densitometric analysis of the short-time point (dotted box) is depicted as an inset (smaller graph). FIG. 5C summarizes the results of a Rho uptake assay of HCMEC-D3 cells treated with NECA (1 µM) for up to 90 minutes. The concentration of Rho123 accumulation in brain endothelial cells was analyzed by Fluorometry with excitation at 488 nm and emission at 523 nm. *, ** indicates P<0.05 and P<0.01, respectively (n=4, two tailed student t-test, one representative result from three different experiments). FIG. 5D is a western blot depicting P-gp expression in human primary brain endothelial cells after treatment with NECA (1 µM) for up to 72 hours. GAPDH was used as a loading control. FIG. 5E is a densitometric analysis of FIG. 5D. The intensity of P-gp with NECA treatment was divided by that of DMSO control. The inset in FIG. 5E is a densitometric analysis of short-time points (dotted box). FIG. 5F is a Rho uptake assay of human primary brain endothelial cells treated with NECA (1 µM). The concentration of Rho123 accumulation in endothelial cells was quantified by fluorometry with excitation at 488 nm and emission at 523 nm. *, ** indicates P<0.05 and P<0.01, respectively (n=4, two tailed student t-test, one representative result from three different experiments).

FIG. 6A is a schematic diagram depicting the methodology of the transmigration assay of Rho123 using an in vitro BBB model. FIG. 6B is a graph of experimental results obtained using the in vitro BBB model of FIG. 6A and primary human brain endothelial cell monolayers cultured on porous membranes to determine Rho123 migration across the BBB. Endothelial cell monolayers cultured on porous membranes were treated with Lexiscan® (0.25 µM) or NECA (0.25 µM) concomitantly with 2.5 µM of Rho123, and the concentration of Rho123 at the bottom chambers was analyzed by fluorimetry, with excitation at 488 nm and emission at 523 nm. *P<0.05 (n=4, 2-tailed Student's t test, 1 representative result of 3 different experiments). FIGS. 6C-6F are fluorescence microscopy images showing human primary brain endothelial cells cultured on coverslips and treated with 2.5 µM of Rho123 with or without 1 µM of Lexiscan® or NECA at different time points: 15 minutes (FIG. 6C), 1 hour (FIG. 6D), 4 hours (FIG. 6E), and 24 hours (FIG. 6F). Cells were fixed with 4% PFA and costained with P-gp and visualized with a fluorescent microscope. The scale bar indicates 25 µm.

FIG. 8A is a schematic diagram of the experimental procedure for analysis of Lexiscan®'s effect on P-gp solubility and excretion in primary brain endothelial cells ("HBMVEC"). FIGS. 8B-8C are western blots and graphs summarizing the experimental result of each western blot. FIGS. 8B-8C show the analysis of P-gp expression of HBMVEC upon activation with Lexiscan® at different time points after lysis with RIPA buffer (FIG. 8B) or CSK buffer to measure P-gp levels in the cytoskeletal fraction (FIG. 8C). Band intensity was normalized to GAPDH and graphed. FIG. 8D shows analysis of MMP9 in HBMVEC upon activation with Lexiscan® at different time points. Band intensity was normalized using GAPDH and plotted. FIG. 8E is a western blot of secreted P-gp in HBMVEC upon activation with Lexiscan® in absence or presence of an MMP9 inhibitor: both short and long exposures of western blot from MMP9 inhibitor-treated samples are shown. Band intensity was plotted as a graph. FIG. 8F is a western blot showing the results of an Immunoprecipitation assay of MMP9 with lysate from HBMVEC treated with vehicle (control) or 1 µM of Lexiscan® for 5 minutes. P-gp was pulled down using anti-P-gp antibody and immunoblotted with an anti-MMP9 antibody. FIG. 8G is an immunofluorescence microscopy image of MMP9 on HBMVEC treated with control (top panel) or 1 µM of Lexiscan® (middle panel) for 5 minutes. Cells were stained with P-gp (green) and MMP9 (red). Nucleus was counterstained with DAPI (blue). Boxed region (inset) of Lexiscan®-treated sample was magnified and displayed separately (bottom panel). Cell-surface colocalization of P-gp and MMP9 is indicated by arrows. The scale bars indicates 25 µm (upper and middle panels); 5 µm (bottom panels). FIG. 8H is a graph summarizing the intensity of fluorescence of MMP9 from FIG. 8G. Fluorescent intensity of MMP9 was quantified and plotted as graph (n=20). **P<0.01 (2-tailed Student's t test, 1 representative result of 3 different experiments).

FIG. 10A is a western blot showing immunoprecipitation analysis of ubiquitination of P-gp in human primary brain endothelial cells upon activation with Lexiscan® for 15 minutes. P-gp was pulled down with an anti-P-gp antibody and immunoblotted with an anti-ubiquitin antibody. FIG. 10B are immunofluorescence microscopy images depicting ubiquitination of P-gp in human primary brain endothelial cells upon activation with Lexiscan® for 15 minutes. Cells were fixed, permeabilized, and stained with an anti-P-gp (green) and anti-ubiquitin (red) antibody. Nucleus was counterstained with DAPI (blue). The scale bar indicates 25 µm. FIG. 10C is a schematic diagram depicting the mechanism of P-gp down-regulation by Lexiscan®. Upon activation of A2A AR, P-gp is cleaved by MMP9 and secreted to the extracellular space (a), or ubiquitinated and digested by proteasome (b), or can relocate from the soluble fraction to the insoluble fraction (c). These mechanisms may occur independently or in combination.

FIG. 11A is a western blot and graphic summarizing the results of the western blot showing the presence of P-gp in primary brain endothelial cell lysates of brains of WT, A1, A2A, and CD73 KO mice. β-Actin was used as a loading control. Intensity of bands was normalized with that of β-actin. *$P<0.05$ (n=3 from 3 different western blots, 2-tailed Student's t test). FIG. 11B is a graph of the experimental results of a Rho123 uptake assay performed using primary brain endothelial cells from brains of WT, A1, A2A, and CD73 KO mice. Cells were grown to confluence and treated with 2.5 µM of Rho123 at 5, 15, 30, and 60 minutes. Cells were lysed with lysis buffer and were analyzed by fluorometry, with excitation at 488 nm and emission at 523 nm. *$P<0.05$; **$P<0.01$ (n=4, 2-tailed Student's t test, 1 representative result of 2 different experiments). FIG. 11C is an image of a western blot of P-gp expression levels from brains of WT, A1 KO, A2A KO, and CD73 KO mice. β-Actin was used as loading control. Band intensity was normalized to that of β-actin and graphed. *$P<0.05$ (n=3, 2-tailed Student's t test). FIG. 11D includes fluorescence microscopy images showing the results of immunofluorescence analysis ("IFA") on the brain of WT, A1 KO, A2A KO, and CD73 KO mice. Frozen brain sections were stained with GLUT1 (an endothelial marker, red) and P-gp (green) and counterstained with DAPI (blue). Nucleus was counterstained with DAPI (blue). The scale bar indicates 100 µm.

FIG. 12A is a fluorescence microscopy image showing immunofluorescence images of brains from Lexiscan®-treated mice of WT brain at 15 and 30 minutes after Lexiscan® treatment. Frozen brain sections were stained with GLUT1 (red), or P-gp (green) and counterstained with DAPI (blue). FIG. 12B is a fluorescence microscopy image showing an enlarged image of FIG. 12A. FIG. 12C is a graph summarizing the experimental results of a brain epirubicin accumulation assay in the Lexiscan®- and vehicle-treated (control) mice. Briefly, 10 mg/kg of epirubicin was injected intravenously with or without 0.05 mg/kg of Lexiscan®. Mice were perfused with ice-cold PBS and sacrificed at different time points. The accumulation of epirubicin in the brain was measured using fluorometric excitation at 488 nm and emission at 590 nm. *$P<0.05$ (n=4, 2-tailed Student's t test). FIG. 12D are fluorescence microscopy images showing fluorescent microscopic analysis of epirubicin accumulation in the brains of mice treated with Lexiscan® or PSC833 (a functional P-gp inhibitor) compared with vehicle (control). 10 mg/kg of epirubicin was injected intravenously with or without 0.05 mg/kg of Lexiscan® or 50 mg/kg of PSC833 for 15 minutes. Mice were perfused with ice-cold PBS and sacrificed. Brain was sectioned for microscopic analysis for full-brain image, and focal zoomed image from cortex was laid as an inset. Epirubicin is in red, and nucleus was counterstained with DAPI (blue). FIG. 12E are graphs showing the quantified intensity of epirubicin from different regions of cortex (CTX), cerebellum (CRBL), and hippocampus (HPC) from brains of control, Lexiscan®-, or PSC833-injected animals and depicted as graphs. The scale bars indicate 100 µm in FIG. 12A; 50 µm in FIG. 12B, and 5 mm in FIG. 12D). ***$P<0.001$ (n=50, 2-tailed Student's t test).

FIG. 13A is a western blot and graph summarizing the results of the western blot of P-gp and BCRP1 expression in brains of Lexiscan® treated WT mice for 5 and 15 minutes. GAPDH was used as loading control. Densitometric analyses of P-gp and BCRP1 expression were normalized using GAPDH and depicted as a graph (right). Intensity of bands from Lexiscan® treated mice brains were divided by that of DMSO control brains. Each dot indicates each replicate at different time points. FIG. 13B is a western blot and graph summarizing the results of the western blot of P-gp and BCRP1 expression in brains of Lexiscan® treated WT mice for 30 and 60 minutes. GAPDH was used as loading control. Densitometric analysis of P-gp and BCRP1 expression level normalized by GAPDH was depicted as a graph (right). Intensity of bands from Lexiscan® treated brains were divided by that of DMSO control brains. Each dot indicates each replicate at different time points. FIG. 13C is a graph of experimental results showing the combined time course of Lexiscan® treatment and measurement of P-gp and BCRP1 gene expression.

FIG. 14A is a western blot of P-gp and BCRP1 from mouse brain at 2 and 18 hours after NECA treatment. FIG. 14B are graphs showing the enumeration of the expression intensity of P-gp and BCRP1 from the western blots shown in FIG. 14A. The intensity of the bands from NECA treatment group was divided by that of DMSO control. Acquired values were normalized by GAPDH and graphed. The graphs show the relative band intensity of P-gp and BCRP at 2 hours (left graph) and 18 hours (right graph) following treatment with NECA. *$P<0.05$ (n=3, 2-tailed Student's t test). FIG. 14C shows fluorescence microscopy images of P-gp in NECA-treated mouse brain at 2 and 18 hours after treatment. For fluorescence microscopy, frozen brain sections were stained with GLUT1 (red) or P-gp (green) and counterstained with DAPI (blue). The scale bar indicates 100 µm. FIG. 14D is a graph of experimental results of epirubicin brain accumulation assays in NECA-treated mice. 0.08 mg/kg of NECA was injected intravenously for the indicated times and, subsequently, 10 mg/kg of epirubicin was intravenously injected. At 15 minutes after epirubicin treatment, mice were perfused with ice-cold PBS and sacrificed at different time points. The accumulation of epirubicin in the brain was measured using fluorometry, with excitation at 488 nm and emission at 590 nm. *P<0.05 (n=4, 2-tailed Student's t test).

FIG. 16A is a western blot of MCF7, MDA-MB-231 and HS578t cell lysates. Cells were grown to confluency, lysed using lysis buffer, and analyzed by western blot using AR-specific antibodies. GAPDH was used as a loading control. HS578t cells appear to express less A2A AR as compared to the MCF7 and MDA-MB-231 cell lines. Applicants note that HS578t cells express high levels of A2AR. However, the relative expression level of the A1AR as compared to the A2AR in this cell line is extremely high. Therefore, to avoid overexposure, the western blot of HS578t cell lysates was exposed for a shorter duration than that of the MCF7 and MDA-MB-231 cell lysates. FIG. 16B is a graph of the densitometric analysis of AR expression levels normalized by GAPDH for MCF7 cell lysates shown in FIG. 16A.

FIGS. 17A-17C are images of western blots of cells treated with vehicle control (i.e., DMSO) ("D") or 1 µM of the broad spectrum AR agonist NECA ("N") (FIG. 17A), 1 µM of the A2A AR agonist Lexiscan® ("L") (FIG. 17B), or 1 µM of the A2B AR agonist BAY60 ("B") (FIG. 17C), respectively for 24, 48, 72 hours. Cells were lysed with lysis buffer and expression levels of P-gp, MMP9, or VEGF analyzed by western blot. GAPDH was used as loading a control. FIG. 17D is a graph of experimental results showing that Lexiscan® down-regulates P-gp expression in MCF7 breast cancer cells. MCF7 breast cancer cells were treated with Lex (0.25 µM) concomitant with Rhodamine 123 ("Rho123"). Significant Rho123 accumulation was observed in MCF7 cancer cells by 15 minutes and at 60 minutes compared to vehicle control that is consistent with P-gp downregulation by Lex. Students T test, P<0.001. FIGS. 17E-17F show that A1193 and Lexiscan® down-regulate P-gp expression and allow the uptake and accumulation of epirubicin in MCF7 cancer cells. FIG. 17E is a fluorescence microscopy image showing MCF7 breast cancer cells grown on coverslips and treated with vehicle (DMSO, control), or A2 AR agonists, Lexiscan® (1 µM) or A1193 (1 µM) for 15 minutes in the presence of epirubicin. Cells were stained with an antibody to P-gp and mounted with DAPI. FIG. 17F is a graph of the fluorescent intensity quantified from FIG. 17E by measuring the mean fluorescent intensity ("MFI") of epirubicin (pink) that is present in cell nuclei. ***=P<0.0001.

FIG. 18A are fluorescence microscopy images showing that Lexiscan® significantly decreases P-gp expression in intestinal organoids. FIG. 18B is a graph of the mean fluorescence intensity of P-gp shown in FIG. 18A. Freshly isolated intestines from wildtype C56BL6 mice were cultured and grown to confluency to generate Organoids, which are 3D organotypic cultures derived from primary intestinal tissues (either tissue subunits or single cells), embryonic stem cells ("ESCs"), and induced pluripotent stem cells ("iPSCs"). Organoids were treated with 1 µM Lexiscan® or A1193 (A2A AR agonist) for 15 minutes, washed, and stained with antibodies to P-gp and DAPI. Mean fluorescent intensity was measured in each organoid. Data presented as a measure of P-gp expression between the two agonists. *=significance where P<0.05.

FIG. 19A are fluorescence microscopy images of Caco-2 cells (originally isolated from a human primary colonic tumor) grown on coverslips and treated with Lexiscan® (1 µM) or A1193 (1 µM), or DMSO (vehicle) control for 30 minutes. Next, cells were fixed, permeabilized, and stained with an antibody to P-gp. After washing, cells were mounted with DAPI for nuclear staining. FIG. 19B is a graph of the MFI of P-gp. FIG. 19C is a graph of densitometric analysis of a western blot of Caco-2 cells treated with Lexiscan® in varying concentrations (1, 0.5, and 0.1 µM). Densitometric analysis was performed to quantify the amount of P-gp in western blot. Statistics: two tailed student's t test for FIG. 19B, *<0.5.

FIG. 20A shows fluorescence microscopy images of HEK293T cells. HEK293T cells were grown to confluency on coverslips, and treated with varying concentrations of Lexiscan® (1, 0.5, and 0.1 µM) for 15 minutes. Cells were permeabilized and then stained with an antibody to P-gp (C219) and visualized under a fluorescent microscope. FIG. 20B is a graph of the MFI of P-gp in FIG. 20A. DMSO vs. Lexiscan® ("Lex"), *=P<0.05, Lexiscan® ("Lex")+ SCH58261 ("SCH"), ****P<0.0001.

DETAILED DESCRIPTION OF THE INVENTION

Figures 1A, 1B, 1C, 1D, 1E, 1F, 1G:
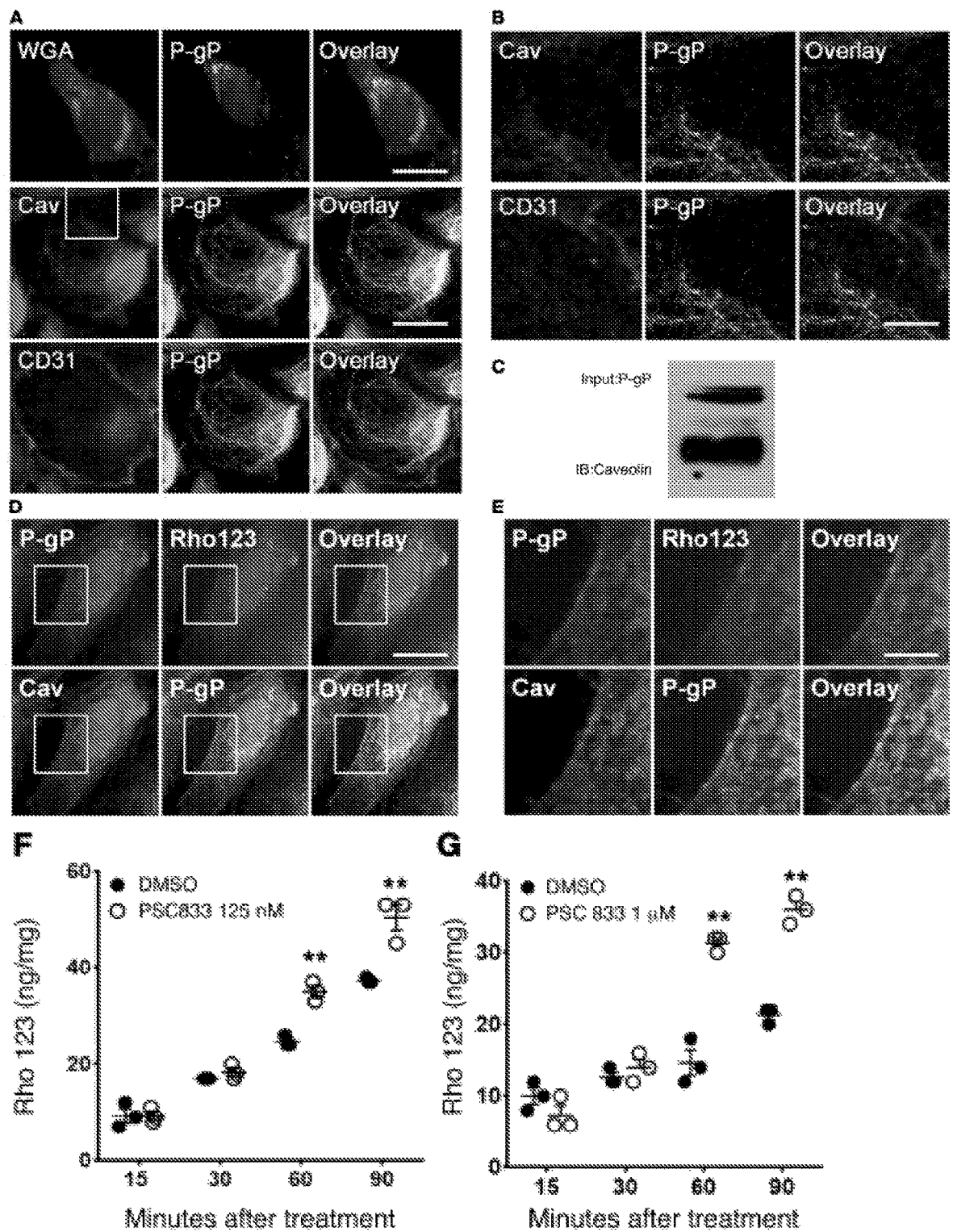
FIGS. 1A-1G show experimental results which demonstrate that P-gp is expressed mostly in the cytoplasm of human brain endothelial cells and is colocalized with caveolae.
Figures 2A, 2B:
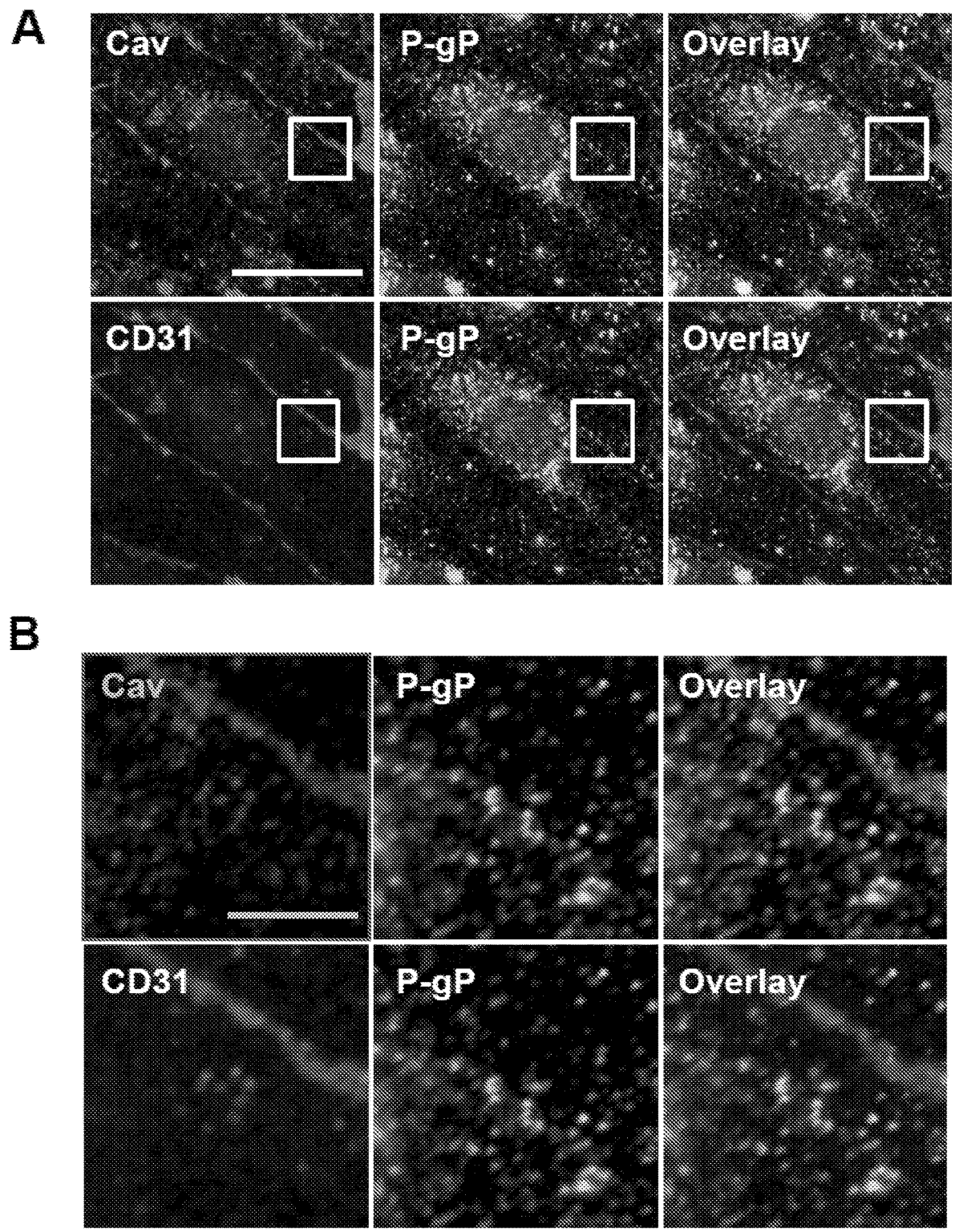
FIGS. 2A-2B are fluorescence microscopy images showing that P-gp is co-localized with Caveolin-1 in primary mouse brain endothelial cell.

One aspect of the present invention relates to a method of inhibiting P-glycoprotein ("P-gp") expression in a cell. The method involves contacting a cell expressing P-gp with a composition comprising an effective amount of an A2A adenosine receptor ("A2A AR") agonist to inhibit P-gp expression in the cell.

As used herein, the terms "P-glycoprotein," "P-gp," and "ABCB1" refer to an ATP-dependent efflux pump with broad substrate specificity. P-gp is a member of the B-class of the eukaryotic ATP binding cassette ("ABC") superfamily of transporters and plays a role in multiple drug resistance phenotypes by mediating ATP-dependent drug translocation across the plasma membrane against concentration gradients.

Adenosine is a cellular signal of metabolic distress being produced in hypoxic, ischemic, or inflammatory conditions. It functions to reduce tissue injury and promote repair by different receptor-mediated mechanisms, including the increase of oxygen supply/demand ratio, preconditioning, anti-inflammatory effects, and stimulation of angiogenesis (Jacobson et al., "Adenosine Receptors as Therapeutic Targets," Nat. Rev. Drug Discov. 5:247-264 (2006), which is hereby incorporated by reference in its entirety). The biological effects of adenosine are ultimately dictated by the different pattern of receptor distribution and/or affinity of the four known adenosine receptor ("AR") subtypes in specific cell types: A1, A2A, A2B, and A3 (Sebastiao et al., "Adenosine Receptors and the Central Nervous System," Handb. Exp. Pharmacol. 471-534 (2009), which is hereby incorporated by reference in its entirety).

Adenosine receptors are integral membrane proteins which bind extracellular adenosine, thereby initiating a transmembrane signal via specific guanine nucleotide binding proteins known as G-proteins to modulate a variety of second messenger systems, including adenylyl cyclase, potassium channels, calcium channels and phospholipase C (Stiles, "Adenosine Receptors and Beyond: Molecular Mechanisms of Physiological Regulation," Clin. Res. 38(1): 10-18 (1990); Stiles, "Adenosine Receptors," J. Biol. Chem. 267: 6451-6454 (1992), which are hereby incorporated by reference in their entirety). Activating the A2A AR or A2B AR also inhibits P-gp expression or P-gp activity in a cell.

In one embodiment, the A2A AR agonist is a broad spectrum agonist. As used herein, the term "agonist" refers to a compound, the presence of which results in the activation of receptor. An "adenosine receptor agonist" can bind to an adenosine receptor and initiate a physiological or a pharmacological response characteristic of that receptor.

As used herein the term "broad spectrum agonist" refers to a compound which does not have an activation preference for a specific receptor over another receptor. Activation preferences can be quantified based upon whole cell, tissue, or organism assays which demonstrate receptor activity. The term "broad spectrum agonist" may also refer to a compound that is able to bind to two or more receptors and promote their activation at similar concentrations (e.g., no greater than 5-fold, 4-fold, 3-fold, or 2-fold selectively) as compared to any other adenosine receptor. Various broad spectrum adenosine receptor agonists are well known in the art and include, for example, (2S,3S,4R,5R)-5-(6-aminopurin-9-yl)-N-ethyl-3,4-dihydroxyoxolane-2-carboxamide ("NECA" or "5'-(N-Ethylcarboxamido)adenosine"), (2R,3R,4S,5R)-2-(6-amino-2-chloropurin-9-yl)-5-(hydroxymethyl)oxolane-3,4-diol ("2-Chloroadenosine"), and 9-β-D-Ribofuranosyl-9H-purin-6-amine (adenosine). For instance, adenosine (a broad spectrum AR agonist) is a purine nucleoside that functions as an important local signaling molecule and is involved in various physiological functions, including neurotransmission, cardiac pace, and immune regulation (Hasko et al., "Adenosine Receptor Signaling in the Brain Immune System," Trends Pharmacol. Sci. 26(10):511-516 (2005); Hasko et al., "Adenosine Receptors: Therapeutic Aspects for Inflammatory and Immune Diseases," Nat. Rev. Drug Discov. 7(9):759-770 (2008); and Jacobson et al., "Adenosine Receptors as Therapeutic Targets," Nat. Rev. Drug Discov. 5(3):247-264 (2006), which are hereby incorporated by reference in their entirety).

In some embodiments, the A2A AR agonist is not a broad spectrum adenosine receptor agonist. In one embodiment, the A2A AR agonist is not NECA. In one embodiment, the A2A AR agonist is not adenosine.

In some embodiments, the A2A AR agonist is a selective agonist. As used herein, the term "selective agonist" refers a compound having an activation preference for a specific adenosine receptor over another adenosine receptor. The term "selective agonist" may also refer to a compound that is able to selectively bind to a specific adenosine receptor and promote its activation at significantly lower concentrations (e.g., greater than 10-fold, 20-fold, 50-fold, or 100-fold selectively) compared to any other adenosine receptor type. For example, an "A2A AR selective agonist" is one that selectively binds to the A2A receptor, promoting the activation of the A2A receptor over that of the A1 AR, A2B AR, and/or A3 AR. Exemplary A2A AR selective agonists include, for example, regadenoson (CVT-3146, Lexiscan®) and CGS 21680.

Suitable A2A AR agonists are well known in the art (Press et al., "Therapeutic Potential of Adenosine Receptor Antagonists and Agonists," Expert Opin. Ther. Pat. 17(8):1-16 (2007), which is hereby incorporated by reference in its entirety) and include those described in U.S. Pat. No. 6,232,297 and in U.S. Published Patent Application No. 2003/0186926 A1 to Lindin et al., 2005/0054605 A1 to Zablocki et al., and U.S. Published Patent Application Nos. 2006/0040888 A1, 2006/0040889 A1, 2006/0100169 A1, and 2008/0064653 A1 to Li et al., which are hereby incorporated by reference in their entirety. Such compounds may be synthesized as described in: U.S. Pat. Nos. 5,140,015 and 5,278,150 to Olsson et al.; U.S. Pat. No. 5,593,975 to Cristalli; U.S. Pat. No. 4,956,345 Miyasaka et al.; Hutchinson et al., "CGS 21680C, an A2 Selective Adenosine Receptor Agonist with Preferential Hypotensive Activity," J. Pharmacol. Exp. Ther., 251: 47-55 (1989); Olsson et al, "N6-Substituted N-alkyladenosine-5'-uronamides: Bifunctional Ligands Having Recognition Groups for A1 and A2 Adenosine Receptors," J. Med. Chem., 29: 1683-1689 (1986); Bridges et al., "N6-[2-(3,5-dimethoxyphenyl)-2-(2-methylphenyl)ethyl]adenosine and its Uronamide Derivatives: Novel Adenosine Agonists With Both High Affinity and High Selectivity for the Adenosine A2 Receptor," J. Med. Chem. 31: 1282 (1988); Hutchinson et al., J. Med. Chem., 33:1919 (1990); Ukeeda et al., "2-Alkoxyadenosines: Potent and Selective Agonists at the Coronary Artery A2 Adenosine Receptor," J. Med. Chem. 34: 1334 (1991); Francis et al., "Highly Selective Adenosine A2 Receptor Agonists in a Series of N-alkylated 2-aminoadenosines," J. Med. Chem. 34: 2570-2579 (1991); Yoneyama et al, "Vasodepressor Mechanisms of 2-(1-octynyl)-adenosine (YT-146), a Selective Adenosine A2 Receptor Agonist, Involve the Opening of Glibenclamide-sensitive K+ Channels," Eur. J. Pharmacol. 213(2):199-204 (1992); Peet et al., "Conformationally Restrained, Chiral (phenyl)sopropyl)amino-substituted pyrazolo[3,4-d]pyrimidines and Purines with Selectivity for Adenosine A1 and A2 Receptors," J. Med. Chem., 35: 3263-3269 (1992); and Cristalli et al., "2-Alkynyl Derivatives of Adenosine and Adenosine-5'-N-ethyluronamide as Selective Agonists at A2 Adenosine Receptors," J. Med. Chem. 35(13): 2363-2368 (1992), which are hereby incorporated by reference in their entirety. Additional examples of adenosine A2A receptor agonists are disclosed in U.S. Patent Application Publication 2004/0809916, which is hereby incorporated by reference in its entirety.

Additional exemplary A2A AR agonists include, without limitation, methyl 4-[3-[6-amino-9-[(2R,3R,4S,5S)-5-(ethylcarbamoyl)-3,4-dihydroxyoxolan-2-yl]purin-2-yl]prop-2-ynyl]cyclohexane-1-carboxylate ("apadenoson" or "ATL-146e"); (2R,3R,4S,5R)-2-[6-amino-2-[(2E)-2-(cyclohexylmethylidene)hydrazinyl]purin-9-yl]-5-(hydroxymethyl)oxolane-3,4-diol ("binodenoson"); 3-[4-[2-[[6-amino-9-[(2R,3R,4S,5S)-5-(ethylcarbamoyl)-3,4-dihydroxyoxolan-2-yl]purin-2-yl]amino]ethyl]phenyl]propanoic acid ("CGS 21680"); (2R,3R,4S,5R)-2-(6-amino- 2-oct-1-ynylpurin-9-yl)-5-(hydroxymethyl)oxolane-3,4-diol ("2-Octynyladenosine" or "YT-146"); $N^6$-[2-(3,5-Dimethoxyphenyl)-2-(2-methylphenyl)-ethyl]adenosine ("DPMA" or "PD-125,944"); (2R,3R,4S,5R)-2-(6-amino-2-anilinopurin-9-yl)-5-(hydroxymethyl)oxolane-3,4-diol ("2-Phenylaminoadenosine" or "CV 1808"); 2-Amino-4-(4-hydroxyphenyl)-6-[(1H-imidazol-2-ylmethyl)thio]-3,5-pyridinecarbonitrile ("LUF 5834"); 4-[2-[(6-Amino-9-b-D-ribofuranosyl-9H-purin-2-yl)thio]ethyl]benzenesulfonic acid ammonium salt ("PBS 0777 ammonium salt"); (2S,3S,4R,5R)-5-(6-aminopurin-9-yl)-N-ethyl-3,4-dihydroxyoxolane-2-carboxamide ("NECA"); 1-[6-amino-9-[(2R,3R,4S,5R)-3,4-dihydroxy-5-(hydroxymethyl)oxolan-2-yl]purin-2-yl]-N-methylpyrazole-4-carboxamide ("CVT-3146," "regadenoson," "Rapiscan," or "Lexiscan®"); and 6-(2,2-diphenylethylamino)-9-((2R,3R,4S,5S)-5-(ethylcarbamoyl)-3,4-dihydroxytetrahydrofuran-2-yl)-N-(2-(3-(1-(pyridin-2-yl)piperidin-4-yl)ureido)ethyl)-9H-purine-2-carboxamide ("A1193" or "UK-432097"). In some embodiments, the A2A AR agonist is a precursor or derivative of an A2A AR agonist Suitable A2A AR selective agonists include, for example, regadenoson, apadenoson, binodenoson, CGS 21680, YT-146, DPMA, PBS 0777 ammonium salt, and A1193.

As described herein, activation of the A2B adenosine receptor also modulates P-gp expression or function. Thus, also contemplated in addition to or as an alternative to the administration of an A2A AR agonist is that the administration of an A2B AR agonist as described herein will also decrease cellular P-gp expression or function.

Exemplary A2B AR agonists include, for example, 2-[[6-Amino-3,5-dicyano-4-[4-(cyclopropylmethoxy)phenyl]-2-pyridinyl]thio]-acetamide ("BAY 60-6583"), 2-Phenylaminoadenosine ("CV 1808"), and 2-Amino-4-(4-hydroxyphenyl)-6-[(1H-imidazol-2-ylmethyl)thio]-3,5-pyridinecarbonitrile ("LUF 5834"), NECA, and adenosine. BAY 60-6583 is a selective A2B AR agonist, CV 1808 is an A2 receptor agonist, and LUF 5834 is a potent A2A and A2B AR partial agonist.

In one embodiment, the cell contacted as described herein is of the intestine, pancreatic ductules, bile ductules, kidney, or adrenal gland. Suitable cells include, for example, epithelial cells of the colon, small intestine, bile ductiles, kidney proximal tubes, and adrenal gland.

In one embodiment, the cell contacted as described herein is a cardiac cell. Accordingly, suitable cardiac cells include, but are not limited to, endothelial cells of the capillaries and arterioles.

In some embodiments, the cell contacted as described herein is a gonad cell or a mammary cell. In accordance with this embodiment, suitable cells include, but are not limited to, cells of the ovaries and testes, breast cells, endothelial cells of the capillaries, the arterioles, the blood testes barrier, and the blood mammary tissue barrier, as well as secretory epithelial cells of the placenta and endometrium (Guofeng et al., "The P-Glycoprotein Gene Family" in *Drug Transporters: Molecular Characterization and Role in Drug Disposition*, Hoboken, N.J.: Wiley-Interscience (2007), which is hereby incorporated by reference in its entirety).

In some embodiments, the cell is a breast cell. In one embodiment, the cell is a breast epithelial cell. In one embodiment, the cell is a mammary cell. In some embodiments, the cell also expresses Breast Cancer Resistance Protein 1 (BCRP1) and the contacting is effective to inhibit BCRP1 expression in the cell.

In some embodiments, the cell is mammary cell is a ductal cell, a lobular cell, a muscle cell, a blood cell, or a fat cell.

As described herein, activation of the A2A AR or A2B AR may also modulate BCRP1 expression or function. Thus, also contemplated in addition to or as an alternative to the administration of an A2A AR or A2B AR agonist is that the administration of an A2A AR or A2B AR agonist as described herein will also decrease cellular BCRP1 expression or function.

The cell described herein may be a neoplastic cell. The neoplastic cell may have increased P-gp expression, as compared to a non-neoplastic cell. As used herein, the term "neoplastic cell" refers to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. In some embodiments, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

As described herein, in some embodiments, the cell is not a brain endothelial cell.

The methods of the present invention may be carried out in vitro, in vivo, or ex vivo. As used herein, the term "in vitro" refers to a process by which cells are cultured in an artificial environment (e.g., in a test tube, in a culture plate, in a bioreactor). The term "in vivo" refers to a process by which cells are cultured in their natural environment (e.g., in an animal or a cell) and to processes or reaction that occur within a natural environment. The term "ex-vivo" refers to a process by which cells are removed from a living organism and are cultured outside the organism (e.g., in a test tube, in a culture plate, in a bioreactor).

In some embodiments, the method is carried out in vivo. In accordance with this embodiment, the method further involves selecting a subject having a disease or disorder and in need of increased bioavailability of a therapeutic to treat the disease or disorder, where the contacting involves administering a composition as described herein to the selected subject, thereby sensitizing P-gp expressing cells of the subject to uptake of the therapeutic.

The subject may be any mammal. In some embodiments, the subject is a human. The subject may also be a non-human mammal. Suitable non-human mammals include, without limitation, murine, primate, equine, bovine, ursine, ovine, porcine, feline, canine, and lapine subjects.

Diseases or disorders include those of the blood system, cardiovascular system, digestive system, endocrine system, immune system, lymphatic system, muscular system, nervous system, renal system, reproductive system, respiratory system, and skeletal system.

In one embodiment, the subject has a cardiac disease or disorder. As used herein, the term "cardiac disease or disorders" refers to a disease or disorder of the cardiovascular system, blood system, or nervous system (e.g., arteries and veins) where an alteration of a heart function occurs based upon parameters including, but not limited to, electrical and/or muscular balance. Exemplary cardiac diseases or disorders may include, but are not limited to, myocardial infarction, angina pectoris, heart rhythm arrhythmias, tachycardias, atrial fibrillation, thrombophilia, arterial stenosis, venous stenosis, coronary artery disease, percutaneous transluminal coronary angioplasty ("PTCA"), coronary artery bypass surgery ("CABG"), restenosis, peripheral arterial disease, stroke, abdominal aorta aneurysm, intracranial aneurysm, large artery atherosclerotic stroke, cardiogenic stroke, an early onset myocardial infarction, heart failure, pulmonary embolism, acute coronary syndrome ("ACS"), angina, cardiac hypertrophy, arteriosclerosis, myocarditis, pancarditis, endocarditis, hypertension, congestive heart failure, atherosclerosis, cerebrovascular disease, declining cardiac health, ischemic heart disease, pericarditis, cardiogenic shock, alcoholic cardiomyopathy, congenital heart disease, ischemic cardiomyopathy, hypertensive cardiomyopathy, valvular cardiomyopathy, inflammatory cardiomyopathy, cardiomyopathy secondary to a systemic metabolic disease, dilated cardiomyopathy, hypertrophic cardiomyopathy, arrhythmogenic right ventricular cardiomyopathy, restrictive cardiomyopathy, noncompaction cardiomyopathy, valvular heart disease, hypertensive heart disease, myocardial ischemic attack, unstable angina, myocardial rupture, cardiogenic shock, embolism, deep vein thrombosis, arrhythmia, arrhythmogenic right ventricular cardiomyopathy, diabetic cardiomyopathy, mitral regurgitation, mitral valve prolapse, peripheral vascular disease, artery disease, carotid artery disease, deep vein thrombosis, venous diseases, cerebrovascular disease, arterial aneurysm, left ventricular hypertrophy, hypertensive renal disease, hypertensive retinal disease, vasculitis, left main disease, arterial vascular disease, venous vascular disease, thrombosis of the microcirculation, a transient cerebrovascular accident, limb ischemia, aneurysm, thrombosis, superficial venous thrombosis, and deep venous thrombosis.

In another embodiment, the subject has a kidney disease or disorder. As used herein, the term "kidney disease or disorder" refers to a disease or disorder of the renal system where an alteration of kidney function occurs. Examples kidney diseases or disorders include, but are not limited to, chronic kidney diseases, primary kidney diseases, non-diabetic kidney diseases, glomerulonephritis, interstitial nephritis, diabetic kidney diseases, diabetic nephropathy, glomerulosclerosis, rapid progressive glomerulonephritis, renal fibrosis, Alport syndrome, IDDM nephritis, mesangial proliferative glomerulonephritis, membrano proliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, autosomal dominant (adult) polycystic kidney disease, autosomal recessive (childhood) polycystic kidney disease, acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate ("GFR"), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schónlein disease, a postinfectious glomerulonephritis, a bacterial endocarditis, a microscopic polyangiitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis nodosa, a calcineurin-inhibitor induced-vascular disease, an acute cellular vascular allograft rejection, an acute humoral allograft rejection, early renal function decline ("ERFD"), end stage renal disease ("ESRD"), renal vein thrombosis, acute tubular necrosis, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, and hydronephrosis.

In another embodiment, the subject has a neoplastic disease or disorder. As used herein, the term "neoplastic disease or disorder" refers to a disease or disorder in a subject in which there are cells and/or tissues which proliferate abnormally. Neoplastic disorders can arise from any of the major systems of the body including, but not limited to, the blood system, cardiovascular system, digestive system, endocrine system, immune system, lymphatic system, reproductive system, muscular system, nervous system, renal system, reproductive system, respiratory system, and skeletal system. Exemplary neoplastic disorders include, but are not limited to, cancers, sarcomas, tumors, leukemias, and lymphomas.

In one embodiment, the neoplastic disease or disorder is cancer. As used herein, the term "cancer" refers to a condition involving abnormal cell growth within a subject having the potential to invade or spread to other parts of the body. Exemplary cancers include, but are not limited to, esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non-small cell lung cancer ("NSCLC"), squamous cell non-small cell lung cancer, breast cancer, recurrent metastatic breast cancer, hepatocellular carcinoma, Hodgkin's lymphoma, follicular lymphoma, non-Hodgkin's lymphoma, advanced B-cell NHL, HL including diffuse large B-cell lymphoma ("DLBCL"), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21)(q22;q22); RUNX1-RUNX1T1; adult acute myeloid leukemia with t(9;11)(p22;q23); MLLT3-MLL; adult acute promyelocytic leukemia with t(15;17)(q22;q12); PML-RARA; alkylating agent-related acute myeloid leukemia, chronic lymphocytic leukemia, Richter's syndrome; Waldenstrom macroglobulinemia, adult glioblastoma; adult gliosarcoma, recurrent glioblastoma, recurrent childhood rhabdomyosarcoma, recurrent Ewing's sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma ("HNSCC"), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent Merkel cell carcinoma; stage III Merkel cell carcinoma; stage IV Merkel cell carcinoma, myelodysplastic syndrome and recurrent mycosis fungoides and Sézary syndrome.

The cancer may be invasive, non-invasive, recurrent, and/or metastatic.

In one embodiment, the cancer is breast cancer. A variety of molecular factors may be used to categorize breast cancers, including hormone receptors and Human Epidermal Growth Factor Receptor 2 ("HER2") status. The most reproducibly identified molecular subtypes among the hormone receptor-positive cancers are the luminal A and luminal B groups. The HER2 and basal-like groups are the major molecular subtypes identified among hormone receptor-negative breast cancers. Other molecular subtypes include, but are not limited to, luminal C and normal breast-like groups. These breast cancer molecular subtypes differ with regard to their patterns of gene expression, clinical features, response to treatment, and prognosis (Stuart Schnitt, "Classification and Prognosis of Invasive Breast Cancer: from Morphology to Molecular Taxonomy," *Modern Pathology* 23:S60-S64 (2010), which is hereby incorporated by reference in its entirety).

In some embodiments, the breast cancer is selected from the group comprising Luminal A breast cancer, Luminal B breast cancer, triple-negative/basal-like breast cancer, HER2-enriched breast cancer, and normal-like breast cancer.

Luminal A breast cancers are hormone-receptor positive (estrogen-receptor and/or progesterone-receptor positive), HER2 negative, and has low levels of the protein Ki-67, which helps control how fast cancer cells grow. Luminal A cancers are low-grade and tend to grow slowly.

Luminal B breast cancers are hormone-receptor positive (estrogen-receptor and/or progesterone-receptor positive), and either HER2 positive or HER2 negative with high levels of Ki-67. Luminal B cancers generally grow slightly faster than luminal A cancers and their prognosis is slightly worse.

Triple-negative/basal-like breast cancers are hormone-receptor negative (estrogen-receptor and progesterone-receptor negative) and HER2 negative. This type of cancer is more common in women with BRCA1 gene mutations.

HER2-enriched breast cancers are hormone-receptor negative (estrogen-receptor and progesterone-receptor negative) and HER2 positive. HER2-enriched cancers tend to grow faster than luminal cancers and can have a worse prognosis, but they are often successfully treated with targeted therapies aimed at the HER2 protein, such as Herceptin (chemical name: trastuzumab), Perjeta (chemical name: pertuzumab), Tykerb (chemical name: lapatinib), and Kadcyla (chemical name: T-DM1 or ado-trastuzumab emtansine).

Normal-like breast cancers are similar to luminal A disease: hormone-receptor positive (estrogen-receptor and/or progesterone-receptor positive), HER2 negative, and have low levels of the protein Ki-67, which helps control how fast cancer cells grow.

In some embodiments, the cancer is multidrug resistant ("MDR") cancer. As used herein, the terms "multidrug-resistance" or "MDR" refer to the circumstance where a disease does not respond to one or more drugs or drug treatments. MDR cancer can be intrinsic, wherein the disease has never been responsive to the one or more drugs or drug treatments. MDR can also be acquired, wherein the disease ceases to respond to the one or more drugs or drug treatments that the disease had previously been responsive to. MDR is characterized by cross-resistance of a disease to more than one functionally and/or structurally unrelated drug.

MDR may be mediated by various ABC transporter proteins. One form of MDR is mediated by a membrane bound energy-dependent efflux pump designated as P-gp that is encoded by the ATP binding cassette subfamily B member 1 ("ABCB1") or multidrug resistance protein 1 ("MDR1") (Kretch et al., "ABCB1/MDR1 Contributes to the Anticancer Drug-Resistant Phenotype of IPH-926 Human Lobular Breast Cancer Cells," *Cancer Lett.* 315(2):153-60 (2012), which is hereby incorporated by reference in its entirety). In particular, P-gp has been shown to play a major role in the intrinsic and acquired resistance of a number of human tumors (Leslie et al., "Multidrug Resistance Proteins: P-glycoprotein, MRP1, MRP2, and BCRP (ABCG2) in Tissue Defense," *Tox. Appl. Pharm.* 201(3):216-37 (2005), which is hereby incorporated by reference in its entirety). Thus, P-gp associated MDR is a major factor in tumor cell resistance to chemotherapeutic agents.

Additional exemplary ABC transporter proteins that confer MDR include, but are not limited to, MRP1 (gene symbol ABCC1), MRP2 (gene symbol ABCC2), and the breast cancer resistance protein BCRP (gene symbol ABCG2) (Leslie et al., "Multidrug Resistance Proteins: P-glycoprotein, MRP1, MRP2, and BCRP (ABCG2) in Tissue Defense," *Tox. Appl. Pharm.* 201(3):216-37 (2005), which is hereby incorporated by reference in its entirety). A person of ordinary skill in the art will appreciate that the adenosine receptor agonists of the present invention may be used to module the expression or function of any of the above-identified MDR proteins including, but not limited to, MRP1, MRP2, and BCRP.

MDR cancer is discussed in greater detail in "Detoxification Mechanisms and Tumor Cell Resistance to Anticancer Drugs," by Kuzmich and Tew, particularly section VII "The Multidrug-Resistant Phenotype (MDR)," Medical Research Reviews, Vol. 11, No. 2, 185-217, (Section VII is at pp. 208-213) (1991); and in "Multidrug Resistance and Chemosensitization: Therapeutic Implications for Cancer Chemotherapy," by Georges, Sharom and Ling, Advances in Pharmacology, Vol. 21, 185-220 (1990), which are hereby incorporated by reference in their entirety.

The cancer or MDR cancer may be selected, for example, from the group of cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin, central nervous system; sarcomas of the soft tissue and bone; melanomas of cutaneous and intraocular origin; and malignancies including leukemias and lymphomas, Hodgkin's disease, lymphomas of lymphocytic and cutaneous origin, acute and chronic leukemia, and plasma cell neoplasms.

In some embodiments, the MDR cancer is within the central nervous system ("CNS"). As used herein, the term "central nervous system" refers to a subject's brain and/or spinal cord. Exemplary CNS cancers include, but are not limited to, acoustic neuroma, adenoma, astrocytoma, glioblastoma, brain stem glioma, breast cancer and metastatic brain tumors, chondroma, chondrosarcoma, chordoma, colon cancer and metastatic brain tumors, convexity meningioma, encephaloceles, ependymoma, esthesioneuroblastoma, fibrillary astrocytoma, fibrous dysplasia, giant cell tumor, germ cell tumor, gliomas, gliomatosis cerebri, oligodendroglioma, optic nerve glioma, hemangiopericytoma, kidney cancer and metastatic brain tumors, lung cancer and metastatic brain tumors, medulloblastoma, melanoma (skin cancer) and metastatic brain tumors, meningioma, metastatic brain tumors, mixed glioma, nasopharyngeal angiofibroma, neurofibroma, neurofibromatosis, olfactory neuroblastoma (esthesioneuroblastoma), oligoastrocytoma, oligodendroglioma, optic glioma, osteoma, paranasal sinus cancer, pituitary adenoma, Rathke's cleft cyst, rhabdomyosarcoma, and schwannoma.

In some embodiments, the cancer is not within the CNS. Accordingly, the cancer is not a acoustic neuroma, adenoma, astrocytoma, glioblastoma, brain stem glioma, breast cancer and metastatic brain tumors, chondroma, chondrosarcoma, chordoma, colon cancer and metastatic brain tumors, convexity meningioma, encephaloceles, ependymoma, esthesioneuroblastoma, fibrillary astrocytoma, fibrous dysplasia, giant cell tumor, germ cell tumor, gliomas, gliomatosis cerebri, oligodendroglioma, optic nerve glioma, hemangiopericytoma, kidney cancer and metastatic brain tumors, lung cancer and metastatic brain tumors, medulloblastoma, melanoma (skin cancer) and metastatic brain tumors, meningioma, metastatic brain tumors, mixed glioma, nasopharyngeal angiofibroma, neurofibroma, neurofibromatosis, olfactory neuroblastoma (esthesioneuroblastoma), oligoastrocytoma, oligodendroglioma, optic glioma, osteoma, paranasal sinus cancer, pituitary adenoma, Rathke's cleft cyst, rhabdomyosarcoma, or a schwannoma.

In accordance with the methods described herein, where the method further involves selecting a subject having a disease or disorder, in some embodiments, the disease or disorder may not be a disease or disorder of the CNS. Accordingly, in some embodiments, the disease or disorder is not a behavioral disorder, a personality disorder, dementia, a brain cancer, a neurodegenerative disorder, pain, a viral brain infection, a sleep disorder, a seizure disorder, acid lipase disease, Fabry disease, Wernicke-Korsakoff syndrome, ADHD, anxiety disorder, borderline personality disorder, bipolar disorder, depression, eating disorder, obsessive-compulsive disorder, schizophrenia, Alzheimer's disease, Barth syndrome and Tourette's syndrome, Canavan disease, Hallervorden-Spatz disease, Huntington's disease, Lewy Body disease, Lou Gehrig's disease, Machado-Joseph disease, Parkinson's disease, or Restless Leg syndrome.

In accordance with any of the methods described herein, where the method further involves selecting a subject having a disease or disorder, the method may further involve administering to the selected subject a therapeutic to treat the disease or disorder.

In some embodiments, the subject has a kidney disease or disorder. Accordingly, the therapeutic may be selected from the group comprising cabozantinib, lenvatinib, calcifediol, tacrolimus, nivolumab, lesinurad, ferric citrate, ledipasvir and sofosbuvir, ferric carboxymaltose, cysteamine bitartrate, everolimus, axitinib, mirabegron, peginesatide, avanafil, regorafenib, glucarpidase, oxybutynin, belatacept, eculizumab, carglumic acid, dutasteride, tamsulosin, cabazitaxel, sipuleucel-T, rifaximin, everolimus, everolimus, bevacizumab, ferumoxytol, oxybutynin chloride, pazopanib, degarelix for injection, fesoterodine fumarate, doripenem, methoxy polyethylene glycol-epoetin beta, sevelamer carbonate, temsirolimus, conivaptan, lanthanum carbonate, trospium chloride, cinacalcet, solifenacin succinate, agalsidase beta, oxybutynin transdermal system, alfuzosin HCl extended-release tablets, leuprolide acetate, mesna, Dutasteride, ertapenem for injection, calcium acetate gel caps, and combinations thereof.

In some embodiments, the subject has a cardiac disease or disorder. Accordingly, the therapeutic may be a digitalis-like compound ("DLC"). Exemplary digitalis-like compounds include, but are not limited to, digoxin, digitoxin, and ouabain. DLCs are also known as cardiac glycosides and are produced and sequestered by certain plants and animals as a protective mechanism against herbivores or predators. Currently, the DLCs digoxin and digitoxin are used in the treatment of cardiac congestion and some types of cardiac arrhythmia, despite having a very narrow therapeutic index. P-gp is the only known ATP-dependent efflux transporter that handles digoxin as a substrate, thereby inhibiting digoxin (Gozalpour et al., "Interaction of Digitalis-Like Compounds with P-Glycoprotein," *Toxicol Sci.* 131(2):502-11 (2013), which is hereby incorporated by reference in its entirety).

In some embodiments, the therapeutic is an antiarrhythmic agent, an anticoagulant agents, an antihypertensive agent, or an antiplatelet agent. Suitable antiarrhythmic agents include, without limitation, amiodarone, bepridil, dronedarone, digoxin, felodipine, propafenone, quinidine, and verapamil. Suitable anticoagulant agents include, for example, apixaban, dabigatran, rivaroxaban, edoxaban, and warfarin. Suitable antihypertensive agents include, for example, aliskiren, captopril, carvedilol, celiprolol, diltiazem, felodipine, isradipine, labetalol, losartan, mibefradil, nadolol, nicardipine, nifedipine, propranolol, reserpine, talinolol, telmisartan, and timolol. Suitable antiplatelet agents include, for example, aspirin, clopidogrel, dipyridamole, prasugrel, ticagrelor, statins, atorvastatin, and lovastatin. Additional suitable therapeutics include, without limitation, avasimibe, ranolazine, and ambrisentan. (Wessler et al., "The P-Glycoprotein Transport System and Cardiovascular Drugs," *Journal of the American College of Cardiology* 61(25): 2495-2502 (2013), which is hereby incorporated by reference in its entirety).

As used herein, the term "mTOR inhibitor" refers to a compound which blocks the mechanistic target of rapamycin ("mTOR"). mTOR is a serine/threonine-specific protein kinase that regulates cellular metabolism, growth, and proliferation.

In one embodiment, the subject is undergoing tissue transplant and the therapeutic is an mTOR inhibitor. Exemplary mTOR inhibitors include, but are not limited to, rapamycin (Sirolimus) and rapamycin analogs (e.g., everolimus and temsirolimus). Rapamycin functions by inhibiting the activation of T cells and B cells by reducing the production of interleukin-2 (IL-2) and is used as an immunosuppressant against transplant rejection (Saunders et al., "Rapamycin in Transplantation: A review of the evidence," *Kidney International* 59(1): 3-16 (2001), which is hereby incorporated by reference in its entirety). mTOR inhibitors have proven their efficacy in renal transplantation and offer renal and antiviral benefits. Sirolimus and everolimus differ mainly in pharmacokinetic characteristics (Klawitter et al., "Everolimus and Sirolimus in Transplantation-Related but Different," *Expert Opin Drug Saf.* 14(7):1055-70 (2015), which is hereby incorporated by reference in its entirety). In one embodiment, the therapeutic is selected from the group comprising rapamycin, sirolimus, temsirolimus, everolimus, deforolimus, and combinations thereof.

In another embodiment, the subject has cancer and the therapeutic is a chemotherapeutic.

Chemotherapeutic agents include numerous compounds such as taxane compounds and derivatives. Taxane compounds were initially extracted from the Pacific yew tree, *Taxus brevifolia*. They include, for example, paclitaxel and its derivatives or docetaxel and its derivatives. Additional taxane derivatives and methods of synthesis are disclosed in U.S. Pat. No. 6,191,287 to Holton et al, U.S. Pat. No. 5,705,508 to Ojima et al, U.S. Pat. Nos. 5,688,977 and 5,750,737 to Sisti et. al, U.S. Pat. No. 5,248,796 to Chen et al, U.S. Pat. No. 6,020,507 to Gibson et al, U.S. Pat. No. 5,908,835 to Bissery, which are hereby incorporated by reference in their entirety.

Some chemotherapeutic cancer agents are mitotic inhibitors (vinca alkaloids). These include vincristine, vinblastine, vindesine and Navelbine™ (vinorelbine,5'-noranhydroblastine). Similarly, chemotherapeutic cancer agents include, for example, topoisomerase I inhibitors such as camptothecin compounds. As used herein, "camptothecin compounds" include Camptosar™ ("irinotecan HCL"), Hycamtin™ ("topotecan HCL") and other compounds derived from camptothecin and its analogues.

Another category of chemotherapeutic cancer agents are podophyllotoxin derivatives such as etoposide, teniposide and mitopodozide.

An additional category of chemotherapeutic cancer agents includes anti-tumor antibodies, such as dacarbazine, azacytidine, amsacrine, melphalan, ifosfamide, and mitoxantrone.

In accordance with this embodiment, the chemotherapeutic is selected from the group consisting of alkylating agents, antimetabolites, anthracyclines, antitumor antibiotics, platinum-based chemotherapeutics, and plant alkaloids.

As used herein, the term "alkylating agents" refers to an agent which alkylates the genetic material in tumor cells. Exemplary alkylating agents include, without limitation, cisplatin, cyclophosphamide, nitrogen mustard, trimethylene thiophosphoramide, carmustine, busulfan, chlorambucil, belustine, uracil mustard, chlornaphazin, and dacarbazine.

Exemplary antimetabolites include, without limitation, cytosine arabinoside, fluorouracil, methotrexate, mercaptopurine, azathioprime, and procarbazine.

Exemplary anthracyclines include, without limitation, Daunorubicin (Daunomycin), Daunorubicin (liposomal), Doxorubicin (Adriamycin), Doxorubicin (liposomal i.e., Doxil), Epirubicin, Idarubicin, Valrubicin, Mitoxantrone, and mixtures thereof.

Exemplary antitumor antibiotics include, without limitation, doxorubicin, bleomycin, dactinomycin, daunorubicin, mithramycin, mitomycin, mytomycin C, and daunomycin.

Exemplary platinum-based chemotherapeutics include, without limitation, oxaliplatin, tetraplatin, cisplatin, and carboplatin and combinations thereof.

Exemplary plant alkaloids include, without limitation, berberine, evodiamine, matrine, piperine, sanguinarine, and tetrandrine (Lu et al., "Alkaloids Isolated from Natural Herbs as the Anticancer Agents," *Evidence-Based Complementary and Alternative Medicine* Article ID 485042, 12 pages (2012), which is hereby incorporated by reference in its entirety).

In one embodiment, the chemotherapeutic is selected from the group consisting of oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab ozogamicin, bortezomib, erlotinib, cetuximab, bevacizumab, sunitinib, sorafenib, dasatinib, panitumumab, asparaginase, tretinoin, arsenic trioxide, salts thereof, active metabolites thereof, and combinations thereof.

The agonists, antagonists, therapeutics, and compositions including the same (i.e., the agents and compositions of the present invention) may be administered by any method and route of administration suitable to the treatment of the disease, typically as pharmaceutical compositions.

Administration may be locally or systemically. In particular, the agents and compositions described herein can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The agents and compositions described herein may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the agents and compositions described herein may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of the agents and compositions described herein in such therapeutically useful compositions is such that a suitable dosage will be obtained. A convenient unitary dosage formulation contains the agents and compositions in amounts from 0.1 mg to 1 g each, for example 5 mg to 500 mg. Typical unit doses may, for example, contain about 0.5 to about 500 mg, or about 1 mg to about 500 mg of an agent according to the present invention.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agents and compositions described herein may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents and compositions described herein may also be administered directly to the airways in the form of an aerosol. For use as aerosols, the agents or compositions described herein in solution or suspension may be packaged in a pressurized aerosol container together with suitable propellants, for example, hydrocarbon propellants like propane, butane, or isobutane with conventional adjuvants. The agents and compositions as described herein may be administered in a non-pressurized form such as in a nebulizer or atomizer.

Administering the A2A AR agonist as described herewith may occur in combination with administering a therapeutic to the selected subject.

Administering the A2A AR agonist as described herewith may occur simultaneously with administering the therapeutic. In some embodiments, the A2A AR agonist and the therapeutic are formulated in a single unit dosage form.

Administering the A2A AR agonist may occur before administering the therapeutic. In some embodiments, the A2A AR agonist is administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic.

Administering the A2A AR agonist may occur after administering the therapeutic. In accordance with this embodiment, the A2A AR agonist is administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours after the therapeutic.

In some embodiments, administering the A2A AR agonist improves the efficacy of the therapeutic (e.g., a cancer therapeutic) as compared to when the administration step does not occur.

A second aspect of the invention relates to a method of enhancing the bioavailability of a chemotherapeutic in a subject having multi-drug resistant ("MDR") cancer. The method involves selecting a subject having MDR cancer and administering to the selected subject an effective amount of an A2A adenosine receptor ("A2A AR") agonist to enhance intracellular delivery of a cancer therapeutic in the subject.

Administering the A2A AR agonist may be carried out as described above.

In some embodiments, administering the A2A AR agonist occurs in combination with administering the cancer therapeutic to the selected subject.

Suitable cancer therapeutics are described in detail above.

Administering the A2A AR agonist as described herewith may occur simultaneously with administering the cancer therapeutic. In some embodiments, the A2A AR agonist and the cancer therapeutic are formulated in a single unit dosage form.

Administering the A2A AR agonist may occur before administering the cancer therapeutic. In some embodiments, the A2A AR agonist is administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before cancer the therapeutic.

Administering the A2A AR agonist may occur after administering the cancer therapeutic. In accordance with this embodiment, the A2A AR agonist is administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours after the cancer therapeutic.

In some embodiments, administering the A2A AR agonist improves the efficacy of the cancer therapeutic as compared to when the administration step does not occur.

In one embodiment, administering the A2A AR agonist improves the efficacy of the cancer therapeutic as compared to when the administering step does not occur.

Administering the A2A AR agonist may be carried out orally, parenterally, periadventitially, subcutaneously, intravenously, intramuscularly, intraarticularly, intraperitoneally, by inhalation, by intranasal instillation, by implantation, by intracavitary or intravesical instillation, intraocularly, intraarterially, intralesionally, transdermally, or by application to mucous membranes.

In some embodiments, the MDR cancer is selected from the group consisting of cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin, central nervous system; sarcomas of the soft tissue and bone; melanomas of cutaneous and intraocular origin; and malignancies including leukemias and lymphomas, Hodgkin's disease, lymphomas of lymphocytic and cutaneous origin, acute and chronic leukemia, and plasma cell neoplasms.

As described above, the MDR cancer may be within the central nervous system ("CNS").

In some embodiments, the MDR cancer is breast cancer.

Intestinal P-gp is well known to limit the absorption of xenobiotics and is believed to act as a cytotoxic defense mechanism in the intestine. However, the expression of P-gp limits treatment for colon and other cancers (Gottesman et al, "The Role of Multidrug Resistance Efflux Pumps in Cancer: Revisiting a JNCI Publication Exploring Expression of the MDR1 (P-glycoprotein) Gene," *J Natl Cancer Inst.* 107(9): djv222 (2015). In one embodiment, the MDR cancer is colon cancer.

In some embodiments, the A2A AR agonist is a selective A2A AR agonist. Suitable A2A AR agonists are described in detail above.

As described herein, in some embodiments, the method may suppress neoplastic cell growth in the selected subject. In one embodiment, the method inhibits metastasis of the MDR cancer in the selected subject.

As described above, the selected subject may be a human or non-human mammal.

In some embodiments, where the A2A AR agonist is not a selective A2A AR agonist, the A2A AR agonist is not adenosine.

A third aspect of the invention relates to a method of increasing P-gp-mediated efflux in a cell. The method involves contacting a cell with an A2A AR antagonist in an amount sufficient to increase P-gp-mediated efflux.

As used herein, the term "antagonist" refers to a compound, the presence of which results in a decrease in the magnitude of an activity of a receptor. The presence of an antagonist may result in partial or complete inhibition of an activity of a receptor.

Antagonism of the A2A or A2B receptors results in an increase of P-gp expression or function.

The antagonist may be a non-selective or general adenosine receptor antagonist or a selective adenosine receptor antagonist. Exemplary non-selective adenosine receptor antagonists include, but are not limited to, 1,3,7-Trimethylpurine-2,6-dione ("caffeine") and 1,3-Dimethyl-7H-purine-2,6-dione ("1,3-Dimethylxanthine" or "theophylline").

Exemplary selective A2A AR antagonists include, for example, istradefylline ("KW-6002"), 2-(2-Furanyl)-7-(2-phenylethyl)-7H-pyrazolo[4,3-e][1,2,4]triazolo[1,5-c]pyrimidin-5-amine ("SCH-58261"), or 2-(2-Furanyl)-7-[3-(4-methoxyphenyl)propyl]-7H-pyrazolo[4,3-e][1,2,4]triazolo[1,5-c]pyrimidin-5-amine ("SCH 442416"). In some embodiments, the A2A AR antagonist is caffeine. In another embodiment, the A2A AR antagonist is istradefylline. In some embodiments, the A2A AR antagonist is SCH-58261.

In some embodiments, the A2A AR antagonist is a precursor or derivative of an A2A AR antagonist. Accordingly, the A2A AR antagonist may be desmethyl SCH 442416.

Exemplary selective A2B AR antagonists include, for example 3-Ethyl-3,9-dihydro-1-propyl-8-[1-[[3-(trifluoromethyl)phenyl]methyl]-1H-pyrazol-4-yl]-1H-purine-2,6-dione ("GS 6201") and N-(4-Cyanophenyl)-2-[4-(2,3,6,7-tetrahydro-2,6-dioxo-1,3-dipropyl-1H-purin-8-yl)phenoxy]-acetamide ("MRS 1754"). Additional exemplary A2B AR antagonists include caffeine and theophylline.

As described above, the method may be carried out in vitro, in vivo, or ex vivo.

The method may further comprise selecting a subject having a disease or disorder mediated by P-gp expression and administering the A2A AR antagonist to the selected subject. In accordance with this embodiment, the disease or disorder is, for example, a drug intoxication, inclusion body myositis, cerebral amyloid angiopathy, amyloidosis, or eye disease.

P-gp upregulation using AR antagonists may protect, e.g., kidney, gut, lung, and liver organs from toxicity due to toxic drug or poison absorption.

In one embodiment, administering the A2A AR antagonist to the selected subject blocks toxic substance from entering the CNS.

The disease or disorder treated in accordance with this aspect may be one mediated by accumulation of protein aggregates (e.g., beta amyloid) in the brain. In one embodiment, the disease or disorder is Alzheimer's disease ("AD") or dementia. In some embodiments, administering the A2A AR antagonist to the selected subject promotes the clearance of beta-amyloid protein in AD by upregulation of P-gp function.

In one embodiment, P-gp upregulation protects the gut from drug-induced inflammatory bowel disease.

In some embodiments, the disease or disorder is not one of the CNS. In accordance with this embodiment, the disease or disorder is not Alzheimer's disease ("AD") or Creutzfeldt-Jakob disease ("CJD"). In one example, the disease or disorder is ulcerative colitis (Ufer et al., "Decreased Sigmoidal ABCB1 (P-glycoprotein) Expression in Ulcerative Colitis is Associated with Disease Activity," Pharmacogenomics. 10(12):1941-53 (2009), which is hereby incorporated by reference in its entirety.) In another example, the disease or disorder is Crohn's disease (Farrell et al., "High Multidrug Resistance (P-glycoprotein 170) Expression in Inflammatory Bowel Disease Patients who Fail Medical Therapy," Gastroenterology 118(2):279-88 (2000), which is hereby incorporated by reference in its entirety).

In one embodiment, the disease or disorder is associated with decreased P-gp expression. Exemplary diseases or disorders associated with decreased P-gp expression include, but are not limited to, CJD, AD, and ulcerative colitis (Vogelgesang et al., "Cerebrovascular P-glycoprotein Expression is Decreased in Creutzfeldt-Jakob Disease," Acta Neuropathol. 111(5):436-43 (2006) and Ufer et al., "Decreased Sigmoidal ABCB1 (P-glycoprotein) Expression in Ulcerative Colitis is Associated with Disease Activity," Pharmacogenomics. 10(12):1941-53 (2009), which are hereby incorporated by reference in their entirety).

EXAMPLES

Materials and Methods for Examples 1-5

Cells and Materials.

Cells and cell lines used include human brain endothelial cells ("HCMEC-D3") and primary human brain endothelial cells (purchased from Cell Systems). Lexiscan® was purchased from Toronto Research Chemicals. Rho123 was purchased from Sigma-Aldrich. Epirubicin (catalog 3260), PSC833 (catalog 4042), and NECA (catalog 1691) were purchased from Tocris. Anti-human CD31 antibody (catalog FAB3567C) was purchased from R&D Bioscience. P-gp antibodies were purchased as follows: catalog GTX108354, GTX23364 from GeneTex; catalog 557001 from BD Biosciences; catalog EPR10364-57 from Abcam. ABCG2 (catalog GTX23380) and GLUT1 (catalog GTX100684) antibodies were purchased from GeneTex. Anti-MMP9 antibody (catalog ab38898) was purchased from Abcam. Alexa Fluor 594-conjugated wheat germ agglutinin (WGA) (catalog W11262, Thermo Fisher) and mouse anti-caveolin-1 antibody (catalog 610493, BD Biosciences) were also used.

Mouse Primary Brain Endothelial Cell Culture.

Mice were sacrificed and meninges of brain were removed and ground using a plunger and centrifuged at 3,000 g for 5 minutes. The obtained pellet was dissolved in 18% dextran and centrifuged at 10,000 g for 10 minutes and digested with DMEM containing collagenase, DNAse, and dispase at 37° C. for 75 minutes. The sample was centrifuged for 5 minutes at 3,200 g, and the pellet was washed with warm PBS. The pellet was resuspended in DMEM/F12 with puromycin, heparin, 20% PDS, and 1-glutamine and plated onto the proper plate.

Subcellular Localization Analysis of P-gp in Brain Endothelial Cells.

To analyze the subcellular localization of P-gp in the HCMEC-D3 and primary brain endothelial cells, cells were plated on coverslips and fixed with PFA for 20 minutes. Cells were washed with 0.5% BSA 2 times and incubated with 5% goat serum for 45 minutes. Cells were incubated with 1:200 anti P-gp (BD Biosciences) overnight. Coverslips were washed 2 times and incubated with anti-mouse secondary antibody conjugated with Alexa Fluor 647 for 1 hour. Cell surface was stained with Alexa Fluor 568 WGA (Invitrogen, 1:200) or anti-CD31 (R&D Bioscience, 1:200). For costaining of caveolae, cells were stained with mouse anti-caveolin-1 (BD Biosciences, 1:200)

Immunoprecipitation Assay.

4 G Sepharose beads were purchased from Invitrogen and incubated with human P-gp antibody (BD Biosciences) overnight at 4° C. using a rocking shaker. Beads were washed twice using lysis buffer containing protease inhibitor, and lysates from primary brain endothelial cells were incubated overnight at 4° C. using a rocking shaker. Samples were spun down at 4,000 g for 2 minutes and washed with lysis buffer containing protease inhibitor 3 times. Samples were eluted with 0.1 M glycine (pH 2.8), and the eluent was mixed with sample buffer, which was loaded on a 10% SDS-PAGE gel run for 2 hours at 100 V and subsequently transferred to nitrocellulose paper for western blot analysis.

Western Blot.

HCMEC-D3 and HBMVEC cells were plated in 12-well plates and were grown until they reached 100% confluency. The media was replaced with fresh media containing 1 µM of Lexiscan® or NECA with proper vehicle control (DMSO) for up to 72 hours. Cells were lysed by lysis buffer (RPMI) containing protease inhibitor cocktail and stored for later use (−70° C.). For cytoskeletal fraction analysis, cells were lysed in CSK buffer (100 mM NaCl, 300 mM sucrose, 3 mM MgCl2, 10 mM PIPES, pH 6.8). For brain samples, half of the brain was homogenized and lysed with RPMI lysis buffer and centrifuged at 17,000 g for 20 minutes and 1:10 diluted samples were used for analysis. Sample was loaded on 7% SDS PAGE at 100 V for 1 hour and transferred to the nitrocellulose paper. It was blocked with 1% BSA and incubated with anti-P-gp antibody (Genetex, 1:2000) overnight. Subsequently, it was washed with TBST and incubated with anti-rabbit secondary antibody (1:2000) for 1 hour. It was washed with TBST and developed with ECL substrate and exposed to x-ray film. Anti-GAPDH or −β-actin antibody was used as loading control. The intensity of band was analyzed with densitometric analysis and plotted as a graph for analysis of time-course effect of AR signaling on P-gp expression.

Rho123 Uptake Assay.

Figures 4A, 4B, 4C, 4D:
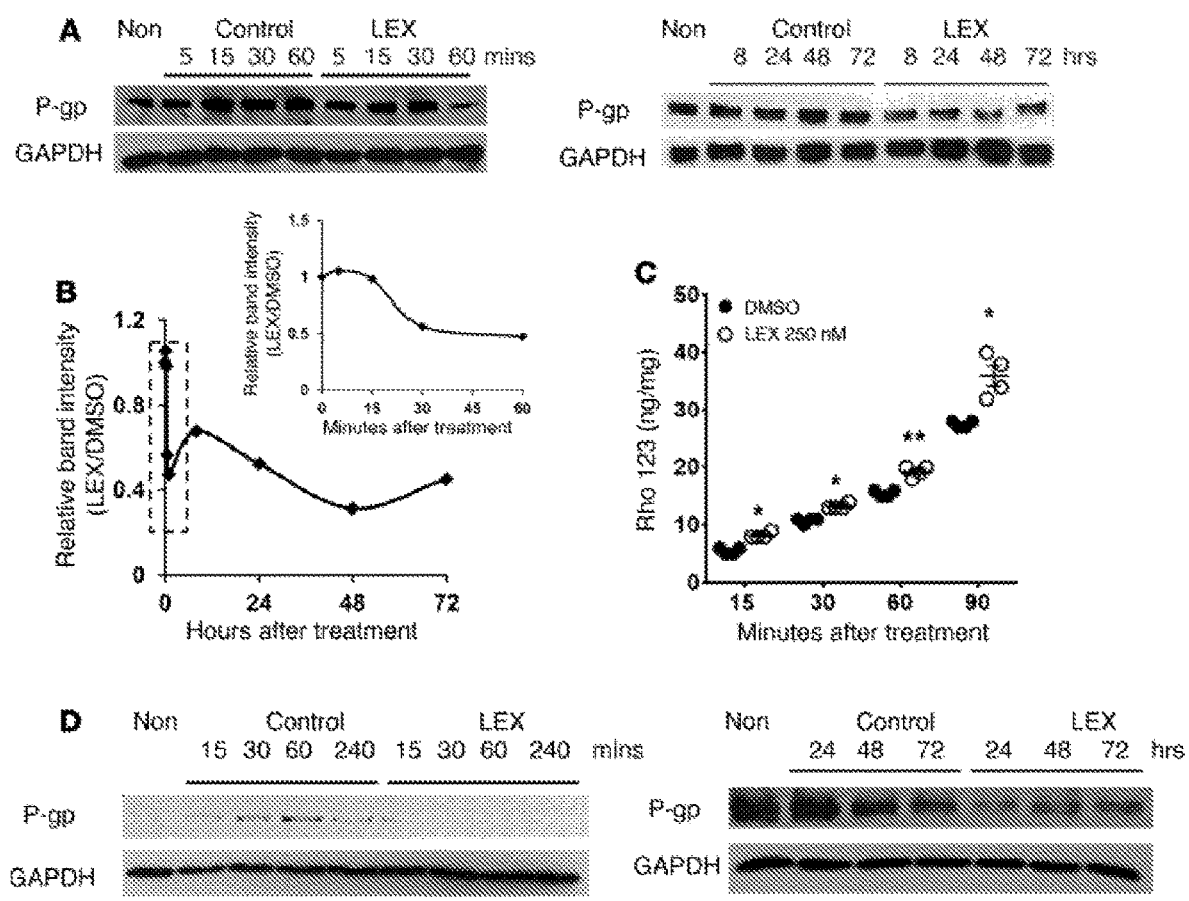
FIGS. 4A-4G shows that activation of A2A AR down-modulates P-gp expression and function in human brain endothelial cells.
Figures 4E, 4F, 4G:
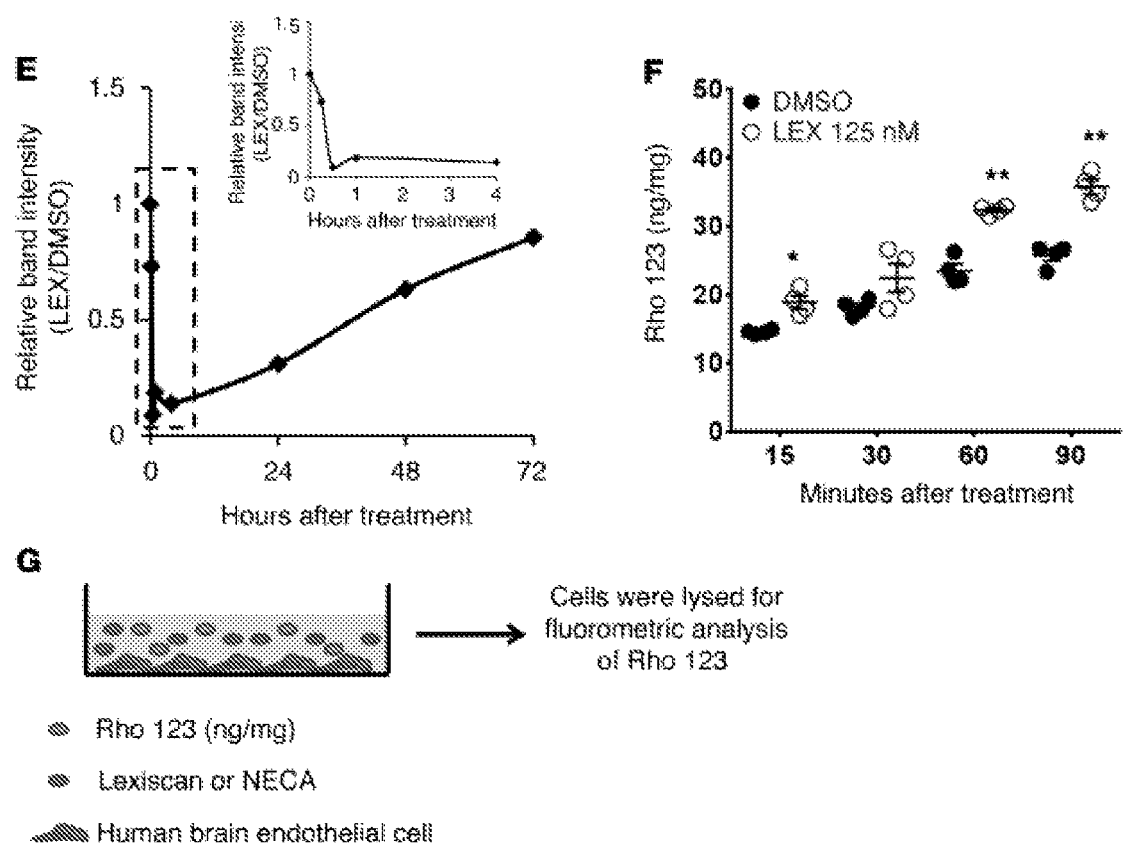

Human brain endothelial cells and primary brain endothelial cells were plated onto 48-well plates until 100% confluence was reached, and media were replaced with fresh media containing Rho123 (2.5 µM) with different concentrations of Lexiscan®, NECA, or PSC833. Reaction was halted by adding 250 µl of ice-cold PBS. Plate was washed with 250 µl of ice-cold PBS 3 times and lysed with lysis buffer. Each sample was analyzed using Synergy Fluometer (Biotek), with excitation at 488 nm and emission at 523 nm. Concentration of Rho123 was analyzed using standard curve created by serial dilution of Rho123. Final concentration of Rho123 was normalized using protein concentration of lysate measured using Bradford assay (Bio-Rad). For microscopic analysis of Rho123 uptake, cells were cultured on coverslip and Rho123 was treated with or without Lexiscan® or NECA with DMSO as control. Reaction was terminated by adding ice-cold PBS and washed with ice-cold PBS 3 times. Cells were fixed with PFA and costained with anti-human P-gp. Cells were visualized with a Zeiss fluorescent microscope and captured with axiovision software. FIG. 4G is a schematic illustration of the Rho123 uptake assay.

Rho123 Extravasation Assay.

Primary human brain endothelial cells were plated on 3 µm of porous membrane (Corning) until 100% confluency was reached. Media was replaced with HBSS and acclimated for 4 hours before initiation of experiments. Rho123 (2.5 µM) with or without Lexiscan® or NECA (0.25 µM) was applied on the upper chamber of porous membrane for up to 48 hours. Media at the bottom chamber were collected at different time points, and each sample was analyzed using Synergy Fluorometer (Biotek), with excitation at 488 nm and emission at 523 nm.

Epirubicin Brain Accumulation Assay.

For Lexiscan® study, 10 mg/kg of epirubicin was injected with or without Lexiscan® (0.05 mg/kg) at different time points, and mice were sacrificed. Mice were injected with NECA (0.08 mg/kg) or vehicle control at different time points, after which 10 mg/kg of epirubicin was injected intravenously for 15 minutes; mice were then sacrificed. At indicated time points, mice were perfused with ice-cold PBS and brain was collected for further analysis. Brain was ground and spun down in Tris-HCl (pH=8.0) at 17,000 g for 30 minutes, and supernatant was transferred to a new tube and precipitated with the same volume of MeOH. Samples were spun down at 17,000 g for 30 minutes, and the concentration for epirubicin was analyzed with fluorimetry with emission at 488 nm and excitation at 575 nm.

IFA of Frozen Section.

Mice were treated with Lexiscan® or NECA at different time points and were infused with ice-cold PBS and sacrificed. Half of the brain was cut and put in the cassette and filled with OCT solution. Samples were snap-frozen with liquid nitrogen, cut with cryostat (10 μm) and fixed with acetone for 5 minutes, and incubated with C219 for P-gp stain (1:100) and Glut1 for endothelial cell marker (1:100) at 4° C. overnight. Sections were washed with PBS and additionally stained with secondary antibody conjugated with fluorochrome. Full images of the brain sections were visualized and recorded using Aperio Scan Scope (Leica Biosystems).

Statistics.

All statistical analysis was carried out using GraphPad 5.0 software. Statistical significance was assessed using unpaired 2-tailed Student's t test. P values of less than 0.05 were considered to be statistically significant.

Example 1—P-gp is Highly Expressed in Primary Human Brain Endothelial Cells and a Human Brain Endothelial Cell Line Studies have shown that P-gp is highly expressed on the luminal side of BBB endothelial cells and on the plasma membrane due to its functional property as a transporter (Beaulieu et al., "P-Glycoprotein is Strongly Expressed in the Luminal Membranes of the Endothelium of Blood Vessels in the Brain," *Biochem J.* 326(pt 2):539-44 (1997), which is hereby incorporated by reference in its entirety). First, to confirm expression of P-gp in human brain endothelial cells, immunofluorescence assay ("IFA") of endothelial cells was performed using an antibody specific for P-gp. HCMEC-D3 cells, a human brain endothelial cell line, were observed to express abundant P-gp in the cytoplasm and, to a lesser extent, on the cell surface (FIG. 1A). Similarly, in human primary brain endothelial cells, HBMVEC, high P-gp expression was observed (FIG. 1A). This mostly cytoplasmic P-gp localization in brain endothelial cells is reminiscent of a P-gp expression pattern previously reported in human primary brain endothelial cells (Mills et al., "A2A Adenosine Receptor Signaling in Lymphocytes and the Central Nervous System Regulates Inflammation During Experimental Autoimmune Encephalomyelitis," *J Immunol.* 188(11):5713-22 (2012), which is hereby incorporated by reference in its entirety). However, this expression pattern of P-gp localization is different from the expression pattern observed in drug-resistant cancer cells, which show mostly surface expression (Paterson et al., "P-Glycoprotein is not Present in Mitochondrial Membranes," *Exp Cell Res.* 313 (14):3100-5 (2007), which is hereby incorporated by reference in its entirety). Thus, it is possible that the location/localization of P-gp is different in transformed versus normal cells and/or is different in different cell types.

In previous studies, it was reported that P-gp in brain endothelial cells is strongly colocalized with caveolae, which are specialized microdomains of cell membranes that can be separated by cell fractionation assay (Beaulieu et al., "P-Glycoprotein is Strongly Expressed in the Luminal Membranes of the Endothelium of Blood Vessels in the Brain," *Biochem J.* 326(pt 2):539-44 (1997); Bastiani et al., "Caveolae at a Glance," *J Cell Sci.* 123(22):3831-6 (2010); and Demeule et al., "P-Glycoprotein is Localized in Caveolae in Resistant Cells and in Brain Capillaries," *FEBS Lett.* 466(2-3):219-24 (2000), which are hereby incorporated by reference in their entirety). To determine whether P-gp is associated with caveolae, P-gp and caveolin-1, which is a major caveolae-associated protein (Bastiani et al., "Caveolae at a Glance," *J. Cell. Sci.* 123(22):3831-3836 (2010) and Demeule et al., "P-Glycoprotein Is Localized in Caveolae in Resistant Cells and in Brain Capillaries," *FEBS Lett.* 466(2-3):219-224 (2000), which are hereby incorporated by reference in their entirety), were co-stained. Strong colocalization of P-gp with caveolin-1 was observed in human primary brain endothelial cells (FIGS. 1A-1B). To determine whether P-gp colocalizes with caveolin-1, an immunoprecipitation assay was performed using P-gp antibody. A strong interaction between P-gp and caveolin-1 was observed (FIG. 1C). These results are in line with previous studies and suggest that caveolin-1 is involved in P-gp trafficking between the cell membrane and other cell compartments (Demeule et al., "P-Glycoprotein Is Localized in Caveolae in Resistant Cells and in Brain Capillaries," *FEBS Lett.* 466(2-3):219-224 (2000) and Jodoin et al., "P-Glycoprotein in Blood-Brain Barrier Endothelial Cells: Interaction and Oligomerization With Caveolins," *J. Neurochem.* 87(4): 1010-1023 (2003), which are hereby incorporated by reference in their entirety). Interestingly, colocalization of P-gp with caveolae was observed mostly in the cytoplasm rather than on the cell surface in both human and mouse primary brain endothelial cells (FIGS. 1A-1B, 2A-2B). While previous studies showed P-gp colocalized with caveolae, this is the first study that shows that P-gp colocalization with caveolae occurs in the cytoplasm.

Recent studies have shown that caveolin-1 is incorporated in the endosome called a cavicle, which is distinct from classical endosomes, and this special endosome actively delivers target proteins (including glycosylphosphatidylinositol-anchored [GPI-anchored] proteins) to the cell membrane (Lajoie et al., "Lipid Rafts, Caveolae, and Their Endocytosis," in INTERNATIONAL REVIEW OF CELL AND MOLECULAR BIOLOGY, Vol. 282: 135-163 (Jeon & Galluzzi eds., 2010); Shvets et al., "Dynamic Caveolae Exclude Bulk Membrane Proteins and are Required for Sorting of Excess Glycosphingolipids," *Nat. Commun.* 6:6867 (2015); and Mundy et al., "Dual Control of Caveolar Membrane Traffic by Microtubules and the Actin Cytoskeleton," *J. Cell. Sci.* 115(22):4327-4339 (2002), which are hereby incorporated by reference in their entirety). To determine whether P-gp actively circulates by caveolae transport to relocate to the site where substrate is present and ultimately to the cell surface, primary human brain endothelial cells were treated with the P-gp substrate Rho123 for 1 hour. A strong colocalization of P-gp with Rho123 and surface localization of P-gp was observed (FIGS. 1D-1E). Also, P-gp was strongly colocalized with caveolin-1 both on the cell surface and in the cytoplasm (FIGS. 1D-1E). These observations strongly indicate that P-gp may actively circulate in these endothelial cells by the caveolae-protein transport system and that upon stimulation (trigger) by its substrate, it relocalizes to the substrate's site. Thus, the cytoplasmic portion of P-gp appears to bind to its substrate and deliver it to the cell surface for expulsion.

Since mostly cytoplasmic localization of P-gp was observed (in contrast with cell-surface localization observed in MDR cancer cells) (Fu et al., "Actin Disruption Inhibits Endosomal Traffic of P-Glycoprotein-EGFP and Resistance to Daunorubicin Accumulation," *Am. J. Physiol. Cell Physiol.* 292(4):C1543-C1552 (2007), which is hereby incorporated by reference in its entirety), P-gp functionality was next characterized using the Rho123 uptake assay. Rho123 (a substrate of P-gp) is widely used to measure P-gp function, since its intracellular accumulation has a reciprocal relationship to P-gp levels (Lee et al., "Rhodamine Efflux Patterns Predict P-Glycoprotein Substrates in the National Cancer Institute Drug Screen," *Mol. Pharmacol.* 46(4):627-638 (1994), which is hereby incorporated by reference in its entirety). Brain endothelial cells were treated with a competitive inhibitor of P-gp, PSC833, and Rho123 uptake was measured. PSC833 is a functional inhibitor that directly binds to the drug-binding pocket of P-gp, thereby allowing entry of P-gp substrate into the cell. Rho123 accumulation increased in a time-dependent manner in both human primary brain endothelial cells and the human brain endothelial cell line (FIGS. 1F-1G). P-gp down-modulation was observed beginning at 60 minutes and was maintained up to 90 minutes, indicating that P-gp function was effectively down-modulated in HCMEC-D3 cells by the functional inhibitor (FIG. 1F). P-gp down-modulation was observed in primary human brain endothelial cells beginning at 60 minutes and was maintained up to 90 minutes (FIG. 1G). These results indicate that these cells are valid in in vitro models to test the modulation and function of P-gp by AR signaling.

Example 2—Activation of A2A AR Down-Modulates P-gp Expression and Function in Brain Endothelial Cells AR-mediated signaling has been shown to increase the permeability of the BBB to large molecules in vivo and in vitro (Kim et al., "A2A Adenosine Receptor Regulates the Human Blood-Brain Barrier Permeability," *Mol. Neurobiol.* 52(1):664-678 (2014) and Carman et al., "Adenosine Receptor Signaling Modulates Permeability of the Blood-Brain Barrier," *J. Neurosci.* 31(37):13272-13280 (2011), which are hereby incorporated by reference in their entirety).

Figure 3A:
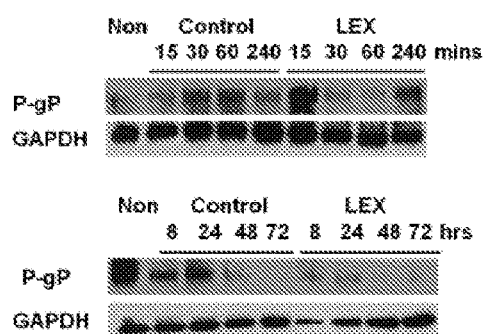
FIGS. 3A-3D illustrate that A2A AR activation decreases the expression of P-gp in primary mouse brain endothelial cells.
Figure 3B:
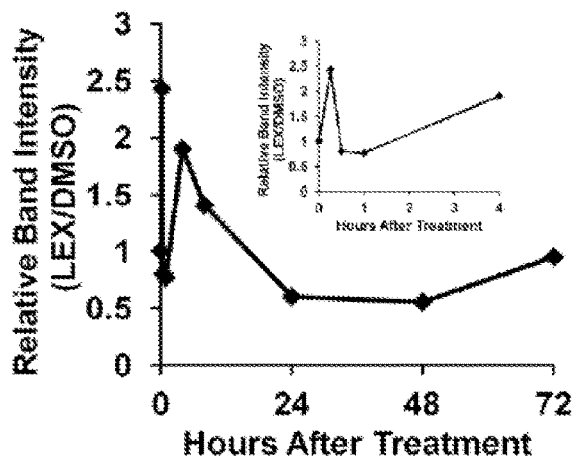
Figure 3C:
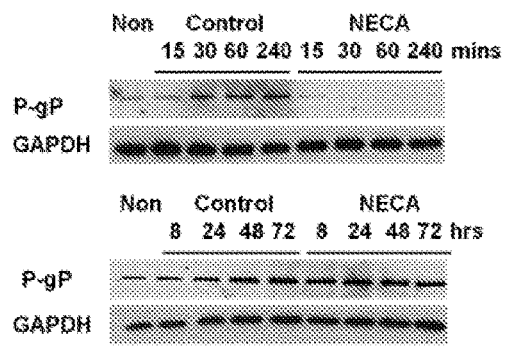
Figure 3D:
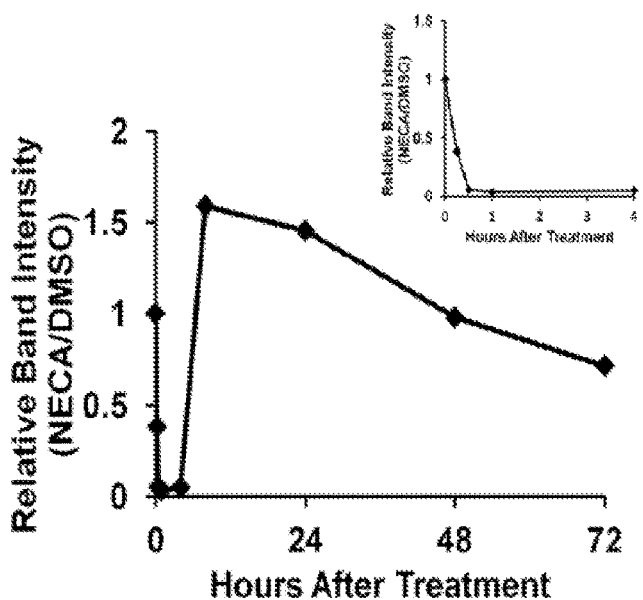

To test the hypothesis that AR signaling regulates P-gp function, in vitro BBB models were used to determine whether AR signaling could indeed inhibit the expression and function of P-gp. First, the effect of AR signaling on P-gp expression levels in primary mouse brain endothelial cells was tested. Cells were grown to form monolayers and then treated with or without 1 µM of the A2A AR agonist Lexiscan® or NECA, a broad-spectrum AR agonist, at different time points up to 72 hours. In Lexiscan®-treated samples, western blot analysis showed the rapid down-modulation of P-gp beginning at 30 minutes, which was maintained for up to 1 hour (FIGS. 3A-3B). This was reversed at 4 hours and began to decrease thereafter up to 48 hours, then reversed at 72 hours (FIGS. 3A-3B). In NECA-treated primary (mouse) brain endothelial cells, P-gp expression decreased very rapidly and remained down-modulated for up to 4 hours. By 8 hours, P-gp expression returned to baseline levels (FIGS. 3C-3D).

Figures 5A, 5B, 5C, 5D, 5E, 5F:
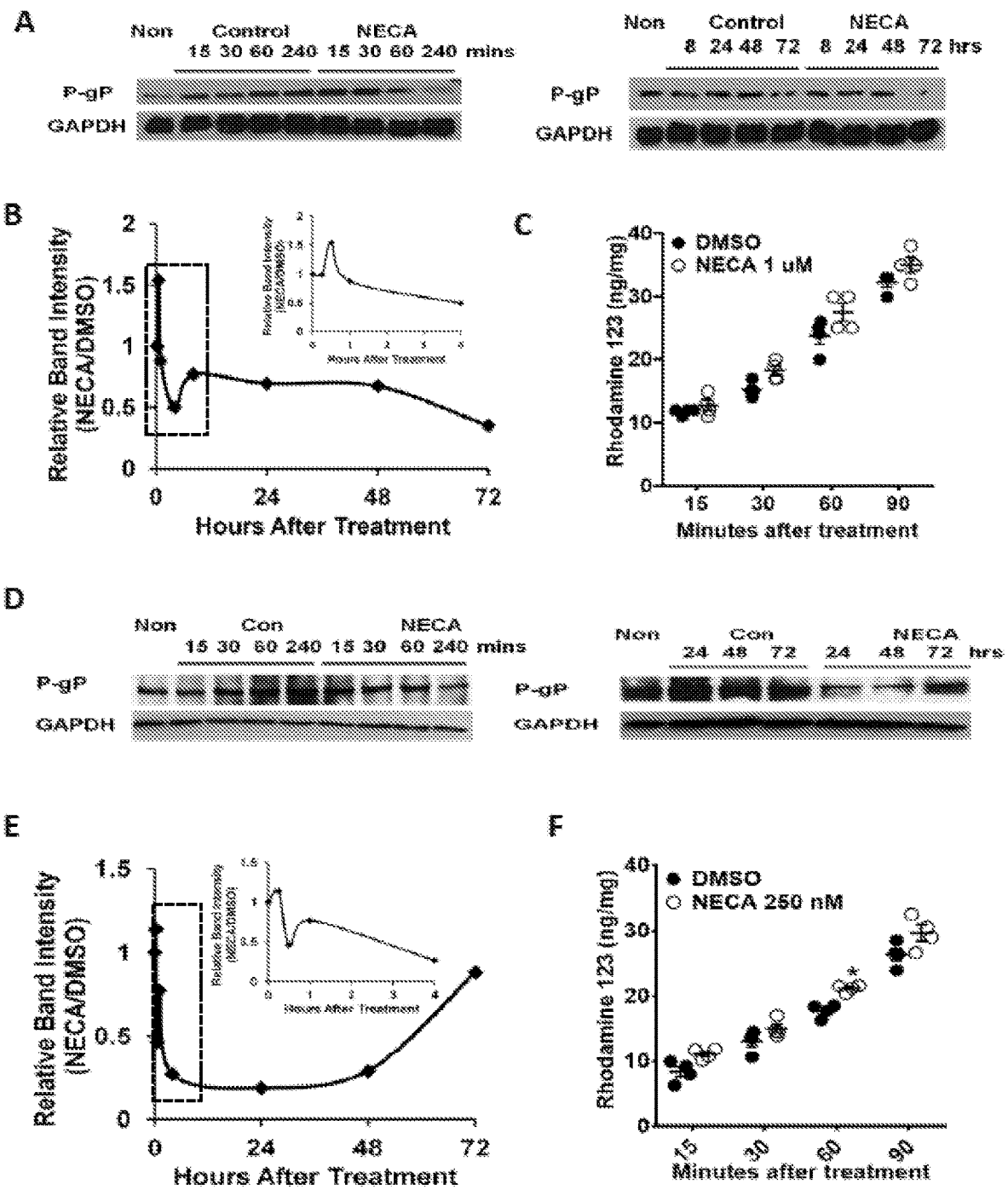
FIGS. 5A-5F are western blots and graphs summarizing the experimental results of each blot which illustrate that activation of A2A AR down-modulates P-gp expression and function in brain endothelial cells.

IFA experiments using HCMEC-D3 cells were used to verify the "visual" presence of the P-gp substrate and to map its timing and localization in endothelial cells. Monolayers of HCMEC-D3 cells were treated with Lexiscan® or NECA, and P-gp expression was analyzed by western blot analysis. In HCMEC-D3 cells, Lexiscan® treatment induced a rapid decrease in P-gp expression beginning at 30 minutes, which was maintained for up to 1 hour (FIGS. 4A-4B). Interestingly, at 24 to 48 hours, P-gp expression decreased even more prominently (FIGS. 4A-4B). NECA also decreased P-gp expression for up to 4 hours, and P-gp returned to basal levels at 8 hours and declined again between 48 and 72 hours (FIGS. 5A-5B). As proof that P-gp down-modulation by Lexiscan® and NECA correlates with increased substrate accumulation, the accumulation of Rho123 in brain endothelial cells was evaluated. Lexiscan® increased Rho123 accumulation in the HCMEC-D3 cell line beginning at 15 minutes, and this was maintained for up to 90 minutes (FIG. 4F). NECA treatment showed a similar trend in Rho123 accumulation, although it was not statistically significant (FIG. 5C). These results indicate that a decrease in P-gp expression level by AR activation is consistent with decreased P-gp functionality.

As cell lines do not always reproduce all the characteristics of primary cells, the effect of Lexiscan® and NECA treatment on P-gp expression in primary human brain endothelial cells was next examined. Both Lexiscan® and NECA treatment exerted effects on P-gp expression in human primary brain endothelial cells similar to those observed in the human brain endothelial cell line HCMEC-D3 (FIGS. 4D, 5D). Lexiscan® induced rapid down-modulation of P-gp expression, which began to decrease at 15 minutes and was maintained at a decreased level for up to 4 hours (FIGS. 4D-4E). This down-modulatory trend was once again induced for up to 48 hours and was recovered by 72 hours (FIGS. 4D-4E). In the NECA-treatment group, the expression level of P-gp began to decrease at 30 minutes and was maintained for up to 48 hours and recovered by 72 hours (FIGS. 5D-5E). This was recapitulated in the Rho123 uptake assay, which showed that Lexiscan® rapidly suppressed P-gp function beginning at 15 minutes and that this was maintained for up to 90 minutes (FIG. 4F). NECA showed a trend in P-gp suppression, but it did not reach statistical significance (FIG. 5F).

Figures 6A, 6B, 6C, 6D, 6E, 6F:
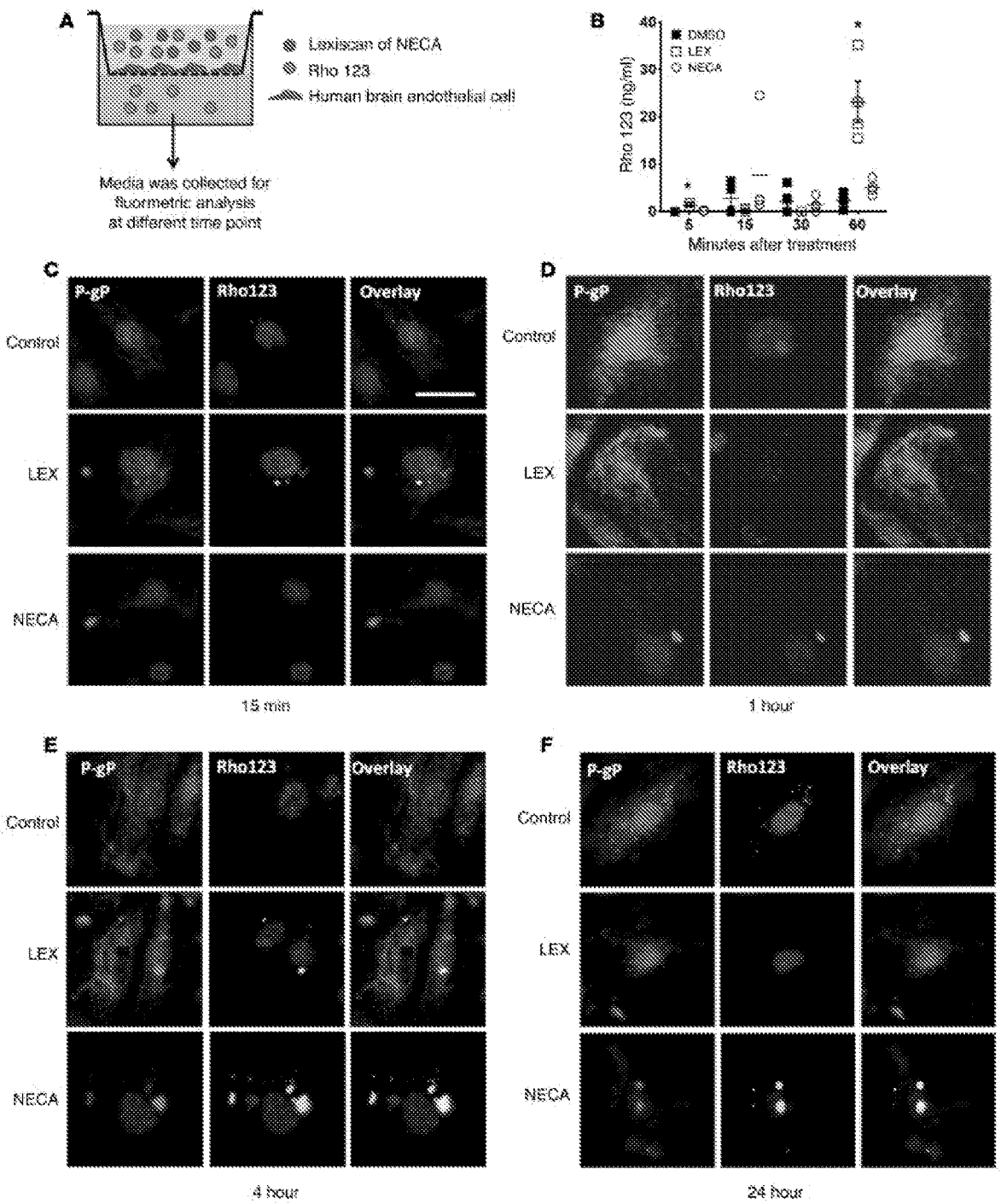
FIGS. 6A-6F are a schematic, fluorescence microscopy images, and a graph of experimental results showing that the activation of A2A AR by Lexiscan® induces rapid transmigration of Rho123 across an in vitro human BBB and accumulation of Rho123 in primary brain endothelial cell.
Figure 7:
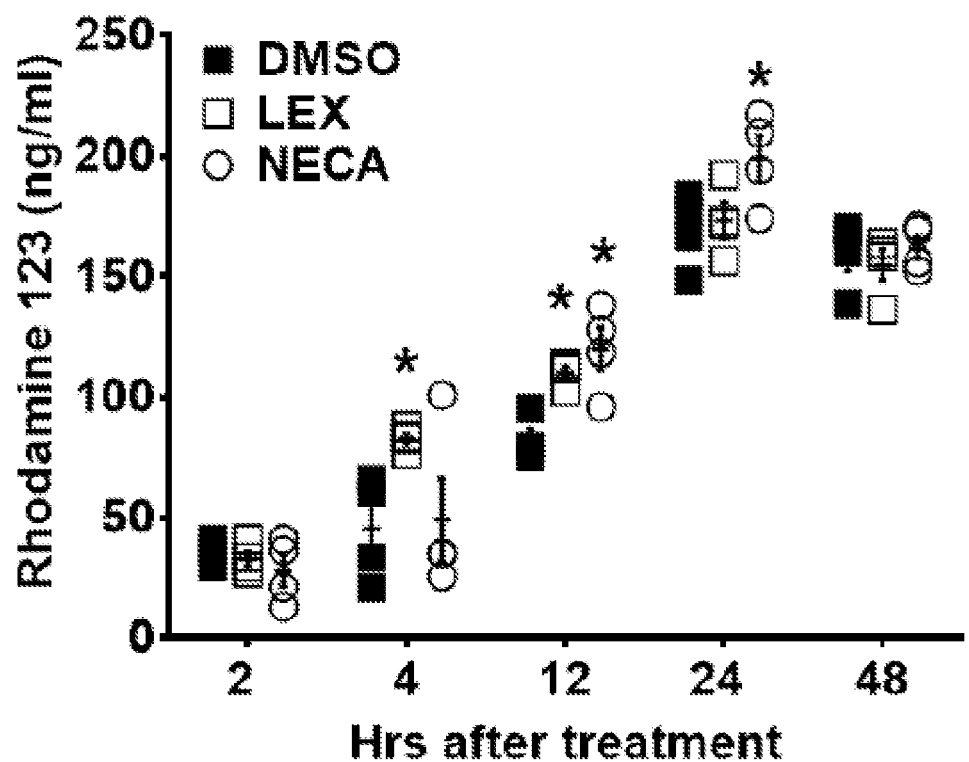
FIG. 7 is a summarizes experimental results that show that broad spectrum AR activation increases transmigration of Rho123 in primary human brain endothelial cells at later time points. In vitro blood brain barrier models were generated using primary human brain endothelial cells cultured on a porous membrane to evaluate Rho123 migration cross the BBB. Cells grown on porous membrane were treated with Lexiscan® (0.25 µM) or NECA (0.02 µM) concomitantly with 2.5 µM of Rho123 and concentration of Rho123 at the bottom chambers was analyzed at 2, 4, 12, 24, and 48 hours after treatment by fluorometry, with excitation at 488 nm and emission at 523 nm * Indicates values where P<0.05 (n=4, two tailed student t-test, one representative result of three different experiments).

Whether P-gp down-regulation results in substrate accumulation was next evaluated using a transmigration assay using primary human brain endothelial cells (experimental procedure described in FIG. 6A). Lexiscan® induced rapid increase in permeability to Rho123 beginning at 5 minutes, and this lasted for up to 60 minutes (FIG. 6B). Rho123 levels returned to steady state by 2 hours; they increased again by 4 hours, and this was maintained at steady state for up to 12 hours (FIG. 7). NECA's effect on Rho123 levels occurred at 12 hours and was maintained for up to 24 hours (FIGS. 6B, 7). To further dissect the effect of AR signaling on the functionality of P-gp and Rho123 accumulation in primary human brain endothelial cells, endothelial cells were treated with Rho123 with or without Lexiscan®, and Rho123 accumulation was visualized by IFA at different time points. Lexiscan® increased the accumulation of Rho123 beginning at 15 minutes to 1 hour. NECA treatment increased Rho123 accumulation at later time points, beginning at 4 hours; this was maintained for up to 24 hours (FIGS. 6C-6F). These results indicate that NECA treatment also increased Rho123 accumulation in primary human brain endothelial cells, as shown by IFA. Overall, these results indicate that activation of A2A AR by Lexiscan® potently and rapidly increases the transcellular permeability in human brain endothelial cells in a reversible manner. While NECA exhibited similar effects, its permeability kinetics occurred later and its effects were less potent than Lexiscan's. These results indicate that A2A AR activation has a potent effect on P-gp expression and function and that this effect occurs rapidly with Lexiscan® treatment and may involve multiple mechanisms of regulation.

Figures 8A, 8B, 8C, 8D, 8E, 8F, 8G, 8H:
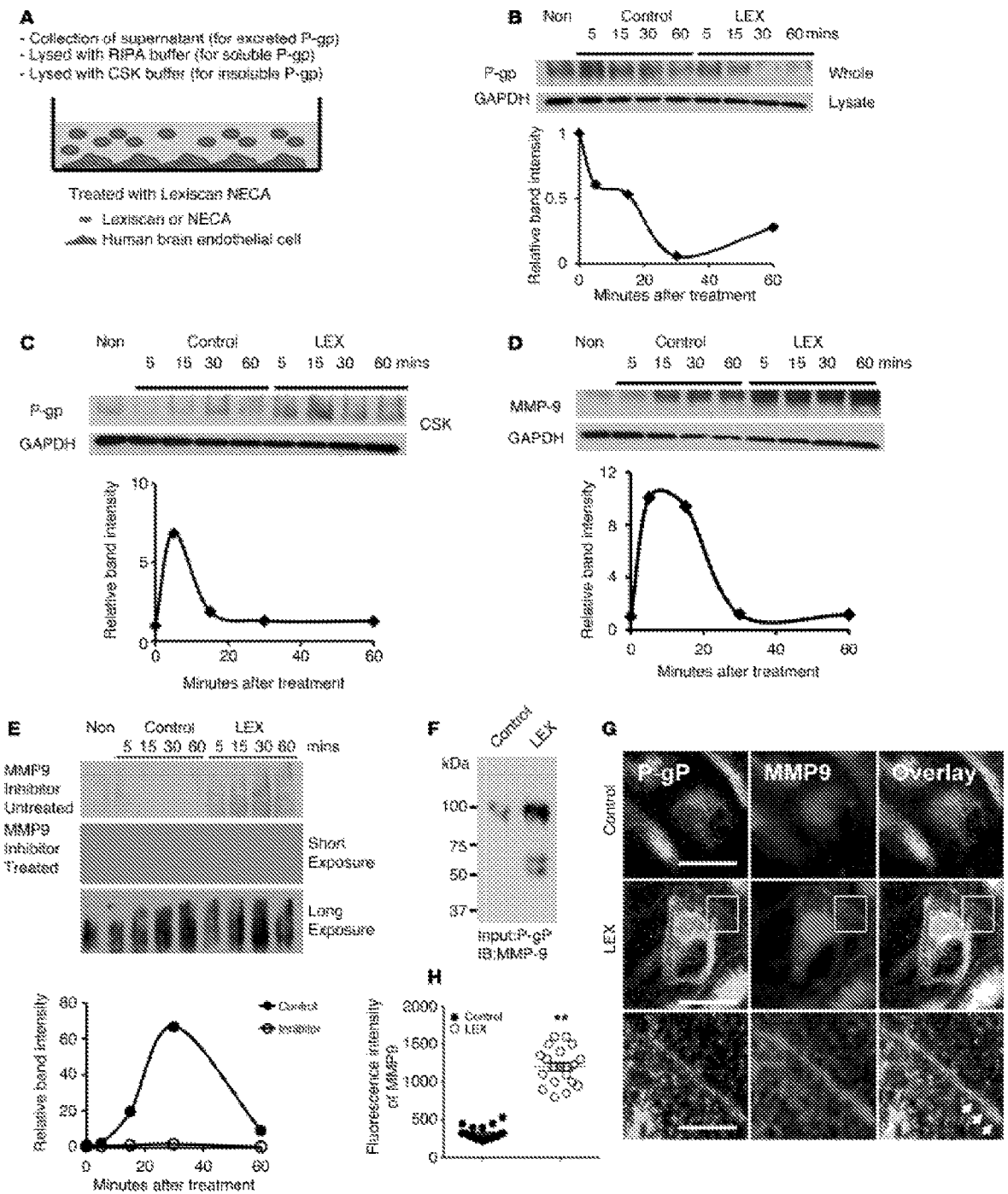
FIGS. 8A-8H show that P-gp down-modulation by Lexiscan® is mediated by MMP9 cleavage and translocation to insoluble cytoskeletal fractions.

Example 3—P-gp Down-Modulation by Lexiscan® is Mediated by Activation of MMP9, Ubiquitination, and Translocation to the Cytoskeletal Fraction To better understand the mechanism behind the rapid down-modulation of P-gp observed after Lexiscan® treatment, CSK buffer, which extracts insoluble cytoskeletal materials, was used to determine whether P-gp is contained in the insoluble fraction, as this might explain its rapid down-modulation upon Lexiscan® treatment (experimental procedure described in FIG. 8A). Comparison of P-gp expression levels in cytoskeletal fraction to P-gp in whole lysate showed increased P-gp in the cytoskeletal fraction compared with control (FIGS. 8B-8C). In cytoskeletal fraction, P-gp levels increased at from 5 to 15 minutes, returned to baseline by 30 minutes, and were maintained at baseline level for up to 60 minutes (FIG. 8C). In contrast, in whole lysate, P-gp levels declined compared with vehicle control beginning at 5 minutes and were maintained for up to 60 minutes (FIG. 8B). Activation of A2A AR is known to induce the relocalization of targets such as tyrosine receptor kinase β to the insoluble fraction (Mundell et al., "Adenosine Receptor Desensitization and Trafficking," *Biochim. Biophys. Acta* 1808(5):1319-1328 (2011) and Lasley R. D., "Adenosine Receptors and Membrane Microdomains," *Biochim. Biophys. Acta.* 1808(5):1284-1289 (2011), which are hereby incorporated by reference in their entirety). It is possible that P-gp in the soluble fraction may have been translocated to the cytoskeletal fraction by A2A signaling at an early time point, which may explain the rapid decrease in P-gp levels upon Lexiscan® treatment.

Figure 9:
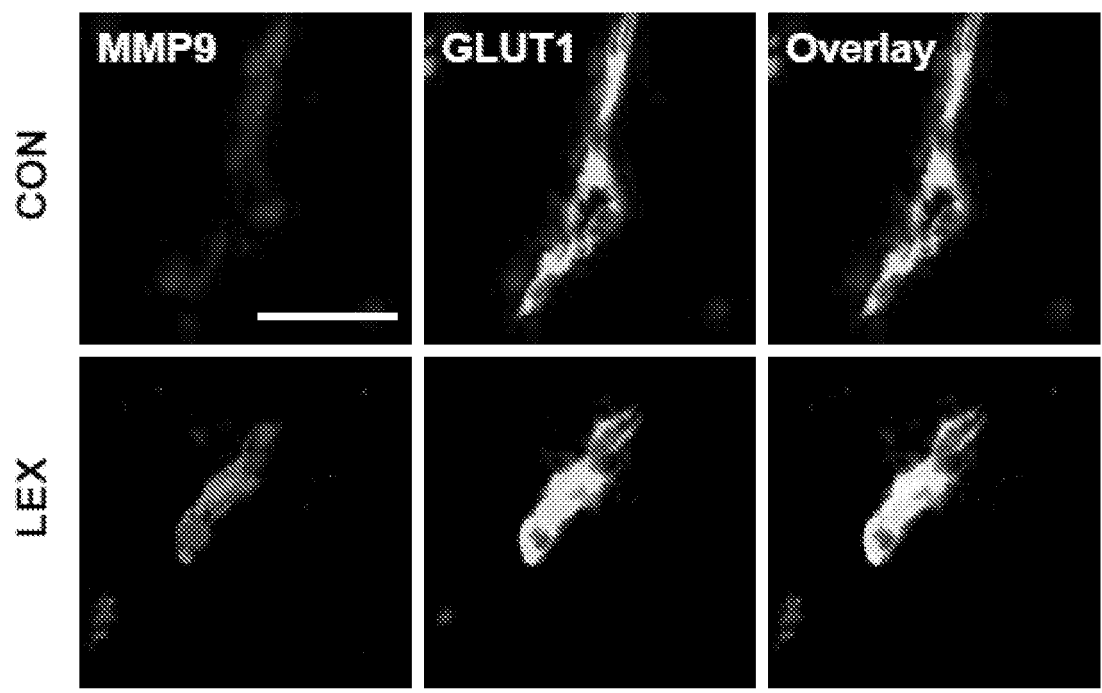
FIG. 9 is a fluorescence microscopy image showing that A2A AR activation induces a rapid increase of MMP9 in mouse brain endothelial cells. Vehicle control (DMSO) or 0.05 mg/kg of Lexiscan® was injected intravenously into mice. Five minutes later, mice were sacrificed and frozen sections of the brain were stained with anti-MMP9 (red) or anti-GLUT-1 (green) antibodies. Nucleus was counterstained with DAPI (blue). The scale bar indicates 50 µm.

Whether MMP9, which can be induced by various ARs and degrades extracellular matrix molecules, may become activated and cleave P-gp, resulting in its rapid decrease upon Lexiscan® treatment was next investigated (Velot et al., "Activation of the Adenosine-A3 Receptor Stimulates Matrix Metalloproteinase 9 Secretion by Macrophages," *Cardiovasc. Res.* 80(2):246-254 (2008) and Chen et al., "Regulation of MMP-9 Expression by the A2b Adenosine Receptor and Its Dependency on TNF-α Signaling," *Exp. Hematol.* 39(5):525-530 (2011), which are hereby incorporated by reference in their entirety). Increased expression of MMP9 was observed beginning at 5 minutes that matched the same kinetics of P-gp decrease by western blot and IFA (FIGS. 8D, 8G, 8H), which was also observed in mouse brain endothelial cells (FIG. 9). An increase in secreted P-gp that was released into the media with kinetics similar to those found in MMP9 expression was also observed. This secreted MMP9 was suppressed by an MMP9-specific inhibitor (FIG. 8E), indicating that secretion of P-gp was mediated by MMP9. Immunoprecipitation assay and IFA showed that A2A AR activation by Lexiscan® induced rapid interaction between P-gp and MMP9, indicating possible cleavage of P-gp by MMP9 at early time points (FIG. 8F-8G). Interestingly, the colocalization of P-gp with MMP9 at the cell surface was increased compared with its control, indicating that P-gp cleavage occurred at the cell surface and that the cleaved P-gp is secreted into the extracellular space (FIG. 8G). This indicates that MMP9 is at least in part responsible for the early and rapid decrease in P-gp levels upon Lexiscan® treatment (FIG. 8B).

Figures 10A, 10B, 10C:
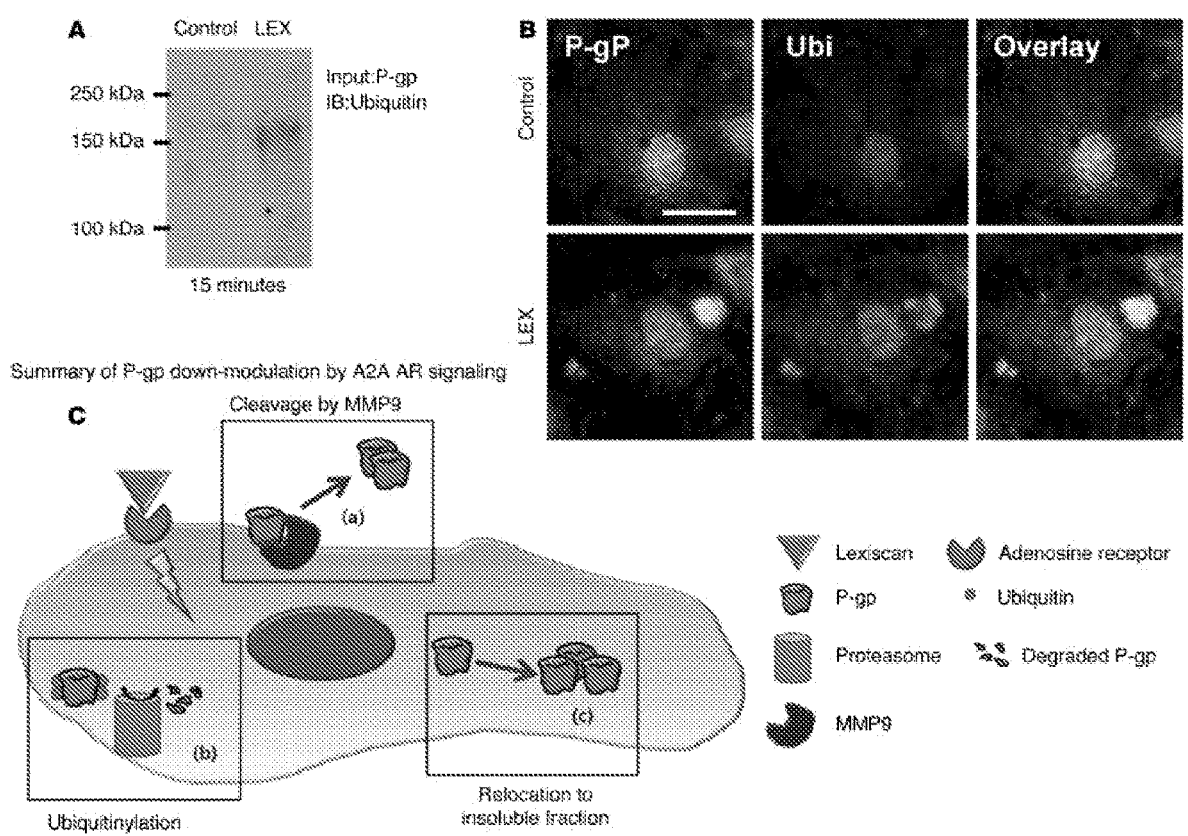
FIGS. 10A-10C show that P-gp down-modulation by Lexiscan® is also mediated by ubiquitination.

Next, whether A2A AR activation by Lexiscan® can activate ubiquitination of P-gp, which was reported as one of the mechanisms that regulates P-gp expression (Zhang et al., "Regulation of the Stability of P-Glycoprotein by Ubiquitination," *Mol. Pharmacol.* 66(3):395-403 (2004), which is hereby incorporated by reference in its entirety) and thereby results in its rapid decrease, was investigated. Primary human brain endothelial cells were treated with Lexiscan® for 15 minutes; immunoprecipitation of P-gp was performed, and the eluent was immunoblotted against an antibody for ubiquitin. The result showed that treatment of primary human brain endothelial cells with Lexiscan® for 15 minutes induced increased ubiquitinylation of P-gp compared with vehicle control (FIG. 10A). This was further captured by strong colocalization of P-gp with ubiquitin after 15 minutes of treatment of primary human brain endothelial cells with Lexiscan®, further indicating that Lexiscan® can induce rapid ubiquitination of P-gp, which helps to explain its rapid down-modulation by Lexiscan® stimulation (FIG. 10B). Overall, these data indicate that the rapid decrease in P-gp expression by Lexiscan® may be mediated by several different pathways operating sequentially, independently, or simultaneously (proposed model, FIG. 10C).

Figures 11A, 11B, 11C, 11D:
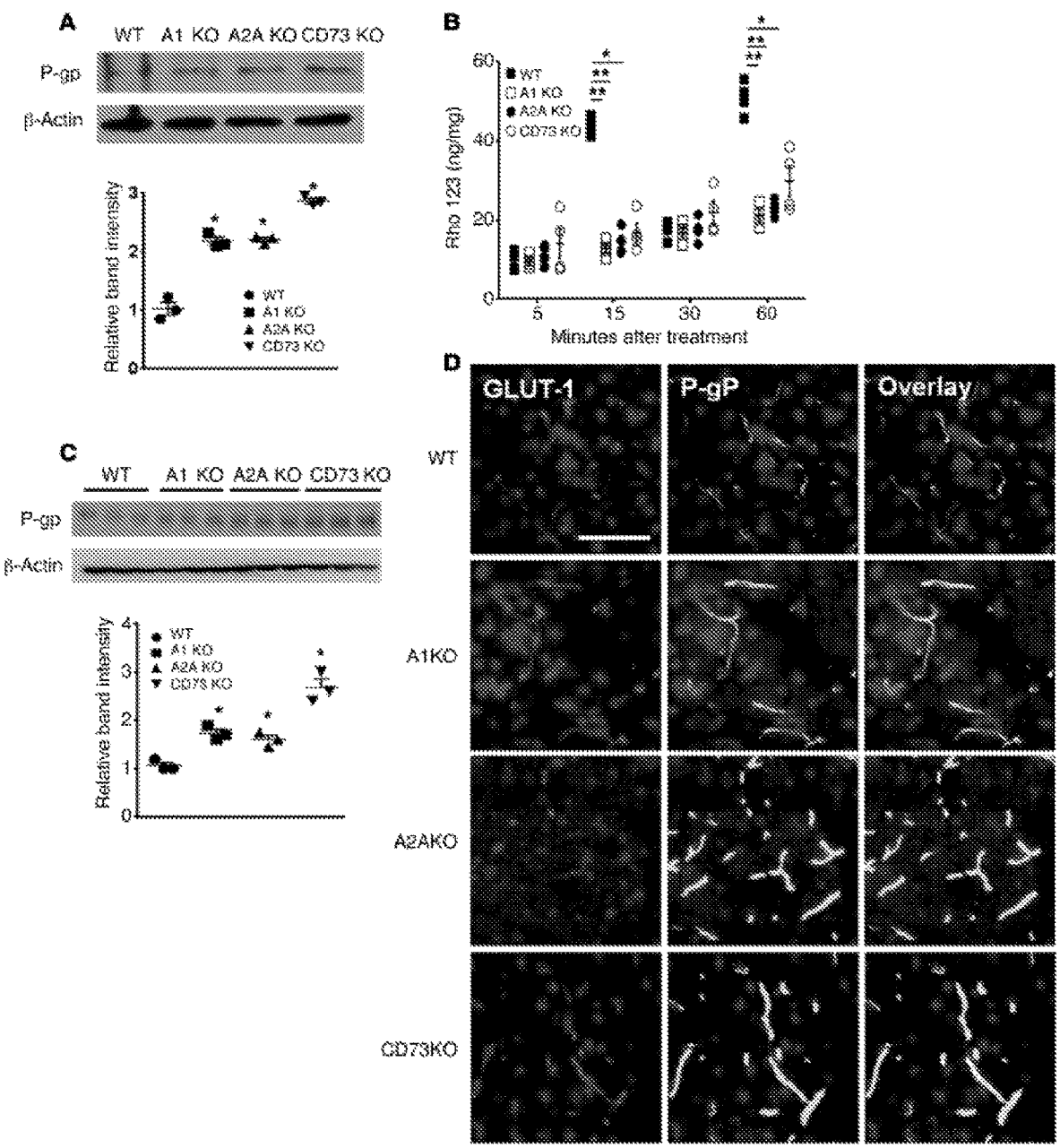
FIGS. 11A-11D show that ablation of CD73 or ARs increases P-gp expression and decreases P-gp substrate accumulation in the brain.

Example 4—Ablation of CD73 or ARs Increased P-gp Expression and Decreased P-gp Substrate Accumulation in the Brain Whether signaling via the A2A AR regulates P-gp expression and functionality in the mouse brain was next investigated. First, primary brain endothelial cells from brains of mice with genetic deletion of A1 (Adora1$^{-/-}$), A2A AR (Adora2a$^{-/-}$), or CD73 (Cd73$^{-/-}$) were examined to determine whether P-gp expression was altered in their absence compared with WT mice. Increased expression of P-gp was observed in primary brain endothelial cells from A1 KO, A2A KO, or CD73 KO mice compared with WT controls (FIG. 11A). Moreover, significant decreases in the accumulation of P-gp substrate Rho123 in primary brain endothelial cells was observed (FIG. 11B). Next, whether increased P-gp is observed in the endothelial cells within the brains of these KO animals was investigated. A2A AR and CD73 KO animals showed stronger P-gp signals than A1 AR KO mice, which showed P-gp expression similar to that of WT mice. These results indicate that extracellular adenosine acting through its A2A receptor is the major signaling component involved in P-gp expression/function (FIGS. 11C-11D).

Example 5—AR Activation Down-Modulates P-gp Expression and Function in WT Mice

Figures 12A, 12B, 12C, 12D, 12E:
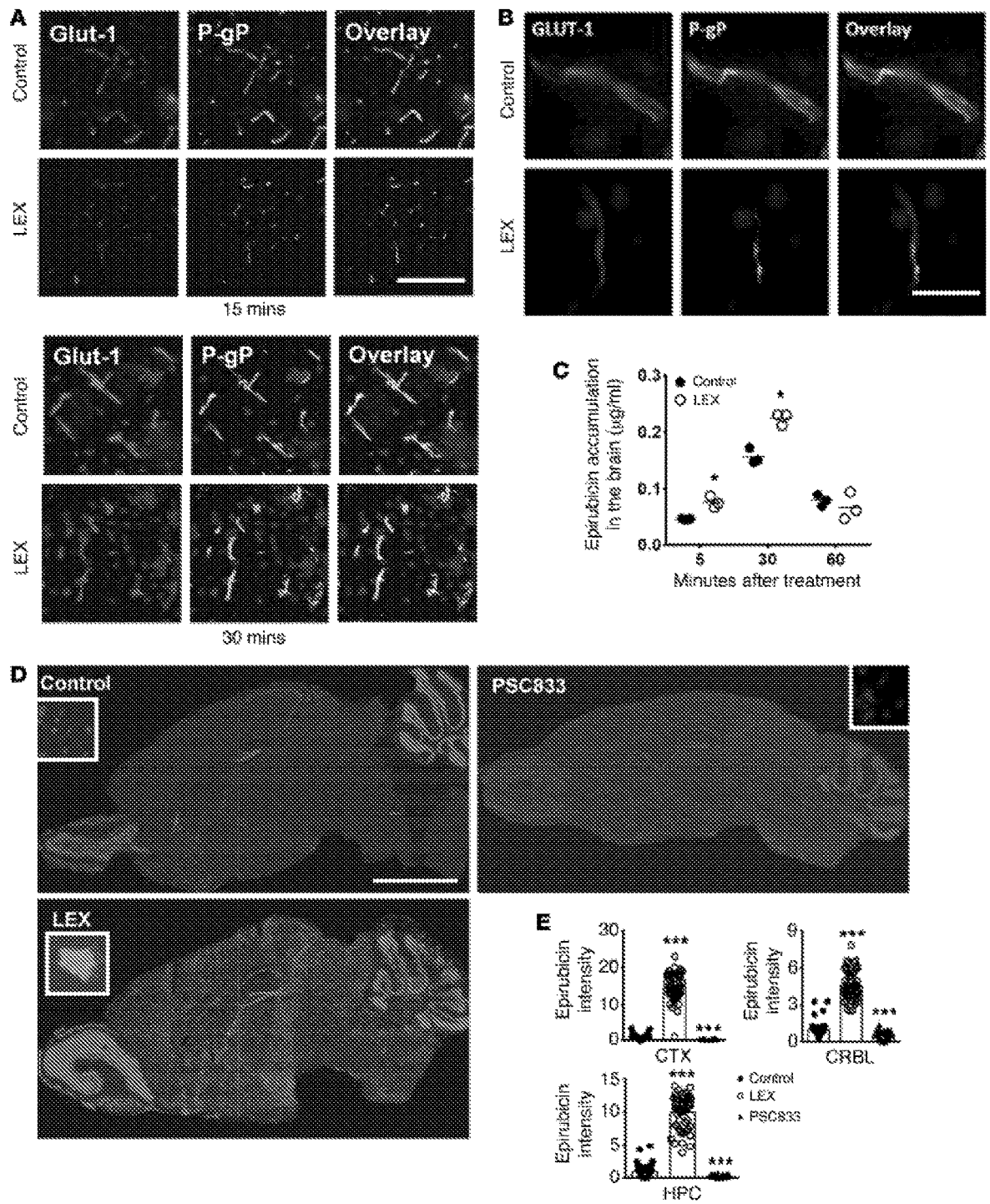
FIGS. 12A-12E show that A2A receptor activation by Lexiscan® induces rapid and reversible down-modulation of P-gp expression and function in brain vascular endothelial cells in WT mice.
Figure 13A:
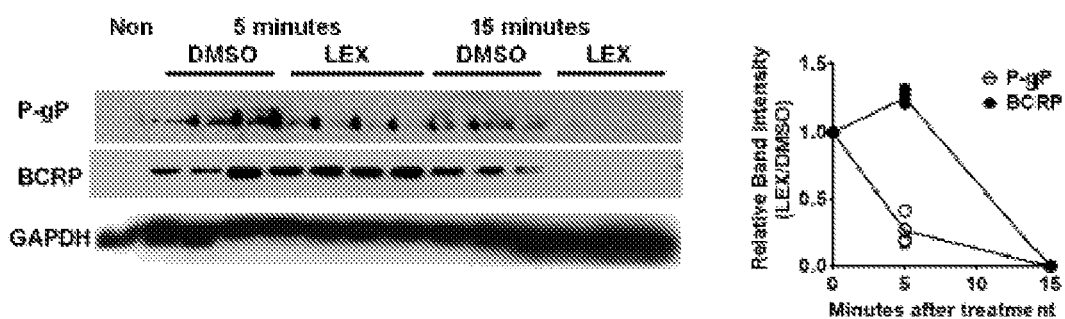
FIGS. 13A-13C shows that A2A activation by Lexiscan® induces rapid and reversible down-modulation of P-gp and BCRP1 expression.
Figure 13B:
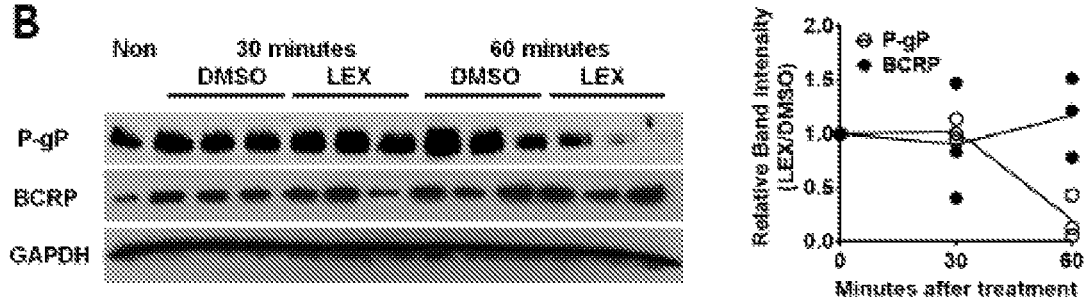
Figure 13C:
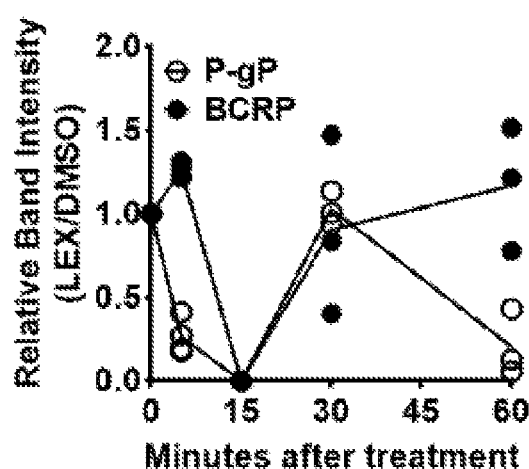

Whether activation of A2A AR with Lexiscan® or NECA could downregulate P-gp expression with concomitant increase in drug accumulation in the brains of WT mice was next investigated. Lexiscan® treatment decreased P-gp expression in brain endothelial cells in WT mice between 5 and 15 minutes; this was recovered by 30 minutes, as shown by western blot analysis (FIGS. 11A-11C) and IFA (FIG. 12A-12B). To assess whether A2A AR activation may have similar down-modulatory effects on other transporters expressed on brain endothelial cells, next the expression level of BCRP1/ABCG2, which is another key drug transporter highly expressed in many tissues, including the CNS vasculature, was determined by western blot. Lexiscan® treatment potently down-regulated BCRP expression by 15 minutes, after which its expression began to recover by 60 minutes (FIGS. 11A-11C). This result indicates that activation of A2A AR can alter BCRP expression/function. It is notable that Lexiscan®'s effect on P-gp occurred within 5 minutes compared with 15 minutes for BCRP. This result indicates that A2A AR signaling effects on BCRP1 may be less sensitive compared with its effects on P-gp. To test whether these changes in P-gp expression in WT mice directly affect the functionality of P-gp and its substrate accumulation in the brain, the autofluorescent chemotherapeutic drug epirubicin was used, which allowed applicants to map its location and quantify its accumulation in the brain by fluorometry. Consistent with P-gp down-modulation, epirubicin accumulation in the brains of Lexiscan®-treated mice began to increase at 5 minutes; this was maintained up to 30 minutes and returned to baseline by 60 minutes (FIG. 12C). This kinetic profile of P-gp down-modulation (FIGS. 13A-13C) matched exactly with the kinetics of epirubicin accumulation in the brain (FIG. 12C). Despite obtaining statistically significant epirubicin values in Lexiscan®-treated mice, these values did not appear to match the fluorescent intensity of epirubicin observed in the brains of Lexiscan®-treated mice (FIG. 12D). Using a scanning scope, the entire brain of mice treated with epirubicin with or without Lexiscan® were captured to visualize where epirubicin is accumulated in the brain and to quantify where it is localized (FIG. 12D). Lexiscan® treatment increased the accumulation of epirubicin prominently in the cerebral cortex, the cerebellum, and brain stem, and, to a lesser degree, in the olfactory bulb and hippocampus (FIG. 12D). Next, the fluorescent intensity of specific areas in the brain were quantified to be compared with controls. Significant epirubicin intensity in the cerebral cortex, the cerebellum, and the hippocampus was observed in Lexiscan®-treated mice compared with control mice that received vehicle and epirubicin (FIGS. 12D-12E). This result indicated that substantially more epirubicin accumulated in brain tissue of Lexiscan®-treated mice than what applicants were able to extract (FIG. 12C). To assess the inhibitory capacity of Lexiscan® on P-gp in BBB permeability, applicants compared it to that of a well-known functional inhibitor of P-gp, PSC833, by measuring the intensity of epirubicin accumulation in the brain after PSC833 or Lexiscan® treatment. Significantly lower epirubicin intensity was observed in the brains of mice treated with PSC833 compared with Lexiscan®-treated mice (FIGS. 12D-12E). Moreover, the PSC833 treatment group exhibited lower epirubicin intensity than even the control treatment group (FIGS. 12D-12E). This indicates that Lexiscan® is a more potent inhibitor of P-gp than PSC833 (Mayer et al., "Full Blockade of Intestinal P-Glycoprotein and Extensive Inhibition of Blood-Brain Barrier P-Glycoprotein by Oral Treatment of Mice With PSC833," *J. Clin. Invest.* 100(10):2430-2436 (1997), which is hereby incorporated by reference in its entirety). Based on these observations, it is proposed that A2A AR activation by Lexiscan® rapidly and potently decreased P-gp expression and function, resulting in the accumulation of a P-gp substrate (epirubicin) in the brain.

Figures 14A, 14B, 14C, 14D:
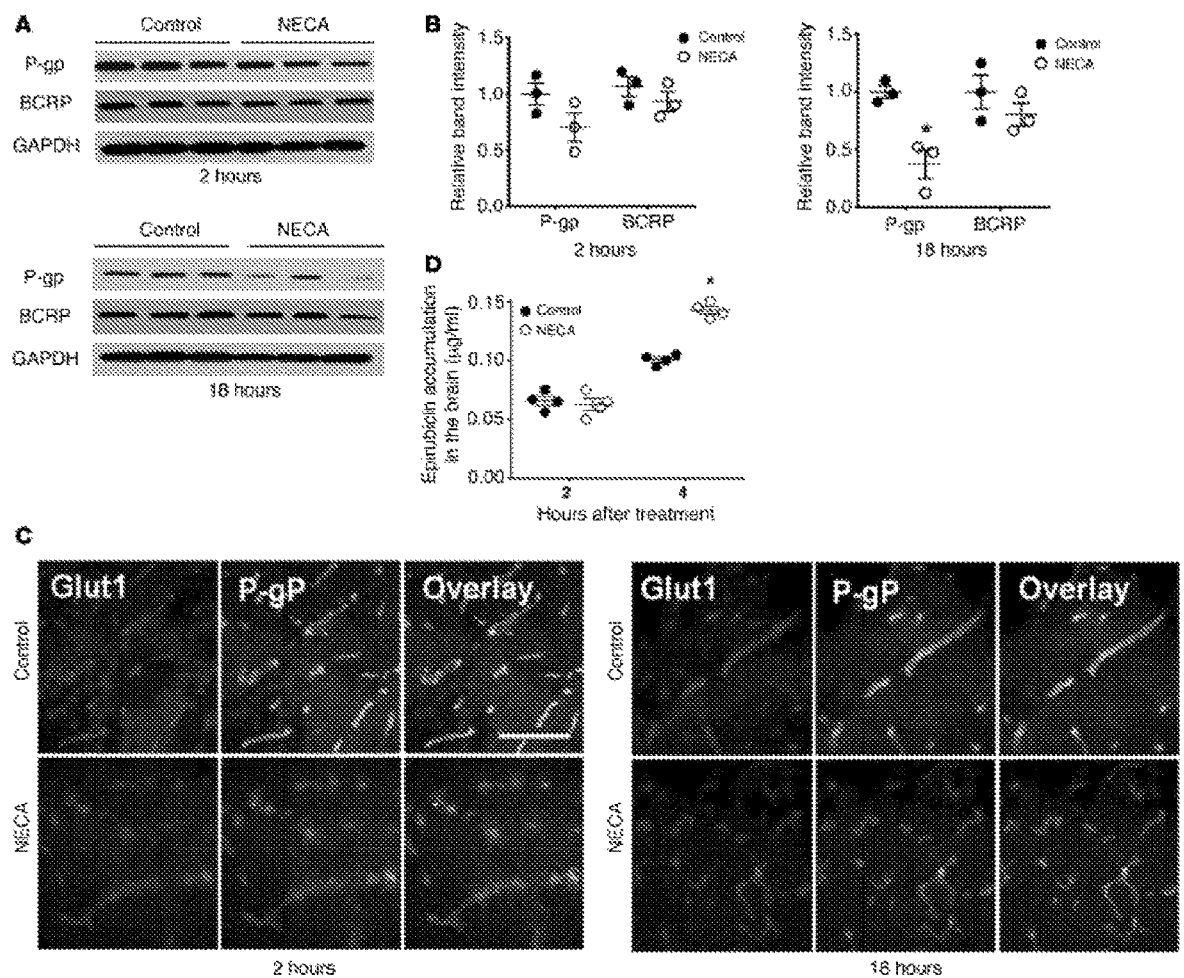
FIGS. 14A-14D show that the broad-spectrum AR agonist NECA induces gradual and delayed down-modulation of P-gp expression and function in brain vascular endothelial cells in WT mice.
Figure 15:
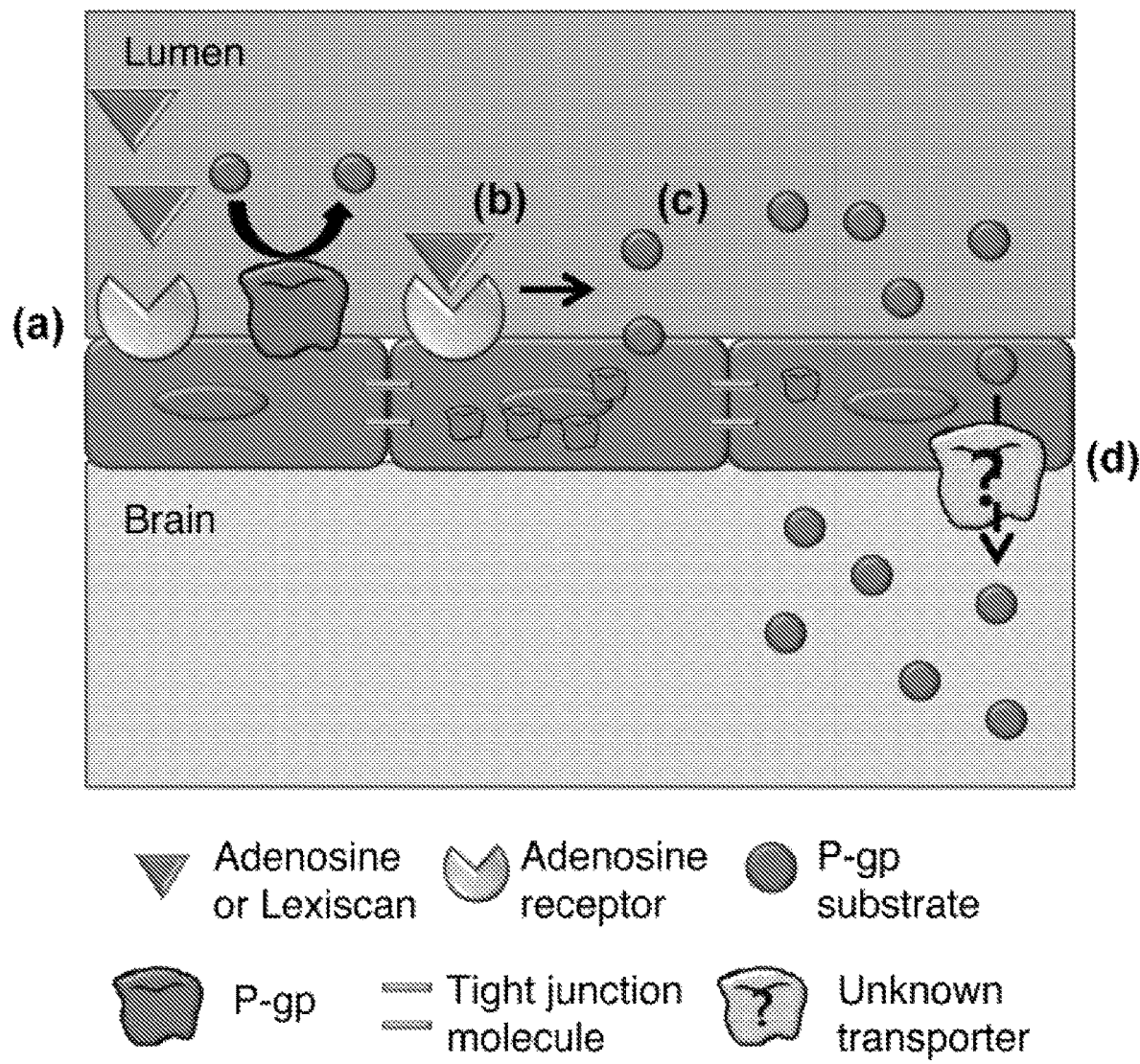
FIG. 15 is a schematic showing the mechanism of regulation of transcellular permeability by A2A AR signaling. (a) In basal status, single layer of brain endothelial cells highly express transporters including P-gp. (b) When AR is activated by adenosine or Lexiscan®, (c) it downregulates P-gp on brain endothelial cells (d), which increases transcellular permeability and delivery of P-gp substrate into the brain.

The effect of NECA treatment on BCRP expression was compared with its effects on P-gp in brains of WT mice. NECA induced a gradual decrease in P-gp expression level, beginning at 2 hours; this was maintained for up to 18 hours, whereas the expression level of BCRP was not significantly affected (FIGS. 14A-14C). The effect of NECA on P-gp down-modulation in BBB permeability to entry and accumulation of epirubicin in the brain was examined. NECA-treated animals showed epirubicin accumulation in the brain that matched the kinetics of P-gp decrease in endothelial cells in the brain (FIGS. 14B, 14D). Interestingly, the kinetics of epirubicin accumulation in the brain induced by Lexiscan® and NECA were very similar to the time window of P-gp down-modulation in human primary brain endothelial cells in vitro (FIGS. 4D, 6D). Based on these findings, applicants conclude that signaling via the A2A AR on brain endothelial cells increases the transcellular pathway mediated by P-gp (summarized in FIG. 15). Examples 1-5 provide a compelling case for adenosine signaling via the A2A receptor in P-gp regulation that in the future may inform drug delivery to the CNS.

Discussion of Examples 1-5

The BBB is necessary to protect the brain and maintain its homeostasis (Abbott N. J., "Astrocyte-Endothelial Interactions and Blood-Brain Barrier Permeability," *J. Anat.* 200 (6):629-638 (2002); Deeken et al., "The Blood-Brain Barrier and Cancer: Transporters, Treatment, and Trojan Horses," *Clin. Cancer Res.* 13(6):1663-1674 (2007); and Pardridge W. M., "The Blood-Brain Barrier: Bottleneck in Brain Drug Development," *NeuroRx* 2(1):3-14 (2005), which are hereby incorporated by reference in their entirety). However, its restrictive nature hampers the ability to get therapeutics into the brain Deeken et al., "The Blood-Brain Barrier and Cancer: Transporters, Treatment, and Trojan Horses," *Clin. Cancer Res.* 13(6):1663-1674 (2007) and Pardridge W. M., "The Blood-Brain Barrier: Bottleneck in Brain Drug Development," *NeuroRx* 2(1):3-14 (2005), which are hereby incorporated by reference in their entirety). As the world population lives longer, the trend in neurodegenerative diseases increases, especially AD (Pardridge W. M., "The Blood-Brain Barrier: Bottleneck in Brain Drug Development," *NeuroRx* 2(1):3-14 (2005), which is hereby incorporated by reference in its entirety). Billions of dollars are spent on drug development to bypass the BBB or to modify drugs such that they would have easier access in traversing the BBB, which blocks the delivery of the vast majority of drugs to the brain. After millions to billions of dollars are spent on developing these drugs, many of them are dropped from the pipeline, as they do not show efficacy or are too large to pass the BBB.

Cells and soluble molecules enter the brain through paracellular or transcellular pathways that are mediated by cell-to-cell junction or transporters, respectively (Abbott N. J., "Astrocyte-Endothelial Interactions and Blood-Brain Barrier Permeability," *J. Anat.* 200(6):629-638 (2002) and Pardridge W. M., "The Blood-Brain Barrier: Bottleneck in Brain Drug Development," *NeuroRx* 2(1):3-14 (2005), which are hereby incorporated by reference in their entirety). A variety of transporters and receptors are highly expressed on brain endothelial cells that selectively restrict or allow the entry of substances, some of which are necessary for normal brain function, such as glucose and amino acids, while others are expelled (Pardridge W. M., "The Blood-Brain Barrier: Bottleneck in Brain Drug Development," *NeuroRx* 2(1):3-14 (2005) and Jodoin et al., "P-Glycoprotein in Blood-Brain Barrier Endothelial Cells: Interaction and Oligomerization With Caveolins," *J. Neurochem.* 87(4):1010-1023 (2003), which are hereby incorporated by reference in their entirety).

Molecules enter the CNS by transcellular and/or paracellular routes and the transcellular pathway is regulated by efflux transporters, such as P-gp (Deeken et al., "The Blood-Brain Barrier and Cancer: Transporters, Treatment, and Trojan Horses," *Clin. Cancer Res.* 13(6):1663-1674 (2007); Daneman et al., "The Blood-Brain Barrier," *Cold Spring Harb. Perspect. Biol.* 7(1): a020412 (2015); and Chung et al., "P-Glycoprotein: The Intermediate End Point of Drug Response to Induction Chemotherapy in Locally Advanced Breast Cancer," *Breast Cancer Res. Treat.* 42(1):65-72 (1997), which are hereby incorporated by reference in their entirety). Not surprisingly, many drugs are expelled by P-gp even before entering the brain and therefore are dropped from the drug pipeline in the course of their development (Begley D. J., "ABC Transporters and the Blood-Brain Barrier," *Curr. Pharm. Des.* 10(12):1295-1312 (2004), which is hereby incorporated by reference in its entirety). This poses tremendous economic loss and obstacles for public health, in particular, for treatment of CNS diseases Deeken et al., "The Blood-Brain Barrier and Cancer: Transporters, Treatment, and Trojan Horses," *Clin. Cancer Res.* 13(6):1663-1674 (2007); Daneman et al., "The Blood-Brain Barrier," *Cold Spring Harb. Perspect. Biol.* 7(1): a020412 (2015); and Schinkel A. H., "P-Glycoprotein, A Gatekeeper in the Blood-Brain Barrier," *Adv. Drug Deliv. Rev.* 36(2-3): 179-194 (1999), which are hereby incorporated by reference in their entirety). Hence, it is imperative and urgent to better understand how these processes operate.

Previous studies showed that activation of the A2A AR increases BBB permeability to entry of large molecules that is mediated by increased paracellular permeability, induced RhoA activity, and rearrangement of the actin-cytoskeleton in brain endothelial cells (Kim et al., "A2A Adenosine Receptor Regulates the Human Blood-Brain Barrier Permeability," *Mol. Neurobiol.* 52(1):664-678 (2014) and Carman et al., "Adenosine Receptor Signaling Modulates Permeability of the Blood-Brain Barrier," *J. Neurosci.* 31(37):13272-13280 (2011), which are hereby incorporated by reference in their entirety). Previous studies have also shown that: (i) BBB opening under AR signaling is reversible; (ii) the duration of BBB permeability is dependent on the half-life of the AR agonist; (iii) activation of AR signaling exerts its effects on the paracellular pathway by altering VE-cadherin and claudin-5 expression to promote BBB permeability in human primary brain endothelial cells; and (iv) activation of AR signaling with Lexiscan® or 5'-N-ethylcarboxamidoadenosine ("NECA") mediates BBB permeability by Rho-GTPase modulation (Carman et al., "Adenosine Receptor Signaling Modulates Permeability of the Blood-Brain Barrier," *J. Neurosci.* 31(37):13272-13280 (2011) and Kim et al., "A2A Adenosine Receptor Regulates the Human Blood-Brain Barrier Permeability," *Mol. Neurobiol.* 52(1):664-678 (2014), which are hereby incorporated by reference in their entirety).

However, this is the first investigation to demonstrate the unexpected role of ARs in modulating drug efflux proteins (e.g., P-gp) and controlling transcellular permeability in brain endothelial cells, as well as in cell types found outside of the brain and CNS.

Examples 1-5 describe the use of a human brain endothelial cell line and primary human and mouse brain endothelial cells as in vitro models to investigate the impact of AR signaling on P-gp function and examine whether said in vitro data can be recapitulated in vivo in mice. The in vitro data show that activation of AR significantly and potently alters P-gp expression/function. P-gp expression was rapidly down-modulated in both primary human and mouse brain endothelial cells and in a human brain endothelial cell line by activation of A2A AR with Lexiscan® treatment. In NECA treatment, down-modulation of P-gp occurred later than that of Lexiscan®. The difference in both Lexiscan® and NECA's effects result from the difference in their half-lives: Lexiscan®'s half-life is approximately 2.5 minutes, whereas NECA's is 5 hours. The down-modulation of P-gp by AR activation strikingly correlates with P-gp function that was confirmed by Rho123 accumulation and extravasation assays in primary human brain endothelial cells.

Because the experimental results of Examples 1-5 show a potent and rapid down-modulation of P-gp that occurred over multiple time points after Lexiscan® treatment of primary human brain endothelial cells, it was hypothesized that AR activation regulates P-gp expression and function by multiple mechanisms. The molecular mechanism behind the rapid down-modulation of P-gp was investigated. In a cyto-skeletal fractionation assay, a significant amount of P-gp was found in the insoluble fraction upon Lexiscan® treatment of primary human brain endothelial cells. Moreover, secreted P-gp in was observed in brain endothelial cell culture supernatants, indicating that P-gp is cleaved and released into the extracellular environment. Consistent with this notion, a concomitant increase in MMP9 levels were observed that suggests that MMP9 may also be involved in down-modulation of P-gp upon AR activation. Moreover, the interaction between MMP9 and P-gp was found to increase upon AR activation by immunoprecipitation assay and IFA, suggesting the cleavage of P-gp by MMP9 induces secretion of P-gp into the extracellular space. It is also reported that P-gp is regulated by ubiquitination (Zhang et al., "Regulation of the Stability of P-Glycoprotein by Ubiquitination," *Mol. Pharmacol.* 66(3):395-403 (2004), which is hereby incorporated by reference in its entirety). In support of this, rapid ubiquitinylation of P-gp by Lexiscan® both by IFA and immunoprecipitation analysis was observed. Together, these findings indicate that A2A AR-mediated regulation of P-gp expression/function occurs by these mechanisms independently or in combination.

Consistent with the in vitro findings of Examples 1-5, AR activation was observed to exert similar effects on P-gp expression and function in vivo. In mouse brain endothelial cells, Lexiscan®'s effects on P-gp were rapid, occurring within 5 minutes, whereas the effect of NECA was observed 2 hours later. A2A AR activation also exerted its effects on BCRP1 expression/function as potently as it did on P-gp. This indicates that both P-gp and BCRP1, which have been previously shown to function cooperatively, are regulated by A2A AR. A noted difference is that Lexiscan®'s effects on BCRP1 occurred 10 minutes later than its effects on P-gp. Thus, it is possible that P-gp activity may be more sensitive to A2A AR regulation than that of BCRP1. However, a more thorough study of BCRP1 regulation by A2A AR would be required to make this determination. As proof of principle that AR activation causes P-gp down-modulation, resulting in increased accumulation of P-gp substrates, the effects of Lexiscan® treatment on the accumulation of the chemo-therapeutic drug epirubicin, which is a P-gp substrate, were examined. AR activation increased the accumulation of epirubicin in the brain that coincides with the kinetics of P-gp down-modulation. Consistent with the observation in vitro in human brain endothelial cells, Lexiscan®'s effect on accumulation of epirubicin was rapid, whereas NECA's was gradual. This difference in permeability kinetics between the 2 agonists stems from differences in their half-lives (Lexiscan®, 2.5 minutes; NECA, 5 hours).

P-gp has long posed a tremendous hindrance to drug delivery to the brain and across the biological barrier in general (Pardridge W. M., "Drug Transport Across the Blood-Brain Barrier," *J. Cereb. Blood Flow Metab.* 32(11): 1959-1972 (2012) and Schinkel A. H., "P-Glycoprotein, A Gatekeeper in the Blood-Brain Barrier," *Adv. Drug Deliv. Rev.* 36(2-3):179-194 (1999), which are hereby incorporated by reference in their entirety). This molecule functions by expelling drugs and xenobiotics from cells, and it alters drug pharmacokinetics (Aller et al., "Structure of P-Glycoprotein Reveals a Molecular Basis for Poly-Specific Drug Binding," *Science* 323(5922):1718-1722 (2009), which is hereby incorporated by reference in its entirety). Its broad substrate spectrum allows it to expel major classes of drugs (Aller et al., "Structure of P-Glycoprotein Reveals a Molecular Basis for Poly-Specific Drug Binding," *Science* 323(5922):1718-1722 (2009) and Kuo et al., "Expression of P-Glycoprotein and Multidrug Resistance-Associated Protein on Human Brain-Microvascular Endothelial Cells With Electromagnetic Stimulation," *Colloids Surf. B Biointerfaces* 91:57-62 (2012), which are hereby incorporated by reference in their entirety). Moreover, P-gp expression or upregulation in various cancers and cell types poses a poor prognosis for cancers and cancer treatment (Chung et al., "P-Glycoprotein: The Intermediate End Point of Drug Response to Induction Chemotherapy in Locally Advanced Breast Cancer," *Breast Cancer Res. Treat.* 42(1):65-72 (1997), which is hereby incorporated by reference in its entirety). Therefore, the data of the present application showing that signaling via the A2A AR alters P-gp function has very broad appeal beyond the CNS. These data indicate that AR modulation may be a bona fide mechanism of altering P-gp function to effectively treat major cancers in general. These studies mark a significant and surprising advance over previous work relating to the BBB and open the door to major advances in the control of drug efflux from cells.

Until recently, the brain was considered a formidable fortress that doesn't allow the entry of molecules or cells into the CNS. However, technological advancement and emerging studies have revealed that the brain is not totally cut off from the rest of the body; rather, it is selectively separated in order to maintain proper brain physiology (Abbott N. J., "Astrocyte-Endothelial Interactions and Blood-Brain Barrier Permeability," *J. Anat.* 200(6):629-638 (2002) and Deeken et al., "The Blood-Brain Barrier and Cancer: Transporters, Treatment, and Trojan Horses," *Clin. Cancer Res.* 13(6):1663-1674 (2007), which are hereby incorporated by reference in their entirety). Adenosine is a damage/danger-signaling molecule that responds to cell stress or tissue damage by inducing a cascade of events involving recruitment of cells and substances across biological barriers needed to repair damaged tissues (Hasko et al., "Adenosine Receptor Signaling in the Brain Immune System," *Trends Pharmacol. Sci.* 26(10):511-516 (2005) and Jacobson et al., "Adenosine Receptors as Therapeutic Targets," *Nat. Rev. Drug Discov.* 5(3):247-264 (2006), which are hereby incorporated by reference in their entirety). Therefore, adenosine is an endogenous (built in) modulator that regulates BBB permeability to recruit molecules into the CNS (to repair it) during CNS damage or stress. AR signaling may function as a door, with adenosine acting as the key that signals its opening. This built-in mechanism may rely on the extremely short half-life of adenosine (about 10 seconds) to reverse BBB permeability.

A2A AR modulation of the BBB may offer a safe means of delivering drugs into the CNS. AR modulation of BBB permeability provides a kinetic window of P-gp down-modulation that can be exploited to deliver therapeutics to treat diseases ranging from primary brain tumors to AD. It offers a time line of drug delivery to the brain that can be transient or gradual, depending on the A2A AR agonist used. Importantly, BBB permeability is reversed, returning to steady state after the effects of the agonist wane. ARs and the enzymes that generate extracellular adenosine are expressed directly on BBB cells, and some AR pharmacological agents, including Lexiscan®, are FDA approved and may lessen some potential hurdles for use in humans. In summary, the Examples of the present application show that AR mediates P-gp function in BBB permeability. These results are exciting, highly translational, and stand to have a high impact on public health. A2A AR modulation of BBB via regulation of P-gp may provide a real alternative in treating brain tumors such as gliomas, which are incurable and have an average survival time of 18 months.

Figure 16A:
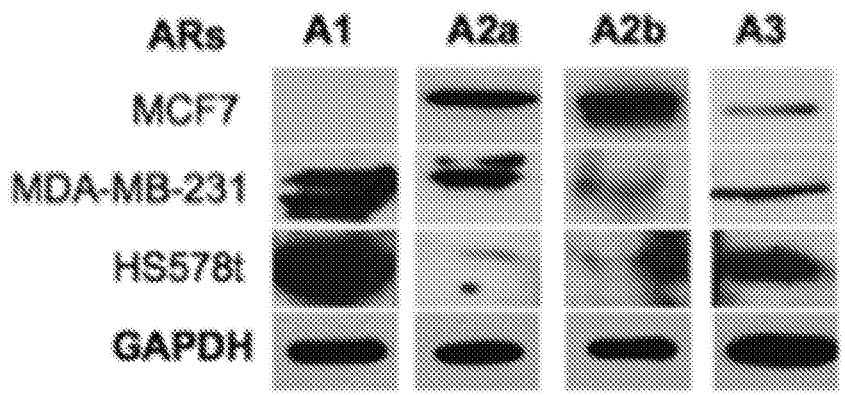
FIGS. 16A-16B shows adenosine receptor expression breast cancer cell lines.
Figure 16B:
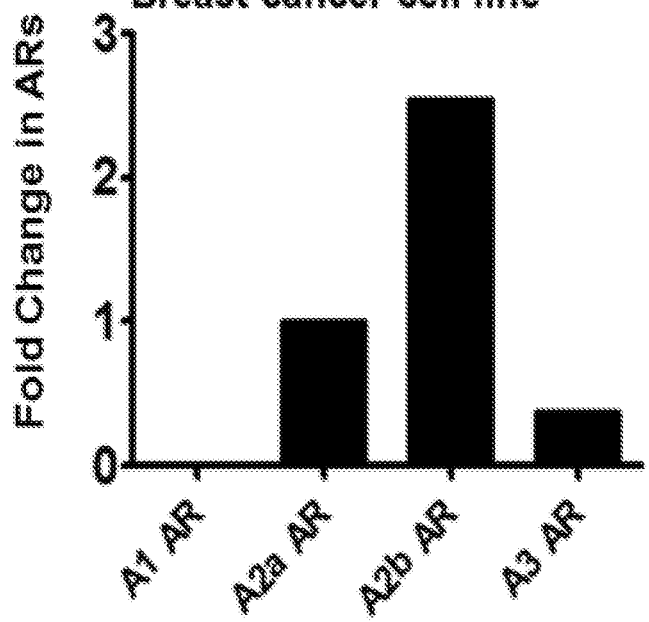

Example 6—A2A AR and A2B AR Activation Down-Modulates P-gp Function in the Breast Cancer Cell Lines To confirm the expression of adenosine receptors in human breast cancer cell lines, western blot analysis of MCF7, HS578t, and MDA-MB-231 cell lysates was performed using AR1-, AR2A-, AR2B-, and AR3-specific antibodies. All three cell lines expressed A2A AR, whereas only HS578t and MDA-MB-231 cells were positive for A1 AR (FIG. 16A). MCF7 cells were also positive for A2B AR (FIG. 16A). FIG. 16B shows densitometric analysis of AR expression levels in MCF7 cells normalized by GAPDH.

Figures 17A, 17B, 17C, 17D:
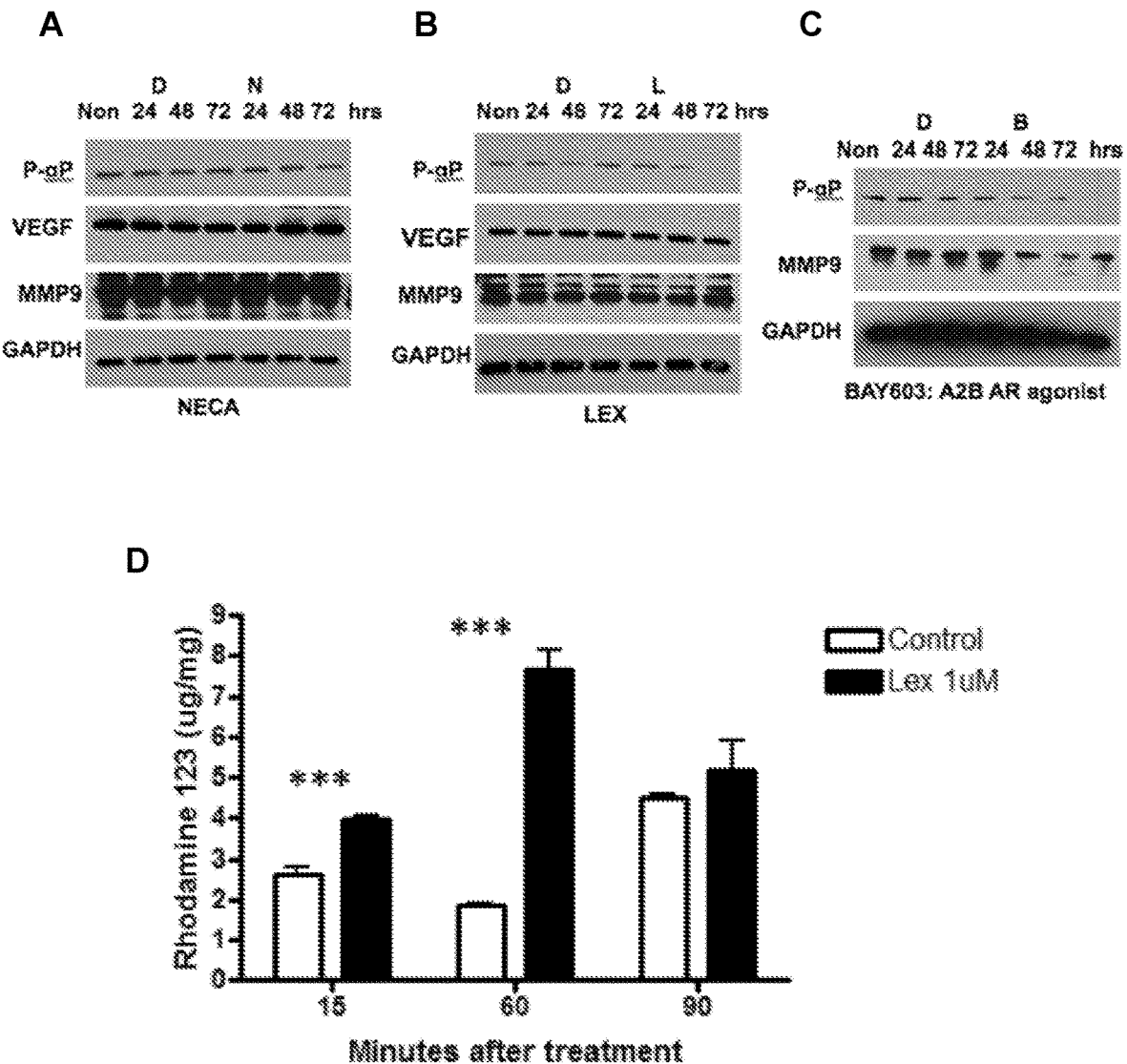
FIGS. 17A-17F show that Lexiscan® downregulates P-gp expression in MCF7 Breast cancer cells. MCF7 cells (human breast cancer cell line) were cultured in 24 well plates until they reached confluency.

Whether activation of the A2A and A2B ARs modulates P-gp expression in the breast cancer cell line MCF7 was next investigated. Treatment of MCF7 cells with the A2A AR agonist Lexiscan® or NECA decreased P-gp expression in cultured MCF7 cells at 48 and 72 hour time points (FIGS. 17A (NECA) and 17B (Lexiscan®)). Similar results were observed when MCF7 cells were treated for 48-72 hours with the A2B AR agonist BAY603 (FIG. 17C). These results indicate that A2A AR and A2B AR modulate P-gp expression in the human breast cancer cell line MCF7.

The down-modulation of P-gp using Lexiscan® in MCF7 cells was verified using a Rho123 assay. Briefly, MCF7 cells were treated with 0.025 µM Lexiscan® concomitant with Rho123, a P-gp substrate. FIG. 17D shows that significant Rho123 accumulation occurred by 15 minutes and 60 minutes, as compared with vehicle control. These results are consistent with the results seen in FIG. 17B.

Figure 17E:
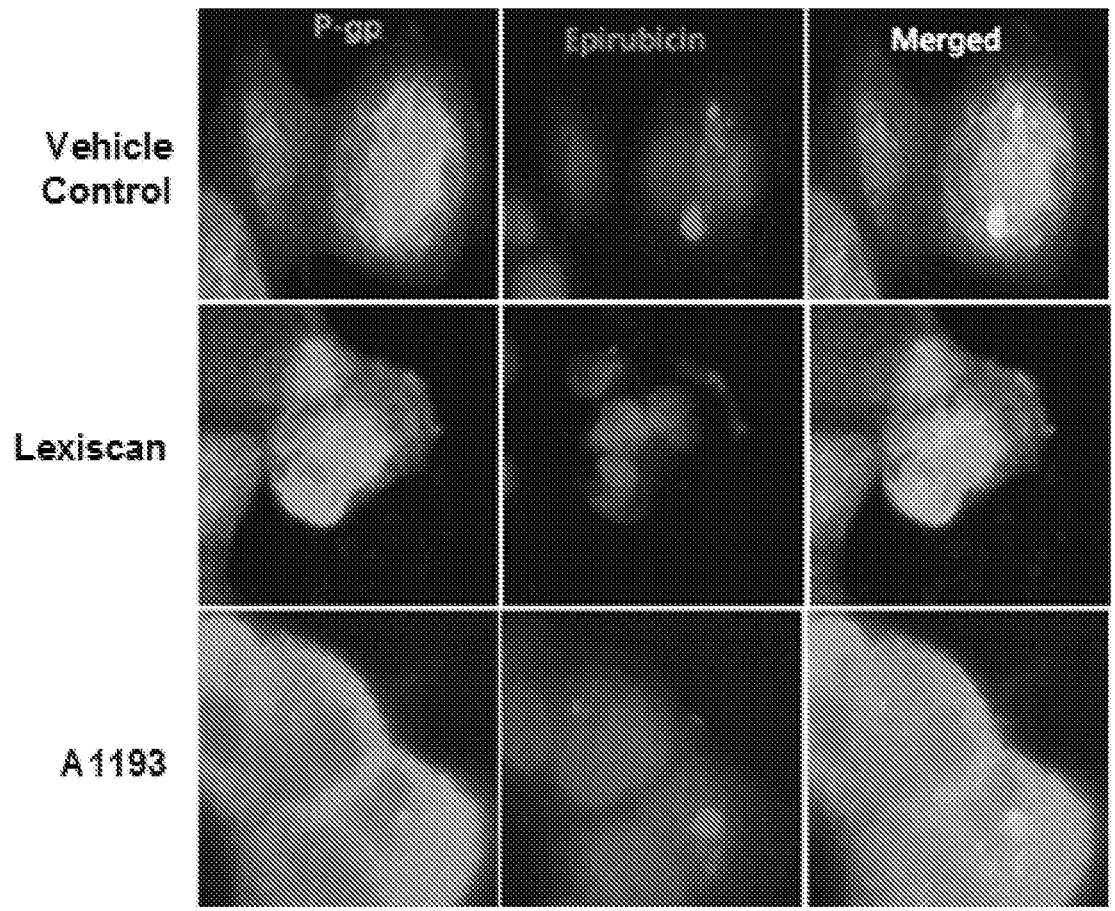
Figure 17F:
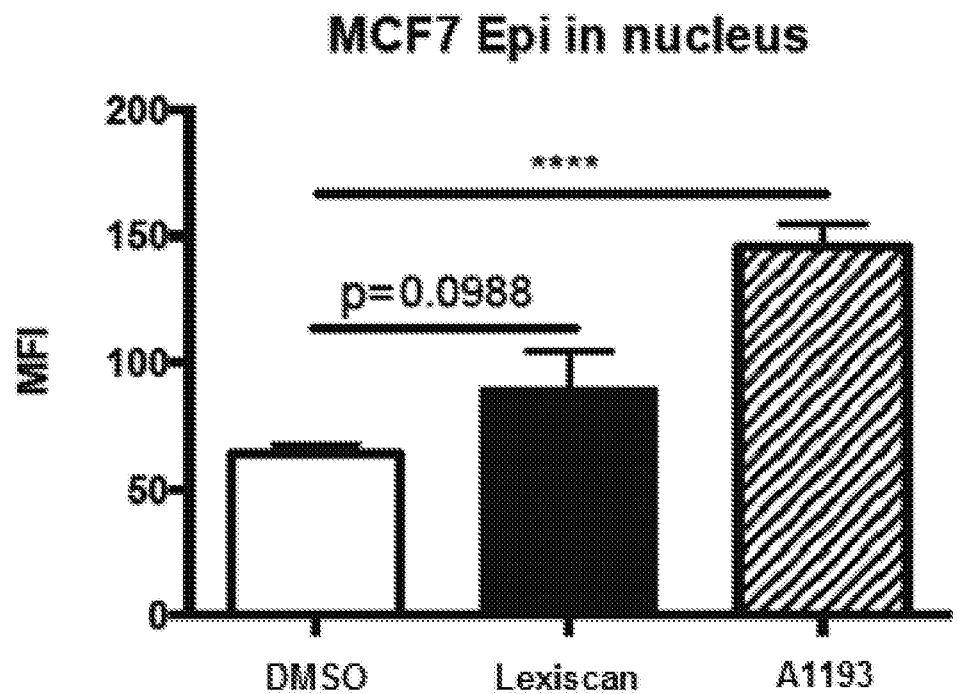

To further assess the modulation of A2A AR agonists on P-gp expression in MCF7 cells, applicants evaluated the accumulation of the P-gp substrate epirubicin in MCF7 cells. MCF7 cells were treated with DMSO (control), 1 µM Lexiscan®, or 1 µM of the A2A AR agonist A1193. FIG. 17E shows the accumulation of epirubicin in Lexiscan® and A1193 treated cells. Cells treated with Lexiscan® retained more epirubicin than those treated with control (FIG. 17F). Similarly, cells treated with A1193 retained significantly more epirubicin than those treated with control (FIG. 17F). These results indicate that A2A AR agonists modulate the function of P-gp in the cancer cell line MCF7. In this case, the down-regulation of P-gp expression is equivalent to down-regulation of its function (Kim et al., "A2A Adenosine Receptor Modulates Drug Efflux Transporter P-Glycoprotein at the Blood-Brain Barrier," *J Clin Invest.* 126(5):1717-33 (2016), which is hereby incorporated by reference in its entirety).

Figure 18A:
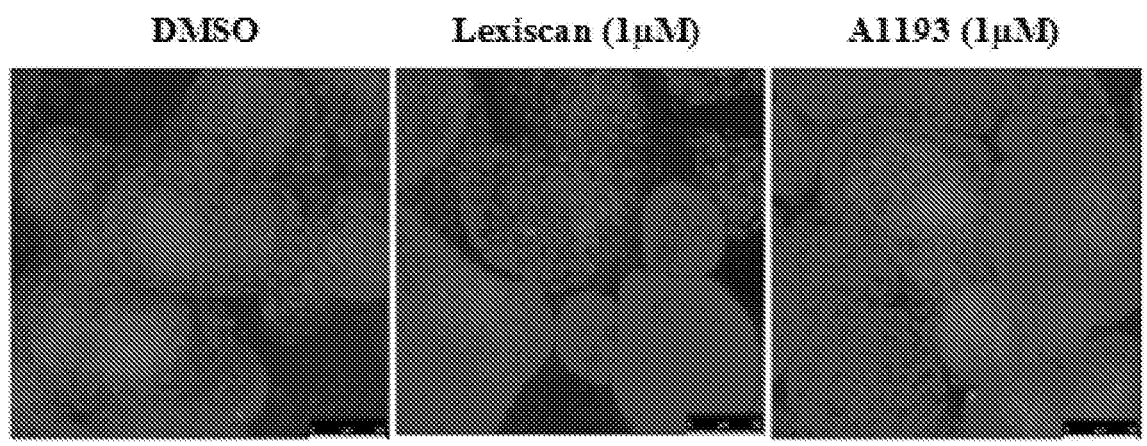
FIGS. 18A and 18B show that Lexiscan® significantly down-regulates P-gp expression in freshly isolated and cultured gut epithelial cells.
Figure 18B:
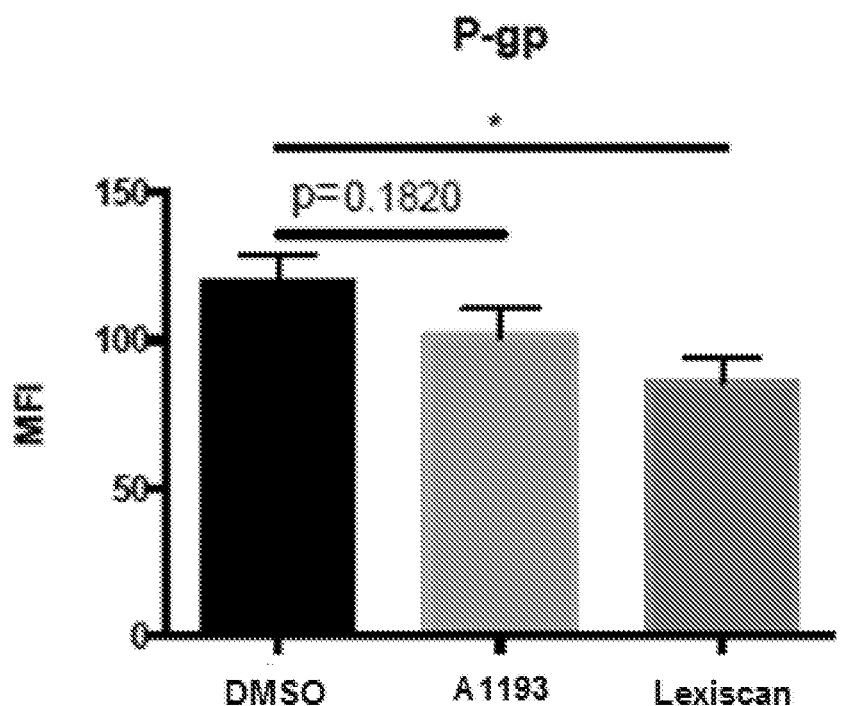

Example 7—A2A AR Activation Down-Modulates P-gp Function in Intestinal Organoids Applicants next evaluated whether A2A AR agonists can modulate P-gp expression in gut epithelial cells. Freshly isolated intestines from wildtype C57BL6 mice were cultured and grown to confluency to generate Organoids, which are three-dimensional organotypic cultures derived from primary intestinal tissues (either tissue subunits or single cells), embryonic stem cells ("ESCs"), or induced pluripotent stem cells ("iPSCs"). Organoids were treated with the A2A AR agonists Lexiscan® or A1193 for 15 minutes, washed, and stained with antibodies to P-gp and DAPI. FIGS. 18A-18B show that Lexiscan® significantly down-regulates P-gp expression in freshly isolated and cultured colonic organoids, consisting of a mixture of gut epithelial cells, gut colonic stem cells, and mature colonic cells. These results suggest that these different "potential" intestinal cells are responsive to P-gp and can be altered by an A2A AR agonist or an A2A AR antagonist.

Figure 19A:
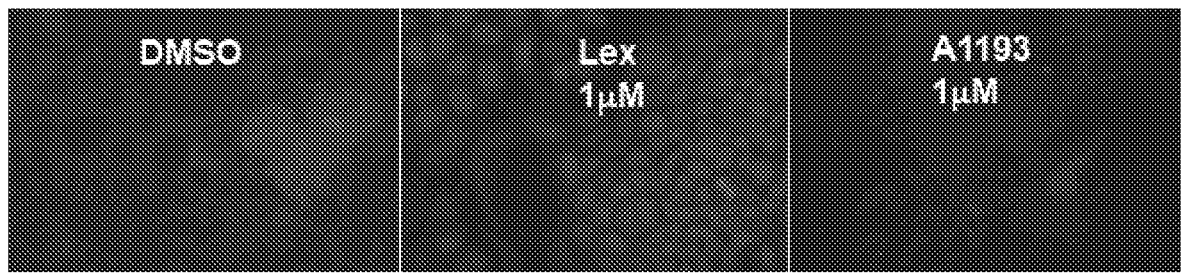
FIGS. 19A-19C show that the A2A AR agonists Lexiscan® ("Lex") and A1193 downregulate P-gp expression in the Caco-2 human tumor cell line.
Figure 19B:
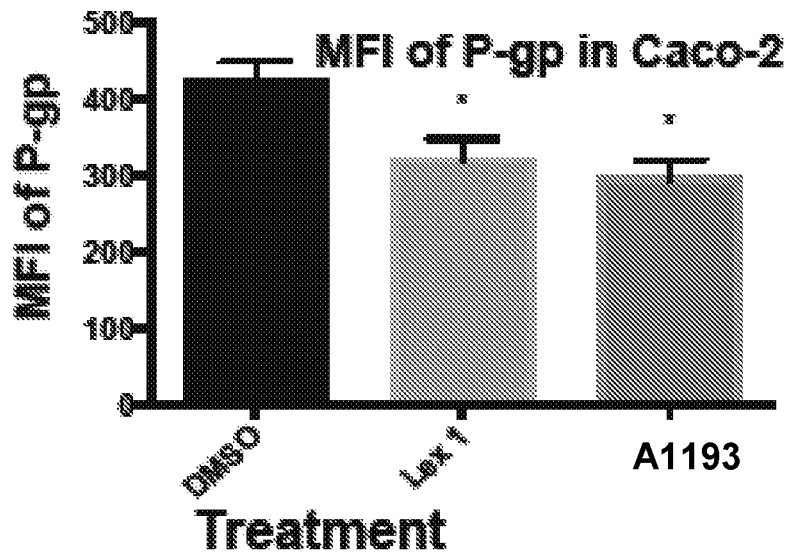
Figure 19C:
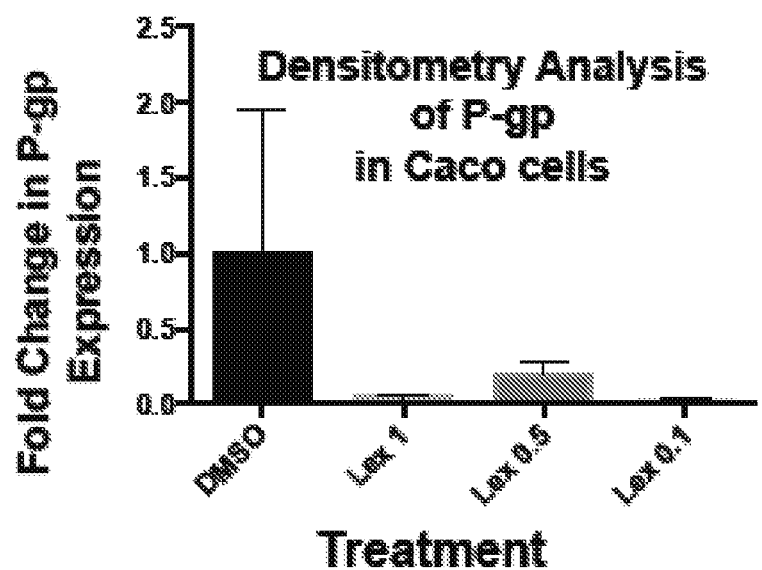

Example 8—A2A AR Activation Down-Modulates P-gp Expression in Caco-2 Human Tumor Cell Line Applicants also evaluated whether A2A AR agonists can modulate P-gp expression in a human tumor cell line, Caco-2 cells. Briefly, Caco-2 cells (originally isolated from a human tumor) were grown on coverslips and treated with Lexiscan®, A1193, or vehicle control for 30 minutes. Cells were then fixed, permeabilized, and stained with an antibody to P-gp. After washing, cells were mounted with DAPI for nuclear staining (FIG. 19A). The mean fluorescence intensity (MFI) of P-gp was quantified and graphed in FIG. 19B. FIG. 19C shows western blot analysis of Caco-2 cells treated with varying concentrations of Lexiscan®. Overall, the results of FIGS. 19A-19C demonstrate that the A2A AR agonist Lexiscan® down-regulates P-gp expression in Caco-2. These results indicate that P-gp may be applied to the treatment of colon cancer or in cases of leaky gut barrier, it may be applied to restrict gut barrier leakiness.

Figure 20A:
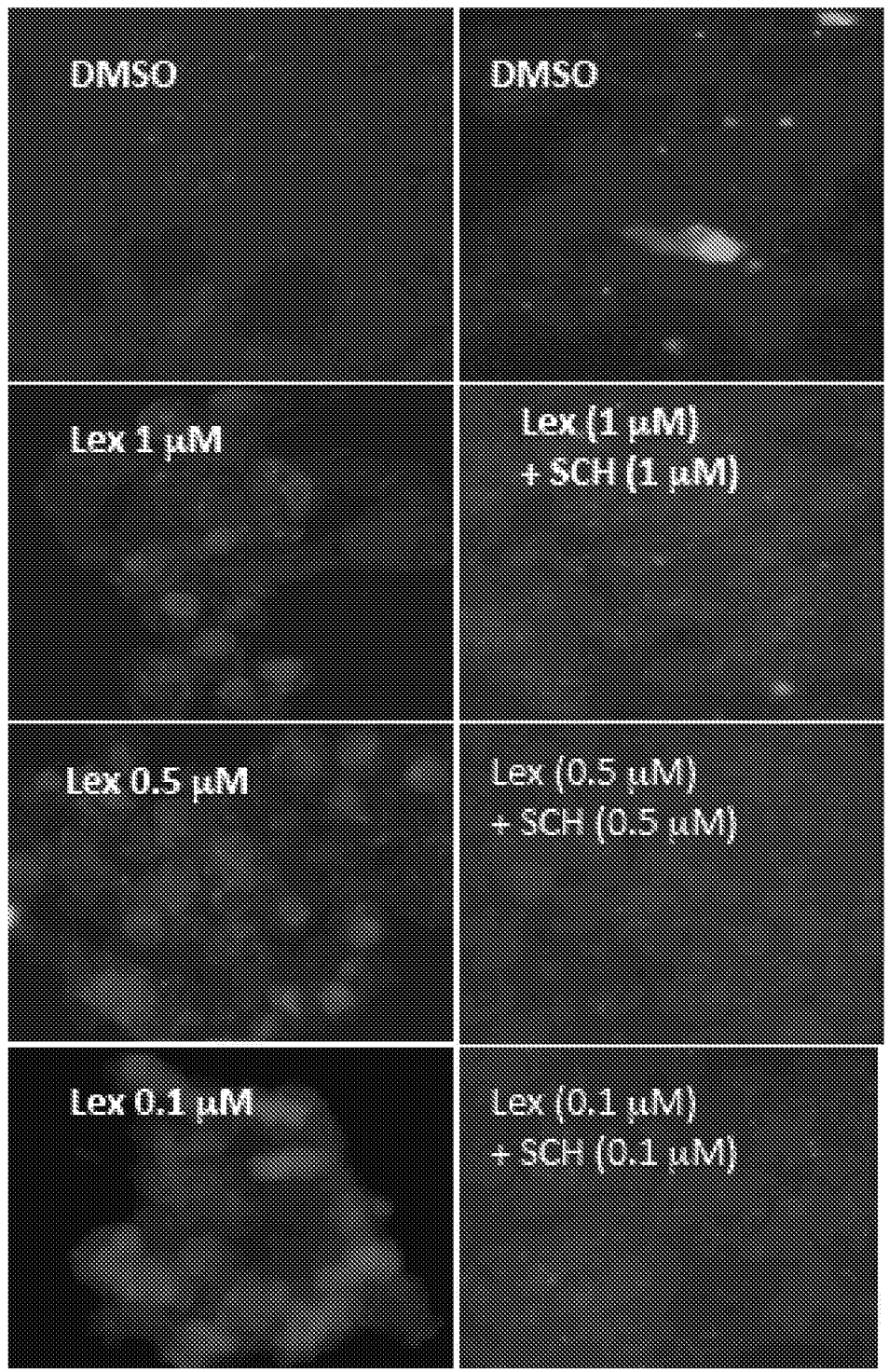
FIGS. 20A and 20B illustrate that Lexiscan® downregulates P-gp expression in the kidney cell line HEK293T while treatment with antagonist SCH58261 blocks Lexiscan®'s effects.
Figure 20B:
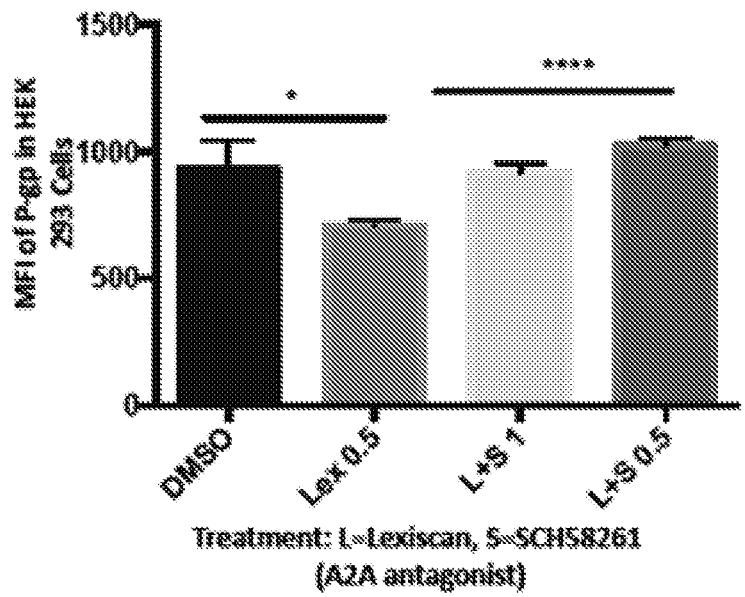

Example 9—A2A AR Activation Down-Modulates P-gp Expression in the HEK293T and HEK293T Kidney Cell Lines Applicants investigated whether A2A AR agonists could modulate P-gp expression in the HEK293T human kidney cell line. HEK293T cells were grown to confluency on coverslips and treated with varying concentrations of Lexiscan, Lexiscan® plus the A2A antagonist (SCH58261), or vehicle control for 15 minutes. Cells were then permeabilized, stained with an antibody to P-gp, and visualized under a fluorescent microscope (FIG. 20A). The mean fluorescence intensity (MFI) of P-gp was quantified and graphed in FIG. 20B. FIGS. 20A-20B demonstrate that the A2A AR agonist Lexiscan® down-regulates P-gp expression in HEK293T cells, whereas SCH58261 treatment blocked the effects of Lexiscan®.

Figure 21:
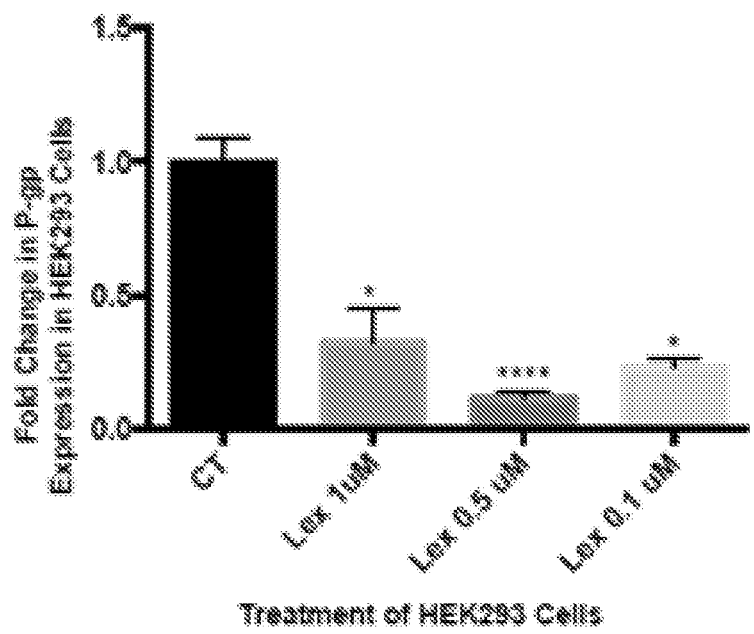
FIG. 21 is a graph summarizing experimental results that show that Lexiscan® significantly down-regulated P-gp expression in the transformed HEK293T cell line. HEK293T transformed kidney cells were treated with varying concentration of Lexiscan® (1, 0.5, 0.1 µM). Cells were lysed with lysis buffer (RPMI), containing protease inhibitor cocktail. Samples were loaded on 7% SDS PAGE at 100V for 1 hour and transferred to nitrocellulose paper. The intensity of bands were analyzed by densitometry and plotted as a graph. Statistics: two-tailed student's t test: *=P<0.5, ****=P<0.0001.

HEK293T cells were treated with various concentrations of Lexiscan, lysed, loaded onto an SDS-PAGE gel, transferred to a nitrocellulose membrane, and used for western blot analysis. Densitometry analysis of the blot showed that Lexiscan® ("Lex") significantly down-regulated P-gp expression in transformed HEK293T cells (FIG. 21).

Discussion of Examples 1-9

Examples 6-9 of the present application show that: (i) decrease in P-gp expression is directly linked to decrease in its function and (ii) that both A2A and A2B AR agonists can down-regulate P-gp expression or function. These results further indicate that antagonism of A2A AR or A2B AR can be used to upregulate P-gp expression or function, to tighten biological barriers (gut, brain, testes, kidneys, eyes, etc.), and to protect the host in cases of leaky barriers and organs that are deemed immune privileged.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inhibiting p-glycoprotein (P-gp) expression in a cell, the method comprising:
contacting a cell expressing P-gp with a composition comprising an effective amount of a selective A2A adenosine receptor (A2A AR) agonist to inhibit P-gp expression in the cell, wherein the selective A2A AR agonist is regadenoson, apadenoson, binodenoson, CGS 21680, YT-146, DPMA, PBS 0777 ammonium salt, or A1193; and, wherein said cell expressing P-gp is a cell of the intestine, pancreatic ductules, bile ductules, kidney, adrenal gland; a gonad cell; a breast cell; or a cardiac cell.

2. The method of claim 1, wherein the cell is of the intestine, pancreatic ductules, bile ductules, kidney, or adrenal gland.

3. The method of claim 1, wherein the cell is a gonad cell.

4. The method of claim 1, wherein the cell is a breast cell.

5. The method of claim 4, wherein the cell also expresses Breast Cancer Resistance Protein 1 (BCRP1) and said contacting is effective to inhibit BCRP1 expression in the cell.

6. The method of claim 1, wherein the cell is a cardiac cell.

7. The method of claim 1, wherein the cell is a neoplastic cell.

8. The method of claim 7, wherein the neoplastic cell has increased P-gp expression, as compared to a non-neoplastic cell.

9. The method of claim 1, wherein said method is carried out in vivo and further comprises: selecting a subject having a disease or disorder and in need of increased bioavailability of a therapeutic to treat the disease or disorder,
wherein said contacting comprises administering the composition to the selected subject, thereby sensitizing P-gp-expressing cells of the subject to uptake of the therapeutic.

10. The method of claim 9, wherein the selected subject has a cardiac disease or disorder.

11. The method of claim 9, wherein the disease or disorder is cancer.

12. The method of claim 11, wherein the cancer is multi-drug resistant (MDR) cancer.

13. The method of claim 12, wherein the cancer is within the central nervous system (CNS).

14. The method of claim 9, wherein said method further comprises:
administering to the selected subject the therapeutic to treat the disease or disorder.

15. The method of claim 14, wherein the subject has a cardiac disease or disorder and the therapeutic is a *digitalis*-like compound.

16. The method of claim 14, wherein the subject is undergoing tissue transplant and the therapeutic is an mTOR inhibitor.

17. The method of claim 14, wherein the subject has cancer and the therapeutic is a chemotherapeutic.

18. The method of claim 1, wherein the selective A2A AR agonist is regadenoson.

19. The method of claim 7, wherein the neoplastic cell is a melanoma cell, a breast cancer cell, an ovarian cancer cell, a prostate cancer cell, a sarcoma cell, a hepatoma cell, a glioma cell, a mesothelioma cell, or a carcinoma cell.

* * * * *

UNITED STATES PATENT AND TRADEMARK OFFICE
CERTIFICATE OF CORRECTION

PATENT NO. : 10,953,015 B2
APPLICATION NO. : 16/075195
DATED : March 23, 2021
INVENTOR(S) : Margaret Bynoe Page 1 of 1

It is certified that error appears in the above-identified patent and that said Letters Patent is hereby corrected as shown below:

In the Claims

Claim 15, Column 44, Lines 58-59 delete "and the therapeutic is a digitalis-like compound".

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*